United States Patent [19]

Taylor, Jr. et al.

[11] Patent Number: 4,956,359
[45] Date of Patent: Sep. 11, 1990

[54] 3-ARYLOXY AND 3-ARYLTHIOAZETIDINECARBOXAMIDES AS ANTICONVULSANTS AND ANTIEPILEPTICS

[75] Inventors: Chandler R. Taylor, Jr.; Albert D. Cale, Jr., both of Mechanicsville; Harold F. Stauffer, Jr., Midlothian, all of Va.

[73] Assignee: A. H. Robins Company, Inc., Richmond, Va.

[21] Appl. No.: 921,466

[22] Filed: Oct. 22, 1986

Related U.S. Application Data

[63] Continuation-in-part of Ser. No. 706,621, Feb. 28, 1985, abandoned.

[51] Int. Cl.$^5$ ............................................. A61K 31/395
[52] U.S. Cl. ................................... 514/210; 540/515; 540/596; 544/111; 544/349; 544/359; 546/208; 546/256; 546/275; 548/336; 548/524; 548/952
[58] Field of Search .................. 514/210; 540/575, 596; 544/111, 349, 359; 546/208, 256, 275; 548/336, 524, 952

[56] References Cited

U.S. PATENT DOCUMENTS

| | | | |
|---|---|---|---|
| 4,226,861 | 10/1980 | Cale, Jr. .............................. | 514/210 |
| 4,505,907 | 3/1985 | Wright et al. ...................... | 514/210 |
| 4,571,393 | 2/1986 | Teng .................................... | 514/210 |
| 4,594,189 | 1/1986 | Lo et al. .............................. | 548/952 |

FOREIGN PATENT DOCUMENTS 102194  3/1984  European Pat. Off. ............ 548/952

OTHER PUBLICATIONS

Albertson, et al., Chem. Abstracts vol. 101 (1984), entry 183856e.

Osman, et al., Chem. Abstracts vol. 102 (1985), entry 72276S.

*Primary Examiner*—Mukund J. Shah
*Assistant Examiner*—C. L. Cseh

[57] ABSTRACT

Novel 3-aryloxy and 3-arylthioazetidinecarboxamides having utility in a method of treating convulsions and epilepsy and compositions therefor are disclosed having the formula:

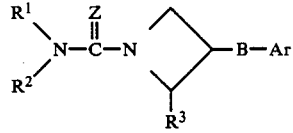

wherein Z is oxygen or sulfur; B is oxygen or sulfur; Ar is pyridyl or halo-substituted-pyridyl, phenyl or substituted phenyl; $R^1$ and $R^2$ are selected from hydrogen, loweralkyl, aryl, allyl, substituted allyl, propargyl, cycloalkyl, loweralkylcycloalkyl, cycloalkylloweralkyl, arylloweralkyl, diloweralkylaminoloweralkyl, and $R^1$ and $R^2$ when taken with the adjacent nitrogen atom may form a heterocyclic radical; $R^3$ is hydrogen, loweralkyl, aryl or arylloweralkyl, and the geometrical isomers thereof, excepting that when $R^3$ is hydrogen, Z is oxygen, B is oxygen, and Ar is phenyl or phenyl substituted by trifluoromethyl or aminocarbonyl, then $R^1$ and $R^2$ cannot be a combination of hydrogen and loweralkyl, and the further exception that when $R^3$ is hydrogen, Z is oxygen, B is oxygen, and Ar is phenyl or phenyl substituted by fluoro, loweralkyl, loweralkoxy, trifluoromethyl, acetyl, or aminocarbonyl, then $R^1$ and $R^2$ cannot both be hydrogen.

94 Claims, No Drawings

3-ARYLOXY AND 3-ARYLTHIOAZETIDINECARBOXAMIDES AS ANTICONVULSANTS AND ANTIEPILEPTICS

This application is a continuation-in-part application of copending U.S. patent application Ser. No. 706,621 filed Feb. 28, 1985 now abandoned.

BACKGROUND OF THE INVENTION

1. Field of Invention.

This invention relates to certain novel 3-aryloxy and 3-arylthioazetidinecarboxamides, methods of treatment for anticonvulsant effect and epilepsy therewith and pharmaceutical compositions thereof.

2. Description of the Prior Art.

Certain mono-N-substituted azetidinecarboxamides are disclosed in U.S. Pat. No. 4,226,861 as having anticonvulsant activity and useful in treating epilepsy having the formula:

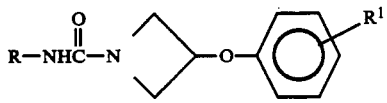

wherein R is loweralkyl and $R^1$ is hydrogen, aminocarbonyl or trifluoromethyl.

N-Unsubstituted-azetidinecarboxamides are disclosed and claimed in U.S. Pat. No. 4,571,393 as having anticonvulsant activity and use in treating epilepsy having the formula:

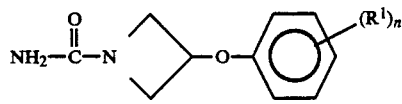

wherein $R^1$=H, F, loweralkyl, loweralkoxy, trifluoromethyl, acetyl or aminocarbonyl. U.S. Pat. No. 4,571,393 was derived from an earlier parent of U.S. application Ser. No. 409,476 filed on Aug. 19, 1982, now abandoned, which was the basis for European patent application Ser. No. 102-194-A which has since been published.

A U.S. application Ser. No. 706,632, filed on Feb. 28, 1985, now abandoned discloses a method of treating muscle tension and spasticity and anxiety with all of the prior art compounds mentioned above and the compounds disclosed in the present application.

SUMMARY OF THE INVENTION

The 3-aryloxy and 3-arylthioazetidinecarboxamides useful in the method of this invention have the formula:

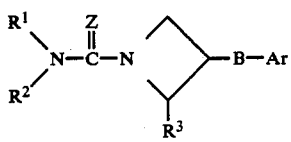

Formula I wherein Ar is selected from pyridyl in any of its positions, including pyridyl substituted by halo, from phenyl or phenyl substituted by 1 or 2 radicals selected from chloro, bromo, iodo, fluoro, loweralkyl, loweralkoxy, nitro, aminocarbonyl or trifluoromethyl;

B is oxygen or sulfur;

Z is oxygen or sulfur;

$R^1$ and $R^2$ may be the same or different and are selected from hydrogen, loweralkyl, aryl, allyl, substituted allyl, propargyl, cycloalkyl, loweralkylcycloalkyl, cycloalkylloweralkyl, arylloweralkyl, and diloweralkylaminoloweralkyl, and $R^1$ and $R^2$ when taken together with the adjacent nitrogen atom may form a heterocyclic amine radical including azetidinyl, pyrrolidinyl, piperidinyl, homopiperidinyl, imidazolyl, piperazinyl, (halophenyl) piperidin-1-yl, phenyl-1,2,3,6-tetrahydropyridin-1-yl, phenylpiperidin-1-yl, hydroxypiperidin-1-yl, 4-morpholino, 4-(3,5-diloweralkyl)morpholino, 4-(2,6-diloweralkyl)-morpholino, 1,2,3,6-tetrahydropyridin-1-yl, (halophenyl) (hydroxy)piperidin-1-yl, pyrrolo[1,2-a]pyrazin-2-yl, homopiperazinyl, 4-substituted piperazinyl, and 4-substituted homopiperazinyl;

$R^3$ is selected from hydrogen loweralkyl, aryl or arylloweralkyl; the geometrical isomers, including cis, trans, (E) and (Z) isomers thereof, and the pharmaceutically acceptable acid addition salts thereof when $R^1$ and $R^2$ have one or more salt-forming basic amino components or when Ar is pyridinyl, and the hydrates thereof, with the proviso that when $R^3$ is hydrogen, Z is oxygen, B is oxygen, and Ar is phenyl or phenyl substituted by trifluoromethyl or aminocarbonyl, then $R^1$ and $R^2$ cannot be a combination of hydrogen and loweralkyl, and the further proviso that when $R^3$ is hydrogen, Z is oxygen, B is oxygen, and Ar is phenyl or phenyl substituted by fluoro, loweralkyl, loweralkoxy, trifluoromethyl, acetyl, or aminocarbonyl, then $R^1$ and $R^2$ cannot both be hydrogen.

In the further definition of symbols in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, secbutyl, tert-butyl, amyl, isoamyl, hexyl, heptyl, and octyl radicals and the like. The term "loweralkoxy" has the formula -O-loweralkyl.

The term "cycloalkyl" as used herein includes primarily cyclic alkyl radicals containing 3-9 carbon atoms inclusive and includes such groups as cyclopropyl, cyclobutyl, cyclopentyl, cyclohexyl, cycloheptyl, and the like.

The term "loweralkylcycloalkyl" refers to cycloalkyl substituted by alkyl radicals of 1-8 carbon length.

The term "cycloalkylloweralkyl" refers to a cyclicalkyl radical linked via 1-8 carbon alkyl chains, including branched chains, to the amide nitrogen.

The term "substituted allyl" means allyl substituted by alkyl radicals in any one of its 3 positions.

The term "aryl" under the definition of $R^1$, $R^2$, and $R^3$ refers to phenyl or phenyl substituted by non-interfering radicals such as halo, loweralkyl, loweralkoxy, nitro, cyano, trifluoromethyl, carbomethoxy, carboethoxy, and the like.

The term "arylloweralkyl" under the definition of $R^1$, $R^2$, and $R^3$ refers to an aryl group as defined above linked via 1-8 carbon alkyl chains, including branched chains, to the amide nitrogen.

The term "4-substituted-piperazinyl" under the definition of $R^1$ and $R^2$ refers to a piperazine radical substituted by radicals usually in the pharmaceutical art, including phenyl, halophenyl, loweralkoxyphenyl, 2, 3 or 4-pyridinyl, 2, 4 or 5-pyrimidinyl, nitrophenyl, trifluoromethylphenyl, loweralkyl, phenylloweralkyl, loweralkoxycarbonyl, and the like.

The term "4-substituted-homopiperazinyl" under the definition of $R^1$ and $R^2$ refers to a homopiperazinyl radical substituted by radicals usually in the pharmaceutical art, including phenyl, halophenyl, loweralkoxyphenyl, 2, 3 or 4-pyridinyl, 2, 4 or 5-pyrimidinyl, nitrophenyl, trifluoromethylphenyl, loweralkyl, phenylloweralkyl, loweralkoxycarbonyl, and the like.

The term "loweralkoxy-carbonyl" under the definition of 4-substituted piperazinyl and 4-substituted homopiperazinyl has the formula -C(O)-O-loweralkyl.

As defined above under Formula I, pharmaceutically acceptable salts are included when $R^1$ or $R^2$ have one or more salt-forming amino components or when Ar is pyridyl. Salt-forming amino components are present, for example, when either $R^1$ or $R^2$ are diloweralkylaminoloweralkyl or when they form piperazinyl or imidazolyl radicals or 4-(2-pyridinyl)-1-piperazinyl. Pharmaceutically acceptable acid addition salts are those salts which are physiologically compatible in warm-blooded animals. The acid addition salts may be formed either by strong or weak acids. Representative of useful strong acids are hydrochloric, hydrobromic, sulfuric and phosphoric acids. Representative of useful weak acids are fumaric, maleic, succinic, oxalic, citric, tartaric, hexamic, and the like.

The compounds of Formula I are useful in the method of this invention because of their pharmacological action on the central nervous system.

The procedure for testing the compounds for their anticonvulsant activity is based on evaluation techniques published by Swinyard, E. A., in EPILEPSIA 10: 107–19 (1969) and in J. PHARMAC. EXPTL. THERAP. 106: 319–30 (1952), and others as explained in greater detail below. The compounds demonstrate protective activity against seizures in both metrazole and electrical challenge and, consequently, are projected to generally have utility in treating both petit and grand mal epilepsy.

DETAILED DESCRIPTION OF THE INVENTION

The method used to prepare the compounds of Formula I are classified as follows by equation under method classes A, B, and C.

Method Class A
From Phenoxyazetidine

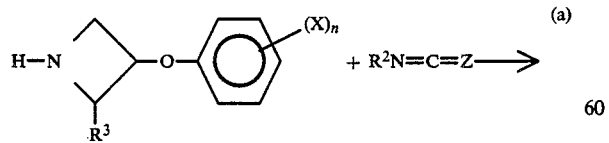

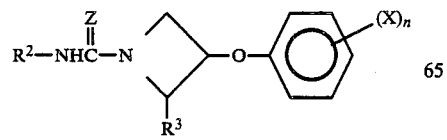

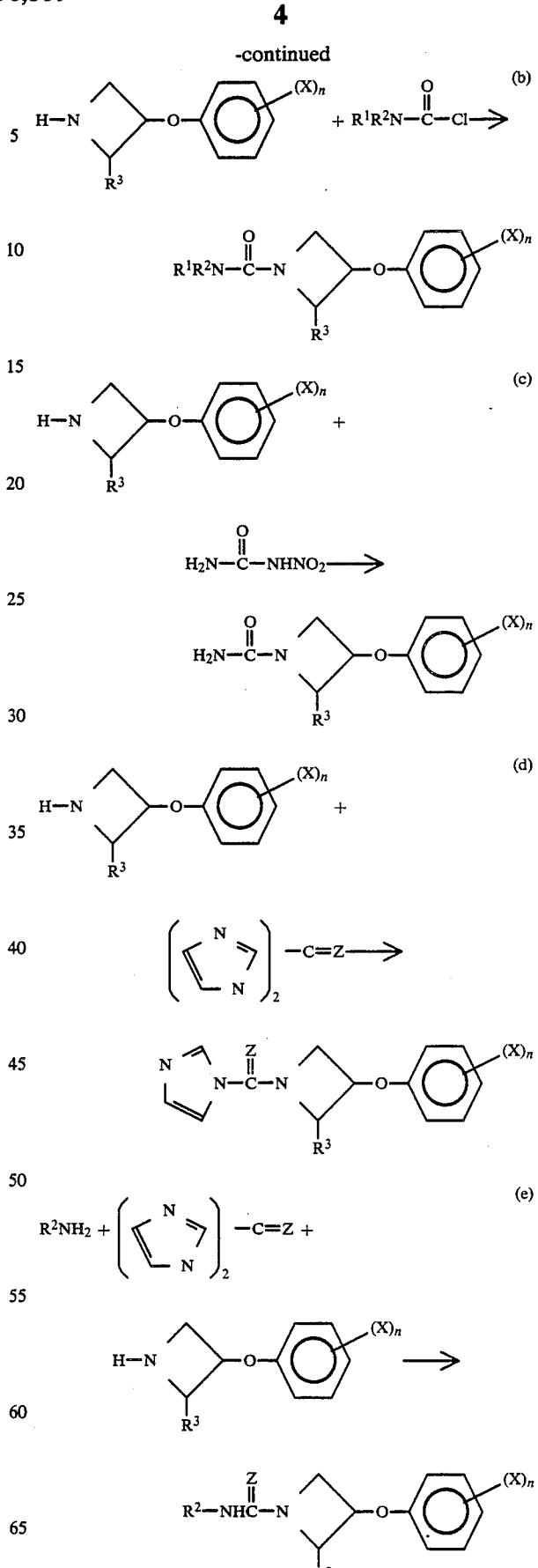

-continued (f)
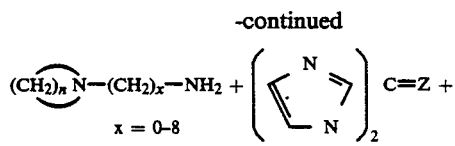

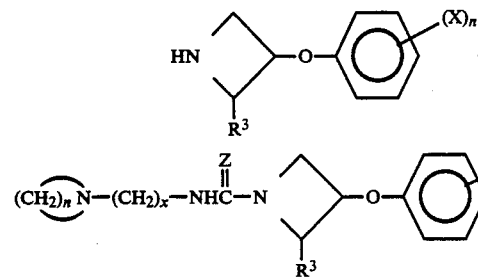

Method Class B
Via Aryloxy-(and Arylthio-)-1-chlorocarbonylazetidine
(Ar = Phenyl, Substituted-phenyl, Pyridyl)

(a)
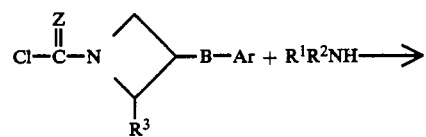

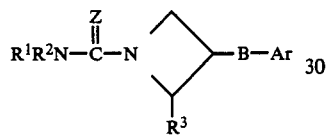

(b)
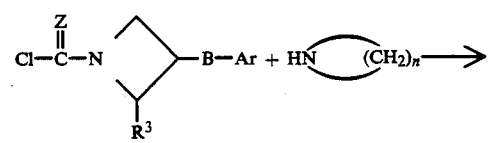

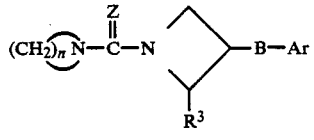

(c)
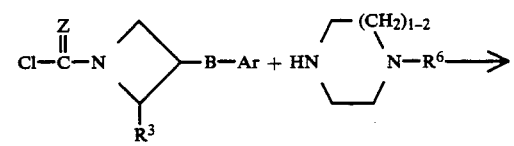

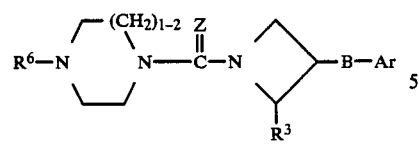

Optionally, when $R^6$ = H (See Example 111).

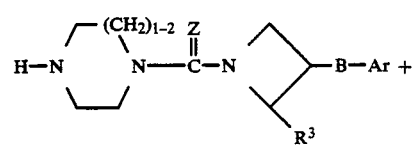

-continued

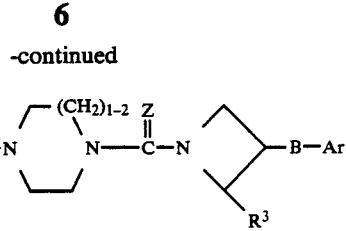

(d)
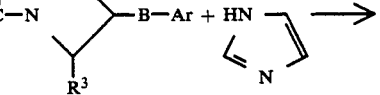

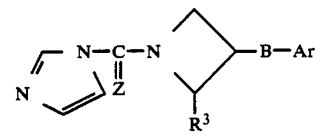

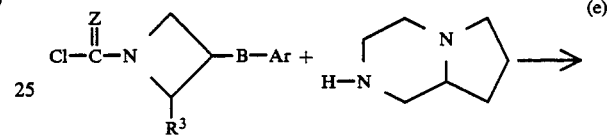

(e)
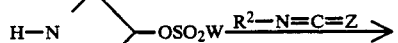

Method Class C
Via Methane (or Phenyl) sulfonyl azetidine

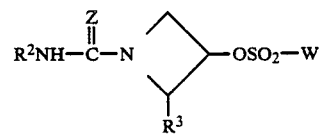

W = CH$_3$, C$_6$H$_5$—,
4-CH$_3$—C$_6$H$_4$—

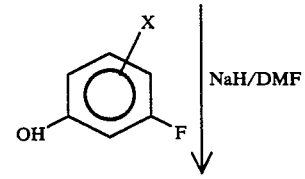

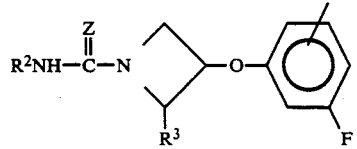

Method Class A reactions comprise a process for preparing phenoxy compounds of Formula I by reacting a compound of the formula:

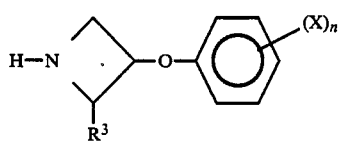

with one of the following classes of compounds:

(a) R²N═C═Z (b) R¹R²N—C—Cl
         ‖
         O

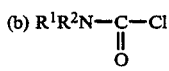
(c) H₂N—C—NHNO₂
      ‖
      O

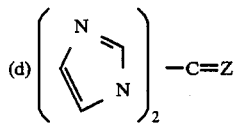
(d) $\left[\begin{matrix} N \\ \diagdown \\ N \end{matrix}\right]_2$—C═Z or, (e) and (f) the product of $\left[\begin{matrix} N \\ \diagdown \\ N \end{matrix}\right]_2$—C═Z and R²NH₂ or (CH₂)ₙ N—(CH₂)ₓ—NH₂ x = 0–8

Method Class B reactions comprise a process for preparing certain aryloxy and arylthio compounds of Formula I by reacting a compound of the formula:

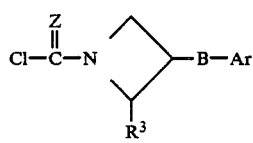

with one of the following classes of compounds:
(a) R¹R²NH, or,
(b) a heterocyclic amino compound.

Method Class C reactions comprise a process for preparing m-fluorophenoxy compounds of Formula I by reacting a compound of the formula:

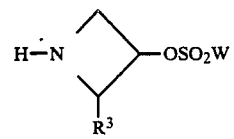

W = CH₃, C₆H₅, 4-CH₃—C₆H₅ with an isocyanate of the formula

R²—N═C═Z to give a compound of the formula

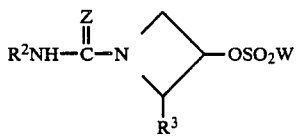

and thereafter reacting with sodium hydride and a metafluorophenol of the formula

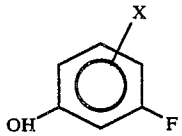

to give a compound of the formula

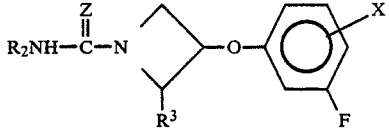

Methods of preparing the starting phenoxyazetidines used in Method Class A are outlined by equation in Chart I. Methods of preparing the starting aryloxy (and arylthio)-1-carbonylazetidines used in Method Class B are outlined by equation in Chart II.

The starting 1-(diphenylmethyl)-3-hydroxyazetidines may be prepared by the method of Anderson & Lok., J. ORG. CHEM. (1972) 37: 3953 from benzhydrylamine and an appropriate epihalohydrin. Cis and trans isomers are separated by chromatography when they exist. Starting α-methylbenzyl-3-azetidinol is prepared by the method of Tetsuya Okutani, et al., CHEM. PHARM. BULL. Vol. 22 (1974) p. 1490, and by the method analogous to the above Anderson et al. method for 1-(diphenylmethyl)-3-azetidinol. Preparations 1–26 illustrate the methods.

Chart I

Preparation of Starting
1-Unsubstituted phenoxyazetidines

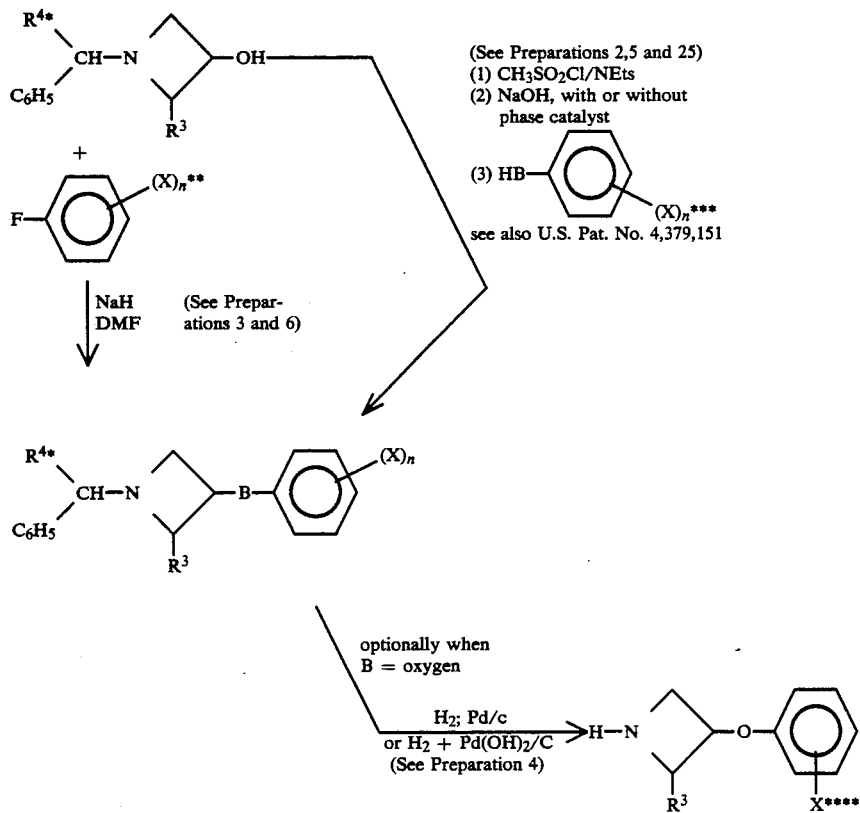

*$R^4$ = $CH_3$; phenyl or subst. phenyl.

**X is restricted to substituents that are electron withdrawing; e.g., fluoro, chloro, bromo, iodo or $CF_3$.

***When X = 4-cl, 4-Br, 4-I, 4-F or 4-$CF_3$, yields are very low.

****Except X cannot be chloro, bromo, or iodo in the product as hydrogenolysis removes these radicals.

Chart II

Preparation of Starting
1-Carbonyl-3-aryloxy (and arylthio) azetidines

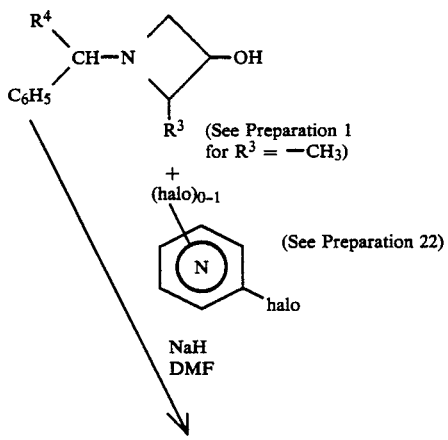

-continued
Chart II
Preparation of Starting 1-Carbonyl-3-aryloxy (and arylthio) azetidines

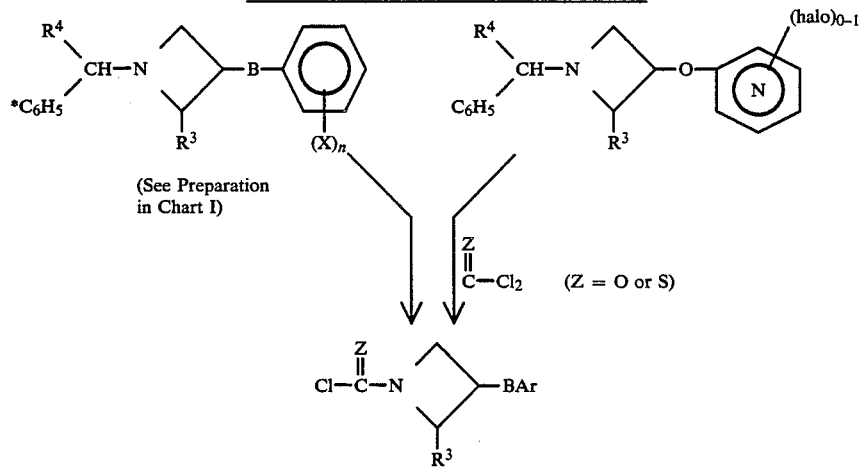

*Phenyl or phenyl substituted by non-interfering radicals.
$R^4$ = loweralkyl, phenyl or phenyl substituted by non-interfering radicals.

Chart III
Preparation of Starting Methane-(or phenyl)- sulfonylazetidine

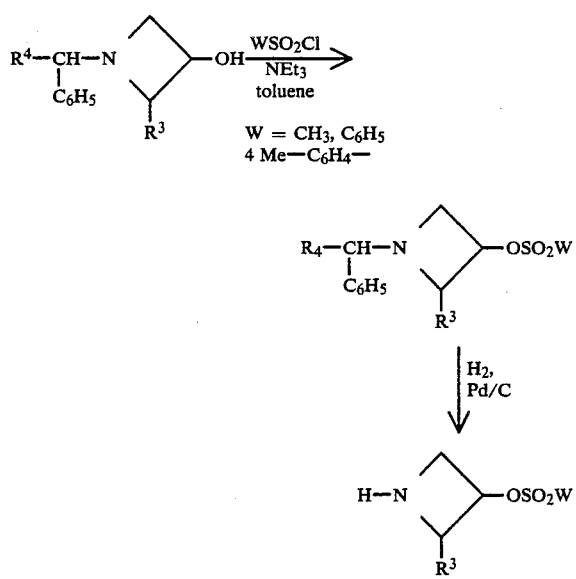

PREPARATION 1 trans-1-(Diphenylmethyl)-2-methyl-3-azetidinol oxalate [1:1]

A mixture of 126.4 g (0.72 mole) of diphenylmethylamine and 100 g (0.66 mole) of 3-bromo-1,2-epoxybutane in 300 ml of methanol was stirred while being protected from light for 96 hr, then heated at reflux for 30 hr as the color changed from pale yellow to deep amber. A sample was assayed by $^1$H-nmr and showed 3 methyl doublets. A fine beige precipitate was removed by filtration (diphenylmethylamine hydrobromide) and the filtrate concentrated on a rotary evaporator to yield 174.6 g of crude oil. A 1.5 g sample was neutralized and placed on a 4 mm thick plate of a Chromatotron ® and eluted with 10% ethyl acetate-toluene. A total of sixteen fractions were collected which consisted of 6 distinct spots by TLC. The major component separated was 700 mg and appeared to be the trans isomer. This sample was converted to the oxalate salt. The main concentrate was converted to the free base with ammonium hydroxide and extracted into toluene which was dried over magnesium sulfate and concentrated. The reaction residue was dissolved in methanol and treated with 58 g of oxalic acid, heated to give a homogenous solution and allowed to cool after seeding with a sample of the trans oxalate salt. Filtration yielded 62 g of white granular product, m.p. 147°-148.5° C. A second crop of 26 g was also obtained. The $^1$H-nmr spectrum showed only a single $CH_3$ doublet with j ($CH_3$-H) of 6.1 Hz which is consistent with the trans compound.* Total yield of title compound was 88 g (38.8%).

*Robert H. Higgins and Norman H. Cromwell, J. Hetero. Chem. 8 (6), 1059-62 (1971).

Analysis: Calculated for $C_{17}H_{19}NO \cdot C_2H_2O_4$: C,66.46; H,6.16; N,4.08. Found: C,66.38; H,6.16; N,4.07.

PREPARATION 2

1-(Diphenylmethyl)-3-azetidinol methanesulfonate (ester) hydrochloride [1:1]

A mixture of 60.02 g (0.22 mole) of 1-diphenylmethyl-3-azetidinol hydrochloride and 48.94 g (0.484 mole) of triethylamine in 800 ml of toluene was stirred for 24 hr, then cooled to 5° C. in an ice bath and treated with 27.7 g (0.24 mole) of methanesulfonyl chloride added at a rate which maintained the temperature below 15° C. The reaction mixture was stirred for 3 hr and filtered to remove the triethylamine hydrochloride. The filtrate was treated with 40 g (0.242 mole) of 4-trifluoromethylphenol followed by 19.35 g (0.484 mole) of sodium hydroxide and 1.6 g (0.005 mole) of tetrabutylammonium bromide in 60 ml of water. The reaction mixture was stirred rapidly at reflux for 18 hrs, then stirred for 72 hr while it cooled to ambient temperature. The reaction mixture was transferred to a separatory funnel and washed with 4×200 ml of water (emulsion). The toluene phase was dried over magnesium sulfate and concentrated in vacuo to 82 g of oil. This residue was dissolved in 200 ml of isopropyl alcohol and treated with 20 ml of concentrated hydrochloric acid. Upon cooling, a solid separated and was removed by filtration (5.1 g). The filtrate was treated with isopropyl ether to give an oil which was worked up later. The solid was identified by spectral analysis as the methylsulfonate of the starting azetidinol. Recrystallization from isopropyl alcohol gave 3.3 g of fine white crystalline material, m.p. 172°-173° C., (shrinks 167° C.).

Analysis: Calculated for $C_{17}H_{19}NO_3S.HCl$: C,57.70; H,5.70; N,3.96. Found: C,57.80; H,5.86; N,3.92.

PREPARATION 3 trans-1-(Diphenylmethyl)-2-methyl-3-[3-(trifluoromethyl)phenoxy]azetidine oxalate [1:1]

A stirred slurry of 1.2 g (0.03 mole) of sodium hydride (60% dispersion in mineral oil) in 50 ml of dry DMF was treated with 3.45 g (0.01 mole) of trans-1-diphenylmethyl-2-methylazetidin-3-ol oxalate added in small portions. When the addition was complete and the evolution of hydrogen ceased, the reaction was heated to 80° C. for 2 hr then 1.64 g (0.01 mole) of 3-fluoro-trifluoromethylbenzene was added dropwise. The reaction mixture was stirred at 80° C. for an additional 18 hr. The reaction mixture was diluted with ice water and extracted with 3×25 ml of toluene. The extracts were combined, dried over magnesium sulfate, filtered, and the filtrate treated with 1 g of oxalic acid. The resulting solid was collected by filtration. Recrystallization from acetone-isopropyl ether yielded 2.2 g (4.5%) of fine white crystals, m.p. 146°-147° C. Proton NMR shows it to be the trans compound.

Analysis: Calculated for $C_{24}H_{22}F_3NO.C_2H_2O_4$: C,64.06; H,4.96; N,2.87. Found: C,64.26; H,4.99; N,2.89.

PREPARATION 4 trans-2-Methyl-3-[3-(trifluoromethyl)phenoxy]azetidine oxalate [1:1]

A methanol-warm water solution of 33 g (0.068 mole) of trans-1-diphenylmethyl-2-methyl-3-[3-(trifluoromethyl)phenoxy]azetidine oxalate was treated with ammonium hydroxide until basic, then extracted with 4×150 ml of methylene chloride. The combined methylene chloride extracts were washed with water, dried over magnesium sulfate, and concentrated in vacuo to a pale yellow oil. This oil was dissolved in 200 ml of 190 ethanol plus 5 ml of triethylamine and hydrogenated on a Parr apparatus with 3.3 g of 5% palladium-on-charcoal catalyst with a 40 psi atmosphere of hydrogen at 70° C. for 12 hr. After the calculated amount of hydrogen had been absorbed, the catalyst was removed by filtration and the filtrate concentrated in vacuo to yield 26.73 g of crude product. An 8 g portion was converted to the oxalate salt in isopropyl alcohol yielding 6.1 g of fine white powder; m.p. 155°-156° C. Total yield extrapolated from the aliquot converted to the oxalate salt was 84% of theory.

Analysis: Calculated for $C_{11}H_{12}F_3NO.C_2H_2O_4$: C,48.61; H,4.39; N,4.36. Found: C,48.67; H,4.38; N,4.34.

PREPARATION 5 trans-1-(Diphenylmethyl)-2-methyl-3-azetidinol methanesulfonate (ester) hydrochloride [1:1]

A solution of 6 g (0.025 mole) of trans-1-diphenylmethyl-2-methylazetidin-3-ol (obtained from the hydrochloride salt by partitioning in organic solvent and aqueous base, separating and evaporating the organic phase) in 40 ml of dry benzene was treated with 10 ml of triethylamine and cooled to 5° C. While stirring, the reaction mixture was treated with 3.54 g (0.03 mole) of methanesulfonyl chloride at a rate to control the temperature below 10° C. After stirring for 3 hr, TLC (20% ethyl acetate/methylene chloride on silica gel) showed the reaction to be incomplete. An additional 1.14 g (0.01 mole) of methanesulfonyl chloride was added and stirring continued for 1 hr. The reaction mixture was diluted with 100 ml of water and the benzene layer separated, washed with 300 ml of water, dried over magnesium sulfate and concentrated to an oil. The oil was dissolved in isopropyl ether and treated with ethereal hydrogen chloride. The solid salt was removed and recrystallized from 190 ethanol to give 3.4 g (37%) of fluffy white crystals, m.p. 152°-153° C.

Analysis: Calculated for $C_{18}H_{21}NO_3S.HCl$: C,58.77; H,6.03; N,3.81. Found: C,58.68; H,6.08; N,3.80.

PREPARATION 6

1-(Diphenylmethyl)-3-[3-(trifluoromethyl)phenoxy]azetidine

N-Diphenylmethyl-3-hydroxyazetidine hydrochloride (I) was prepared from benzhydrylamine and epichlorohydrin according to Anderson and Lok, J. Org. Chem., 37:3953 (1972). I (41.33 g, 0.15 mole) and triethylamine (42 ml, 0.30 mole) were stirred in toluene (250 ml) while methane sulfonylchloride (12 ml, 0.15 m) was added dropwise over 10 minutes with stirring and the temperature was maintained between 4° and 12° C. TLC (silica gel, 10% ethyl acetate in methylene chloride) at one hour showed all starting materials had reacted. The mixture was filtered to remove the triethylamine hydrochloride which was rinsed twice with toluene. The filtrate and washings combined to about 450 ml of solution. To this solution was added m-trifluoromethylphenol (27.5 g, 0.17 mole), tetrabutyl ammonium bromide (2.4 g), 50% sodium hydroxide (24 g, 0.3 mole) and water (24 ml) and the mixture was stirred vigorously and heated to reflux under nitrogen for 2.5 hr. The toluene layer of the mixture was separated and washed once with water, dried over sodium sulfate and evaporated to an oil. This oil was seeded and pumped on an oil pump overnight. A solid cake weighing 49.7 g was obtained. Some of this solid was dissolved in isopropanol with brief heating. Water was then added to cause slight cloudiness. The mixture was seeded and cooled to cause crystallization. The white solid was collected by filtration, washed with 50% aqueous isopropanol, and dried under vacuum overnight. Proton NMR showed slight contamination by silicone oil, m.p. 82.5°-84° C.

Analysis: Calculated for $C_{23}H_{20}F_3NO$: C,72.05; H,5.26; N,3.65. Found: C,71.62; H,5.29; N,3.61.

PREPARATION 7

3-(3-Fluorophenoxy)azetidine oxalate [1:1]

A mixture of 55.1 g (0.2 mole) of 1-diphenylmethyl-3-azetidinol hydrochloride [1:1] (prepared by the Method of Andersen and Lok, J. Org. Chem. 37: 3953 (1972)) and 50.5 g (0.5 mole) of triethylamine in 1.2 liters of toluene was stirred at ambient temperature under a nitrogen atmosphere for 5 hr, then cooled to 5° C. in an ice water bath and methanesulfonyl chloride added dropwise with stirring. The reaction mixture was allowed to warm to ambient temperature while stirring for approximately 18 hr.

The reaction mixture was diluted with 600 ml of isopropyl ether and the solid removed by filtration. The filtrate was then treated with 22.5 g (0.2 mole) of 3-fluorophenol and 24 g (0.6 mole) of sodium in 50 ml of water. Tetrabutylammonium bromide, 1 gm, was added to the reaction mixture and the reaction mixture was stirred rapidly and heated at reflux for approximately 16 hr.

The toluene layer was separated and washed with water twice (200 ml×2). Then while stirring, 20 g (0.22 mole) of oxalic acid was added as a solution in 100 ml of isopropyl alcohol and the mixture was allowed to stir for approximately 16 hr. Filtration yielded 61.6 g of white granular solid 1-diphenylmethyl-3-(3-fluorophenoxy)azetidine oxalate.

A slurry of 55 g of this white granular solid in 350 ml of ethanol was treated with 5.5 g (10% w/w) of 20% palladium hydroxide on carbon under nitrogen atmosphere and hydrogenated on a Parr apparatus at 70° C. with an initial hydrogen pressure of 45 psi for 18 hr. The hydrogen uptake could not be obtained since some leakage had occurred. The product was an insoluble solid which had to be converted to the free base in warm water with potassium carbonate. This mixture was stirred with chloroform and then filtered through Celite ® to remove the catalyst. The chloroform portion was separated and the aqueous basic solution extracted with 400 ml of chloroform. The chloroform portions were combined, dried over magnesium sulfate and concentrated on a rotary evaporator to yield 36.45 g of oil. The oil was dissolved in ethanol and treated with 10 g of oxalic acid, yielding 15.5 g (46.4%) of crude title compound. A sample was recrystallized from ethanol, m.p. 170°–171° C.

Analysis: Calculated for $C_9H_{10}FNO.C_2H_2O$: C,51.37; H,4.70; N,5.45. Found: C,51.41; H,4.72; N,5.47.

PREPARATION 8

1-(Diphenylmethyl)-3-(4-fluorophenoxy)azetidine oxalate [1:1]

A slurry of 22 g (0.55 mole) of sodium hydride (60% in mineral oil) in 200 ml of dry dimethylformamide was stirred at 50° C. under nitrogen atmosphere and treated with 119.7 g (0.5 mole) of 1-diphenylmethyl-3-azetidinol in 360 ml of dry dimethylformamide at a rate which maintained a steady evolution of hydrogen and maintained a temperature between 70°–80° C. After the addition was complete, the reaction mixture was heated to 90° C. and stirred for 1 hr then treated with 59.9 g (0.55 mole) of 1,4-difluorobenzene and stirred at 90° C. for an additional 32 hr. After cooling to ambient temperature, the reaction mixture was diluted with 4 liters of water and extracted with 4×1000 ml of toluene.* The toluene extracts were combined, dried over magnesium sulfate and concentrated in vacuo, yielding 155.9 g of amber oil. A second extraction with 4×200 ml of methylene chloride yielded, after concentration, an additional 20 g of yellow oil. These oils were combined, dissolved in 1 liter of 60% ethyl acetate/toluene, then treated with 150 g of silica gel and stirred for 3 hr. This mixture was filtered and the silica gel washed with 500 ml of 60% ethyl acetate/toluene. The combined effluents were treated with 45.5 g of oxalic acid (0.5 mole) and stirred for 18 hr. The solvent was decanted from the partially crystalline residue. This crude residue was recrystallized from isopropanol to yield 149.3 g (70.1%) of product as the oxalate salt. A sample was recrystallized for elemental analysis from ethanol, m.p. 162°–163° C.

*During the first extraction, the mixture had to be filtered to break up an emulsion which formed.

Analysis: Calculated for $C_{22}H_{20}FNO.C_2H_2O_4$ C,68.08; H,5.24; N,3.31. Found C,67.96; H,5.33; N,3.32.

PREPARATION 9

3-(3,4-Dichlorophenoxy)-1-(diphenylmethyl)azetidine

A mixture of 48 g (0.2 mole) of 1-diphenylmethyl-3-azetidinol and 22 g (0.22 mole) of triethylamine in 800 ml of toluene was stirred in a water bath while 27.5 g (0.22 mole) of methanesulfonyl chloride was added dropwise and stirring was continued for 18 hr. The reaction mixture was treated with 400 ml of isopropyl ether then filtered. The filter cake was washed with 2×150 ml of 50/50 isopropyl ether and toluene. The combined filtrates were treated with 32.6 g (0.2 mole) of 3,4-dichlorophenol, 100 mg of tetrabutylammonium bromide and 24 g (0.6 mole) of sodium hydroxide in 100 ml of water. This mixture was stirred vigorously at reflux for 16 hr. The basic aqueous portion was separated and the organic portion washed with water, dried over magnesium sulfate then concentrated to a solid residue, 74.5 g. Several recrystallizations from ethanol-water gave a product which was contaminated with starting azetidinol. Therefore, the material, 57.4 g, was dissolved in toluene and treated with silica gel. After stirring for 6 hr, the silica gel was removed by filtration and washed with 50/50 ethyl acetate and toluene. The filtratrs were concentrated to yield 45.9 g (59.7%) of pure product. A sample for elemental analysis was recrystallized from ethanol, m.p. 114°–115° C.

Analysis: Calculated for $C_{22}H_{19}Cl_2NO$: C,68.76; H,4.98; N,3.65. Found: C,68.73; H,5.00; N,3.65.

PREPARATION 10

3-(4-Chlorophenoxy)-1-(diphenylmethyl)azetidine

A stirred slurry of 41.3 g (1.03 mole) of 60% sodium hydride (in mineral oil) in 500 ml of dry dimethylformamide under nitrogen atmosphere was heated to 50° C. and 22.5 g (0.94 mole) of 1-diphenylmethyl-3-azetidinol in 700 ml of dry dimethylformamide was added dropwise at a rate which maintained the temperature between 70°–80° C. and allowed a gentle evolution of hydrogen. After the addition was complete, the reaction mixture was stirred for 2 hr at 90° C., then 125 g (0.94 mole) of 1-chloro-4-fluorobenzene was added dropwise. The reaction mixture was stirred at 90° C. under nitrogen for 24 hr, then stirred an additional 24 hr while the reaction mixture cooled to ambient temperature. The reaction mixture was poured into 6 liter of ice water and the solid which formed was collected by filtration to yield 271 g of wet crude product. A sample was recrystallized for elemental analysis from ethanol, yielding a fine tan crystalline product in 82.4% yield, m.p. 113°–114° C.

Analysis: Calculated for $C_{22}H_{20}ClNO$: C,75.53; H,5.76; N,4.00. Found: C,75.58; H,5.72; N,3.97.

PREPARATION 11

3-(3-Bromophenoxy)-1-(diphenylmethyl)azetidine oxalate [1:1]

A stirred slurry of 13.2 g (0.33 mole) of sodium hydride (60% dispersion in mineral oil) in 100 ml of dry dimethylformamide under nitrogen atmosphere was heated to 50° C. and 71.8 g (0.3 mole) of 1-diphenylmethyl-3-azetidinol in 300 ml of dry dimethylformamide was added at a rate which maintained the temperature between 70°–80° C. and a steady evolution of hydrogen. After the addition, the reaction mixture was stirred at 90° C. for 2 hr, then 57.8 g (0.315 mole) of 3-bromofluorobenzene was added all at once. The reaction mixture became exothermic as the temperature quickly reached 133° C. The reaction mixture was stirred for 4 hr as it cooled to 90° C. then heated at 90° C. for 12 hr and allowed to cool for the next 34 hr. The reaction mixture was poured into ice water and the oil which separated was extracted into 800 ml of toluene. The aqueous phase was extracted with 3×500 ml of toluene and the toluene extracts were combined, washed with 100 ml of water, and dried over magnesium sulfate and filtered. The filtrate was treated with 27 g of oxalic acid in 100 ml of isopropanol and stirred for 24 hr. Since no solid salt formed, the mixture was concentrated in vacuo and the amber residue washed with petroleum ether to remove mineral oil. Upon standing, the 109 g of amber oil solidified. A sample was recrystallized from absolute ethanol, yielding fine cotton-like white crystals, m.p. 146°–147° C.

Analysis: Calculated for $C_{22}H_{20}BrNO \cdot C_2H_2O_4$: C,59.52; H,4.58; N,2.89. Found: C,59.33; H,4.65; N,3.00.
*The main bulk of the material had approximately 20% of starting azetidinol present. The mixture of salts was converted to the free base and treated with 200 g of silica gel in toluene. The silica gel was removed by filtration and washed with 500 ml of 50/50 toluene/ethyl acetate. The filtration yielded, upon concentration, 59.4 g (63.3%) of yellow oil which contained a trace of starting azetidinol by TLC.

PREPARATION 12

1-(Diphenylmethyl)-3-(3-methoxyphenoxy)azetidine oxalate [1:1]

A stirred mixture of 48 g (0.2 mole) of 1-diphenylmethyl-3-azetidinol and 22 g (0.22 mole) of triethylamine in 800 ml of toluene was cooled in a water bath while 27.5 g (0.22 mole) of methanesulfonyl chloride was added dropwise. After stirring for 18 hr, the reaction mixture was treated with 200 ml of water to dissolve the triethylamine hydrochloride. The toluene portion was separated and washed with 2×200 ml of water and added to a solution of 24 g (0.6 mole) of sodium hydroxide in 100 ml of water. This mixture was stirred vigorously while 25 g (0.2 mole) of 3-methoxyphenol was added along with 100 ml of tetrabutylammonium bromide and then heated at reflux for 72 hr. After an additional 48 hr of stirring without heat, the basic portion was separated and the toluene portion washed with 3×100 ml of water, dried over magnesium sulfate, then concentrated in vacuo (64 g). Thin layer chromatography (20% ethyl acetate-toluene on silica gel) showed approximately 30% starting azetidinol present. The crude material was placed on a 1200 g silica gel column and eluted with toluene until the material at the solvent front came off the column. The elution solvent was changed to an ethyl acetate-toluene gradient ranging from 2–40% ethyl acetate. Most of the material came off between 5–20% ethyl acetate. A total of nine fractions were shown to be usable by TLC and combined and concentrated in vacuo, to give 49.64 g of oil (71.8%). A portion of this oil was converted to the oxalate salt in acetone/isopropyl ether and recrystallized from methylisobutyl ketone, yielding fine white crystals, m.p. 133°–134° C.

Analysis: Calculated for $C_{23}H_{23}NO_2 \cdot C_2H_2O_4$: C,68.95; H,5.78; N,3.22. Found: C,68.81; H,5.80; N,3.19.

PREPARATION 13

3-(4-Bromophenoxy)-1-(diphenylmethyl)azetidine

A stirred slurry of 8.8 g (0.22 mole) of 60% sodium hydride (mineral oil suspension) in 200 ml of dry dimethylformamide was heated under nitrogen atmosphere to 70° C. then 48 g (0.2 mole) of 1-diphenylmethyl-3-azetidinol in 150 ml of dry dimethylformamide was added dropwise at a rate which maintained the temperature below 90° C. and allowed a steady hydrogen evolution. The reaction mixture was stirred for 1 hr at 90° C., treated with 38.5 g (0.22 mole) of 4-bromofluorobenzene and heated at 90° C. for 36 hr. The reaction mixture was diluted with 1200 ml of water and after stirring for 3 hr, the solid precipitate was collected by filtration to yield 112 g of crude, wet product. Recrystallization from ligroin yielded 65.6 g (83.2%) of white crystals, m.p. 116°–117° C.

Analysis: Calculated for $C_{22}H_{20}BrNO$: C,67.01; H,5.11; N,3.55. Found: C,67.13; H,5.12; N,3.55.

PREPARATION 14

1-(Diphenylmethyl)-3-(3-methylphenoxy)azetidine

A stirred mixture of 48 g (0.2 mole) of 1-diphenylmethyl-3-azetidinol and 22 g (0.22 mole) of triethylamine in 800 ml of toluene under nitrogen was cooled in a water bath while 27.5 g (0.22 mole) of methanesulfonyl chloride was added dropwise. After stirring for 20 hr, the reaction mixture was treated with 200 ml of water to dissolve the triethylamine hydrochloride. The aqueous phase was separated and the toluene phase was washed with 2×100 ml water. The toluene solution was added to a mixture of 22.8 g (0.2 mole) of 3-methylphenol (95%), 24 g (0.6 mole) of sodium hydroxide and 100 mg of tetrabutylammonium bromide in 100 ml of water and the mixture was heated at reflux and stirred vigorously for 42 hr.

The reaction mixture was cooled to ambient temperature and the basic phase separated. The toluene phase was washed with 3×100 ml of water, dried over magnesium sulfate and concentrated in vacuo to yield an amber residue, 89.7 g. The residue was dissolved in 100 ml of toluene, placed on a 900 g silica gel column and eluted with toluene until product appeared, the elution solvent was changed to 10% ethyl acetate in toluene and elution continued until no more product was detected. Fractions containing product were combined and concentrated in vacuo to yield 30.55 g of pale yellow oil, which slowly solidified on standing and was recrystallized from hexane at freezer temperature to yield 19.8 g (30.1%) of fine white crystals, m.p. 68°–70° C.

Analysis: Calculated for $C_{23}H_{23}NO$: C,83.86; H,7.04; N,4.25. Found: C,84.14; H,7.00; N,4.25.

PREPARATION 15

3-(4-Chlorophenoxy)-1-azetidinecarbonyl chloride

A solution of 32.34 g (0.33 mole) of phosgene in 200 ml of methylene chloride cooled with a tap water bath was treated with 45.5 g (0.33 mole) of potassium carbonate and stirred for 30 min, then 105 g (0.3 mole) of 3-(4-chlorophenoxy)-1-diphenylmethylazetidine in 600 ml of methylene chloride was added dropwise. After stirring for an additional 18 hr, the reaction mixture was filtered to remove the inorganic salts then concentrated in vacuo to a dark oily residue, 127.7 g. A solid formed upon standing which was triturated with boiling 30/60 petroleum ether 3 times to remove diphenylmethyl chloride. The residue, 33 g of dark brown crystalline material, was mainly starting material. Upon standing, a white crystalline material separated from the petroleum ether triturates (4.4 g, m.p. 78°-80° C.). The triturates were concentrated in vacuo, yielding 31 g of pale yellow tacky crystals. Trituration of these crystals with isopropyl ether yielded 21.9 g (35.6%) of pale yellow crystalline product.

Analysis: Calculated for $C_{10}H_9Cl_2NO_2$: C,48.81; H,3.69; N,5.69. Found: C,49.10; H,3.61; N,5.63.

PREPARATION 16

3-(3-Bromophenoxy)-1-azetidinecarbonyl chloride

A solution of 22.7 g (0.23 mole) of phosgene in 200 ml of methylene chloride was treated with 29 g (0.23 mole) of potassium carbonate, stirred for 30 min, then 75.4 g (0.19 mole) of 3-(3-bromophenoxy)-1-diphenylmethylazetidine in 150 ml of methylene chloride was added dropwise. After stirring for 5 hr, the inorganic salts were removed by filtration and the filtrate was washed with water to destroy excess phosgene. Concentration (after drying) in vacuo yielded 96.85 g of oily residue. Trituration of the residue with isopropyl ether yielded 42 g of crude tan-gray product. A sample for analysis was recrystallized from isopropyl ether, m.p. 87°-88° C.

Analysis: Calculated for $C_{10}H_9BrClNO_2$: C,41.34; H,3.12; N,4.82. Found: C,41.12; H,3.14; N,4.78.

PREPARATION 17

3-(4-Bromophenoxy)-1-azetidinecarbonyl chloride

A stirred solution of 18.8 g (0.192 mole) of phosgene in 100 ml of methylene chloride was cooled to 15° C. in a water bath, then treated with 26.5 g (0.192 mole) of potassium carbonate. After stirring for 30 min, 63 g (0.16 mole) of 3-(4-bromophenoxy)-1-diphenylmethylazetidine in 180 ml of methylene chloride was added dropwise and stirring continued for 18 hr. The reaction mixture was diluted with ice water to dissolve the inorganic salts, the aqueous portion was separated and the organic phase washed with 25 ml of ice water. After separation, the methylene chloride solution was dried with magnesium sulfate, then concentrated in vacuo to a viscous yellow oil. Trituration of the residue with 30/60 petroleum ether yielded a crystalline product, 76.9 g, which was recrystallized from isopropyl ether-ligroin (50-50) to yield 34.8 g (74.8%) of white granular crystals, m.p. 77°-78° C.

Analysis: Calculated for $C_{10}H_9BrClNO_2$: C,41.34; H,3.12; N,4.82. Found: C,41.32; H,3.11; N,4.80.

PREPARATION 18

3-(3,4-Dichlorophenoxy)-1-azetidinecarbonyl chloride

A solution of 14 g (0.144 mole) of phosgene in 200 ml of methylene chloride was treated with 19.9 g (0.144 mole) of anhydrous potassium carbonate and stirred for 1 hr, then 45.9 g (0.12 mole) of 1-diphenylmethyl-3-(3,4-dichlorophenoxy)azetidine in 100 ml of methylene chloride was added dropwise and stirring was continued for 72 hr. The reaction mixture was filtered to remove the inorganic salts and then concentrated in vacuo to a pale yellow oil (67 g). Trituration of the residue with cyclohexane yielded a crude pale yellow solid (23.6 g). The filtrate was treated with ligroin and upon standing, an additional 13.3 g of tacky material was obtained. After several recrystallizations from cyclohexane to remove traces of diphenylmethyl chloride a portion was obtained as fine white crystals, in 70.1% yield, m.p. 96°-99° C.

Analysis: Calculated for $C_{10}H_{18}Cl_3NO_2$: C,42.81; H,2.87; N,4.99. Found: C,43.32; H,2.89; N,4.99.

PREPARATION 19

3-(4-Fluorophenoxy)-1-azetidinecarbonyl chloride

A solution of 52.09 g (0.527 mole) of phosgene in 500 ml of methylene chloride was stirred with 73 g (0.53 mole) of potassium carbonate under nitrogen atmosphere for 30 min, then treated with 146.3 g (0.439 mole) of 1-diphenylmethyl-3-(4-fluorophenoxy)azetidine in 300 ml of methylene chloride added dropwise. After stirring for 18 hr, the reaction mixture was treated with 200 ml of water added slowly. The aqueous phase was separated and the organic solution dried by filtration through Whatman phase separating filter paper then concentrated in vacuo to a pale amber oil. Trituration of the oil with 30/60 petroleum ether yielded a crude tacky solid, 89.3 g (88.6%). A portion of this solid was recrystallized from 30/60 petroleum ether yielding a fine white crystalline product, m.p. 44°-52° C. A second recrystallization from isopropyl ether yielded fine white crystals, m.p. 57°-58.5° C.

Analysis: Calculated for $C_{10}H_9ClFNO_2$: C,52.30; H,3.95; N,6.10. Found: C,52.42; H,3.91; N,6.08.

PREPARATION 20

3-Phenoxyazetidine oxalate

The title compound is prepared by a procedure similar to that used in Example 1 of U.S. Pat. No. 4,379,151 to produce 3-phenoxyazetidinemethanesulfate. A solution of 1-diphenylmethyl-3-phenoxyazetidine in ethanol is treated with 20% palladium hydroxide on carbon and hydrogenaged for approximately 24 hr at about 45 psi and 80° C. The mixture is filtered and filtrate concentrated. The residue is diluted with ethanol and treated with oxalic acid, and the title compound recrystallized from methanol.

PREPARATION 21

1-(1-Phenylethyl)-3-azetidinol maleate [1:1]

A solution of 60.59 g (0.5 mole) of α-phenethylamine and 46.27 g (0.5 mole) of epichlorohydrin in 200 ml of methanol was allowed to stand protected from light for 96 hr. The reaction mixture was then stirred at reflux for 72 hr and the solvent removed in vacuo. Trituration of the oil residue with isopropyl ether gave some white crystalline product (α-phenethylamine hydrochloride) which was removed by filtration. The crude product solution was converted to the free base by adding ammonium hydroxide and extracting with 4×200 ml of toluene. The toluene extracts were combined, dried over magnesium sulfate and filtered. The filtrate was treated with 58 g of maleic acid dissolved in 800 ml of methylisobutyl ketone. The crude product was collected in 3 fractions to yield a total of 62 g of maleate salt (42.4%). A sample was recrystallized from ethyl acetate for analysis purposes, m.p. 113°-114° C.

Analysis: Calculated for $C_{11}H_{15}NO.C_4H_4O_4$: C,61.42; H,6.53; N,4.78. Found: C,61.37; H,6.65; N,4.80.

PREPARATION 22

2-[1-(1-Phenylethyl)-3-azetidinyloxy]pyridine

The maleate salt of 1-(1-phenylethyl)-3-azetidinol (65 g, 0.22 mole) was partitioned between toluene and dilute sodium hydroxide and was extracted once with toluene. The organic layer was dried (sodium sulfate) and concentrated. The residue was dissolved in 125 ml of dimethylformamide and added dropwise to a stirred suspension of 9.6 g (0.24 mole) of sodium hydride (washed three times with isooctane) in 400 ml of dimethylformamide at 25°–35° C. The solution was heated to 65° C. and 35 g (0.22 mole) of 2-bromopyridine was added dropwise while heating to 75° C. The solution was stirred and heated at 90° C. for 1 hr followed by heating at 120° C. for 2.75 hr. The mixture was stirred at room temperature overnight and concentrated. The residue was partitioned between water and isopropyl ether. The organic layer was washed twice with water, dried (sodium sulfate), filtered and concentrated. Crude yield was 30 g. The residue was distilled to give 8 g of product, bp 128°–134° C./0.01 mm.

Analysis: Calculated for $C_{16}H_{18}N_2O$: C,75.57; H,7.13; N,11.01. Found: C,75.20; H,7.18; N,10.90.

PREPARATION 23

3-(3-Methoxyphenoxy)-1-azetidinecarbonyl chloride

Utilizing the procedure of Preparation 15 and reacting the following in sequence:
phosgene,
potassium carbonate, and
1-diphenylmethyl-3-(3-methoxyphenoxy)azetidine (free base obtained in Preparation 12),
the title compound is obtained.

PREPARATION 24

3-(3-Methylphenoxy)-1-azetidinecarbonyl chloride

Utilizing the procedure of Preparation 15 and reacting the following in sequence:
phosgene,
potassium carbonate, and
1-diphenylmethyl-3-(3-methylphenoxy)azetidine (free base obtained in Preparation 14),
the title compound is obtained.

PREPARATION 25

3-[(4-Chlorophenyl)thio]-1-(diphenylmethyl)azetidine

A stirred mixture of 48 g (0.2 mole) of 1-diphenylmethyl-3-azetidinol, and 22 g (28 ml) (0.22 mole) of triethylamine in 800 ml of toluene under nitrogen was cooled in a water bath then treated with 27.5 g (0.22 mole) of methanesulfonyl chloride added dropwise. After stirring for 16 hr, the reaction mixture was diluted by adding 200 ml of isopropyl ether. The triethylamine hydrochloride was removed by filtration and washed with 200 ml of (50/50) toluene/isopropyl ether. The filtrates were combined, washed with 2×200 ml of water and returned to the reaction mixture. The reaction mixture was treated with 24 g (0.6 mole) of sodium hydroxide in 100 ml of water, 6.5 g (0.02 mole) of tetrabutylammonium bromide and 31.8 g (0.22 mole) of 4-chlorothiophenol then heated at reflux while stirring vigorously. After 96 hr, TLC showed the expected product to be approximately 80% of the reaction mixture. After cooling, the organic phase was separated, washed with water (3×200 ml) and treated with 25 g of oxalic acid dihydrate in 100 ml of methanol. The precipitated product was collected by filtration, yielding 75 g of crude oxalate salt. The oxalate salt was suspended in warm water and treated with 0.4 mole (26 g) of potassium hydroxide. The solid which precipitated from the basic solution was collected and recrystallized from methanol with charcoal treatment to yield 17.6 g of white granular crystals, m.p. 84°–86° C. A second crop of crystals was obtained from the filtrate after standing (8.6 g). The yield was 36%.

Analysis: Calculated for $C_{22}H_{20}ClNS$: C,72.21; H,5.51; N,3.83. Found: C,72.17; H,5.53; N,3.89.

PREPARATION 26

3-[(4-Chlorophenyl)thio]-1-azetidinecarbonyl chloride

A stirred mixture of 8.5 g (0.086 mole) of phosgene and 12 g (0.086 mole) of potassium carbonate in 200 ml of methylene chloride was cooled in a water bath under nitrogen atmosphere while 26.3 g (0.072 mole) of 3-[(4-chlorophenyl)thio]-1-diphenylmethylazetidine in 100 ml of methylene chloride was added dropwise. After the addition, the reaction mixture was stirred for 20 hr then treated with enough ice to form a thick paste. The methylene chloride solution was decanted, filtered through Whatman phase separating paper and concentrated in vacuo. The residue (40 g) was triturated 3 times at −78° C. with 30/60 petroleum ether and allowed to warm to 0° C. before decanting the petroleum ether. The fine granular solid which remained was collected by filtration to yield 14.1 g (75%) of crude product. A sample was recrystallized from hexanes for analysis, m.p. 47°–48° C.

Analysis: Calculated for $C_{10}H_9Cl_2NOS$: C,45.82; H,3.46; N,5.34. Found: C,45.78; H,3.40; N,5.37.

PREPARATION 27

Cis-1-(Diphenylmethyl)-2-methyl-3-[3-(trifluoromethyl)phenoxy]azetidine fumarate [1:1]

A stirred slurry of 4.4 g (0.11 mole) of a 60% mineral oil dispersion of sodium hydride in 50 ml of dry dimethylformamide under nitrogen atmosphere was heated to 80° C. and treated with 25.3 g (0.1 mole) of 1-diphenylmethyl-2-methyl-3-azetidinol, cis isomer in 100 ml of dry dimethylformamide added dropwise at a rate that gave a smooth evolution of hydrogen and maintained the temperature at 80°–85° C. After the addition, the reaction mixture was stirred at 86°–88° C. for 2 hr then 18.1 g (0.11 mole) of 3-(trifluoromethyl)fluorobenzene was added all at once (exothermic to 106° C.). After 3.5 hr, TLC (20% ethyl acetate/toluene on silica gel) showed about 80% product had formed. The reaction mixture was treated with 30% additional sodium hydride and 10% additional 3-(trifluoromethyl)fluorobenzene. The reaction mixture was stirred an additional 7 hr at 86° C. and allowed to cool at ambient temperature while stirring approximately 18 hr. The reaction mixture was diluted with water and extracted with benzene (4×200 ml). The combined extracts were dried over magnesium sulfate then concentrated in vacuo (45.1 g). The crude product was chromatographed on a 1,200 g silica gel column by eluting with chloroform. The effluent fractions containing product were combined and concentrated in vacuo to yield 35.3 g of product (88.9%). A sample was treated with fumaric acid and crystallized from 2-propanol, m.p. 178°–180° C.

Analysis: Calculated for $C_{24}H_{22}F_3NO.C_4H_4O_4$: C,65.49; H,5.10; N,2.73. Found: C,65.58; H,5.16; N,2.73.

The following examples illustrate preparation of compounds encompassed by Formula I and useful in the method of treatment of the invention. The structures of the compounds are shown in Table I. The scope of the invention is not limited by the examples, however.

EXAMPLE 1

N-Methyl-3-[3-(trifluoromethyl)phenoxy]-1-azetidinecarbothioamide

Crude 3-[3-(trifluoromethyl)phenoxy]azetidine from catalytic debenzylation of 26.0 g (0.078 mole) of 1-benzhydryl-3-[3-(trifluoromethyl)phenoxy]azetidine was dissolved in 100 ml of methylene chloride and treated dropwise under a nitrogen atmosphere with a solution of 5.0 g (0.0678 mole) of methylisothiocyanate in 15 ml of methylene chloride. The reaction mixture was stirred for 16 hr at ambient temperature and let stand over the weekend. The solution was filtered through a celite filter pad to remove a fine crystalline precipitate and the filtrate was evaporated under reduced pressure. The residual oil was crystallized from isopropyl ether to give 12.6 g of product, m.p. 79°-86° C. A 5.0 g sample was recrystallized from isopropyl ether (charcoal) to give 3.2 g, m.p. 89°-93° C., which was shown by TLC on silica gel (10% methanol-toluene) to be contaminated by a lower $R_f$ material. The filtrate was evaporated under reduced pressure, combined with the 3.2 g of solid and dissolved in 100 ml of methylene chloride. The solution was stirred with 25 g of silica gel for 0.5 hr and filtered through a sintered glass filter. The silica gel was washed with a small volume of methylene chloride and the filtrate evaporated under reduced pressure. The residual solid was recrystallized from isopropyl ether to give 1.3 g of pure product, m.p. 96°-98° C.

Analysis: Calculated for $C_{12}H_{13}F_3N_2OS$: C,49.65; H,4.51; N,9.65. Found: C,49.58; H,4.48; N,9.58.

EXAMPLE 2

N-(2,6-Dimethylphenyl)-3-[3-(trifluoromethyl)phenoxy]-1-azetidinecarbothioamide

Crude 3-[3-(trifluoromethyl)phenoxy]azetidine from catalytic debenzylation of 30.0 g (0.078 mole) of 1-benzhydryl-3-[3-(trifluoromethyl)phenoxy]azetidine was dissolved in 100 ml of methylene chloride and treated dropwise under a nitrogen atmosphere with a solution of 12.7 g (0.078 mole) of 2,6-dimethylphenylisothiocyanate in 25 ml of methylene chloride. The product began to precipitate during the addition and an additional 50 ml of methylene chloride was added to facilitate stirring. After stirring overnight at ambient temperature, the product was collected by filtration (13.5 g, m.p. 196°-199° C.). A 6.0 g sample was recrystallized from isopropanol to give 5.3 g of product, m.p. 197°-199° C.

Analysis: Calculated for $C_{19}H_{19}F_3N_2OS$: C,59.99; H,5.03; N,7.36. Found: C,60.04; H,5.04; N,7.35.

EXAMPLE 3

N-(Phenylmethyl)-3-[3-(trifluoromethyl)phenoxy]-1-azetidinecarboxamide

To a stirred and chilled (10°-20° C.) solution of 0.04 mole of 3-[3-(trifluoromethyl)phenoxy]azetidine in 100 ml of methylene chloride was added dropwise 6.12 g (0.046 mole) of benzyl isocyanate. The reaction mixture was stirred at room temperature for 2 hr and was filtered. The filter cake was washed with petroleum ether (2×50 ml), dilute aqueous sodium bicarbonate (2×50 ml), and water (2×50 ml), yielding 12 g (86%). Recrystallization twice from ethyl acetate gave 9.0 g of clear white flakes, m.p. 173.5°-175° C.

Analysis: Calculated for $C_{18}H_{17}F_3N_2O_2$: C,61.71; H,4.89; N,8.00. Found: C,61.57; H,4.87; N,7.99.

EXAMPLE 4

N-(2,6-Dichlorophenyl)-3-[3-(trifluoromethyl)phenoxy]-1-azetidinecarbothioamide

A solution of 0.04 mole of 3-[3-(trifluoromethyl)phenoxy]azetidine in 100 ml of absolute ethanol was stirred in a tap water bath while 8.16 g (0.04 mole) of 2,6-dichlorophenyl isothiocyanate was added all at once. The reaction was slightly exothermic and as the isothiocyanate began to dissolve, product began to precipitate. After stirring for 45 minutes the reaction mixture was heated on a steam bath to assure that all the isothiocyanate dissolved, and upon cooling, filtration yielded 15.2 g of white crystalline product. A portion of this material (7.9 g) was recrystallized from absolute ethanol to give 4.3 g of pure crystalline powder, m.p. 196°-197° C.

Analysis: Calculated for $C_{17}H_{13}F_3Cl_2N_2OS$: C,48.47; H,3.11; N,6.65. Found: C,48.40; H,3.07; N,6.54.

EXAMPLE 5

N-[3-(Diethylamino)propyl]-3-[3-(trifluoromethyl)phenoxy]-1-azetidinecarbothioamide, oxalate [1:1]

A solution of (0.0584 mole) of 3-[3-(trifluoromethyl)phenoxy]azetidine was stirred at 10° C. while 10.66 g (0.0584 mole) of 3-(diethylamino)propyl isothiocyanate was added all at once. After stirring overnight at ambient temperature, the reaction mixture was concentrated at 50° C. on a rotary evaporator to a thick syrup residue. The residue was dissolved in isopropanol and treated with 5.3 g of oxalic acid, warmed on a steam bath to dissolve the acid, and upon cooling, a solid salt precipitated. An equal volume of isopropyl ether was added to ensure complete precipitation. Filtration gave 26 g of crude product. A portion (13 g) was recrystallized from isopropanol/methanol/isopropyl ether (100/50/50) (cooled in a refrigerator) to yield upon filtration 7.5 g of white product, m.p. 155°-157° C. Proton NMR confirmed that this was the expected product.

Analysis: Calculated for $C_{18}H_{26}F_3N_3O.C_2H_2O_4$: C,50.10; H,5.89; N,8.76. Found: C,50.02; H,5.97; N,8.89.

EXAMPLE 6

N-[3-(Dimethylamino)propyl]-3-[3-(trifluoromethyl)phenoxy]-1-azetidinecarbothioamide A stirred solution of 0.0584 mole of 3-[3-(trifluoromethyl)phenoxy]azetidine at 10° C. was treated with 8.42 g (0.0584 mole) of 3-(dimethylamino)propyl isothiocyanate all at once and allowed to stir at ambient temperature overnight. The reaction mixture was treated with 5.3 g (0.0584 mole) of oxalic acid and diluted with 200 ml of isopropyl ether which yielded only 3.8 g of product. The volume was reduced to 100 ml at 50° C. in vacuo and diluted with 500 ml of isopropyl ether to yield an additional 15.3 g of product. The combined solid material was dissolved in isopropyl alcohol and upon cooling, a fine precipitate formed (N,N-dimethyl-1,3-propanediamine oxalate) which was removed by filtration. The product failed to crystallize; addition of isopropyl ether gave only an amorphous gel. After trying to obtain a more satisfactory product for 3 weeks, the reaction material was converted to the free base and taken up in isopropyl ether. The ether solution was stirred with 300 ml of water overnight to remove the diamine. The product crystallized as the free base from the heterogenous mixture and was filtered to give 11.3 g of fine beige crystals. Rework of the filtrate gave an additional 2.3 g of product. A portion (8 g) was recrystallized from benzene/ligroin to yield 5.8 g of very fine beige crystals which were dried at 82° C. under vacuum, m.p. 107°-108° C.

Analysis: Calculated for $C_{16}H_{22}F_3N_3OS$: C,53.17; H,6.14; N,11.63. Found: C,53.29; H,6.15; N,11.60.

EXAMPLE 7

N-(2-Propenyl)-3-[3-(trifluoromethyl)phenoxy]-1-azetidinecarboxamide

A solution of 18.9 g (0.05 mole) of crude 3-[3-(trifluoromethyl)phenoxy]azetidine (contains an equal molar amount of diphenylmethane) in 100 ml of isopropyl ether was stirred under nitrogen while 4.16 g (0.05 mole) of 2-propenyl isocyanate was slowly added. The reaction mixture which was somewhat turbid, cleared and after 1 hr a fine crystalline precipitate began to form. After stirring for 18 hrs, the product was removed by filtration, washed with fresh isopropyl ether and air dried to yield 9.5 g of white crystals, m.p. 75°-76° C.

Analysis: Calculated for $C_{14}H_{15}F_3N_2O_2$: C,56.00; H,5.04; N,9.33. Found: C,55.98; H,5.05; N,9.31.

EXAMPLE 8

N-Cyclopropyl-3-[3-(trifluoromethyl)phenoxy]-1-azetidinecarboxamide

A mixture of 1.9 g (0.033 mole) of cyclopropylamine and 4.9 g of 1,1'-carbonyldiimidazole in 60 ml of tetrahydrofuran was stirred at ambient temperature for 1 hr. The clear solution which formed was treated with a solution of (0.03 mole) of 3-[3-(trifluoromethyl)phenoxy]azetidine in 20 ml of tetrahydrofuran. After stirring overnight, the solid precipitate was removed by filtration to give 4.4 g of gray-white powder. The CI mass spectrum showed a p+1 at 381 m/e which was consistent with the expected product. Recrystallization from benzene/ligroin gave 2.3 g of a light gray powder, m.p. 152°-153° C.

Analysis: Calculated for $C_{14}H_{15}F_3N_2O$: C,56.00; H,5.04; N,9.33. Found: C,55.97; H,5.07; N,9.28.

EXAMPLE 9

N-[3-(Diethylamino)propyl]-3-[3-(trifluoromethyl)phenoxy]-1-azetidinecarboxamide oxalate [1:1.5]

A mixture of 4.3 g (0.033 mole) of 3-diethylaminopropylamine and 4.9 g (0.033 mole) of 1,1'-carbonyldiimidazole in 60 ml of methylene chloride was stirred at ambient temperature for 1 hr. The resulting solution was treated with 3-[3-(trifluoromethyl)phenoxy]azetidine (obtained from 9.21 g (0.03 mole) of the oxalate salt) in 30 ml of methylene chloride. After stirring for 18 hr, the reaction mixture was transferred to a separatory funnel and washed with 3×20 ml of water, dried over magnesium sulfate and concentrated in vacuo to a dark oil. The residue (8 g) was chromatogarphed on a 150 g neutral alumina column by eluting with chloroform. Concentration of the initial fraction gave the product as an amber oil which was dissolved in methylisobutyl ketone and treated with 2 g of oxalic acid. Dilution with isopropyl ether gave an oil which solidified and was recrystallized from acetone/isopropyl ether to give 6.25 g (41%) of beige crystals, m.p. 91°-93° C.

Analysis: Calculated for $C_{18}H_{26}F_3N_3O_2 \cdot 1.5\ C_2H_2O_4$ C,49.61; H,5.75; N,8.26. Found: C,49.56; H,5.73; N,8.24.

EXAMPLE 10

N-(2-Propenyl)-3-[4-(trifluoromethyl)phenoxy]-1-azetidinecarboxamide

A solution of 8.7 g (0.04 mole) of crude 3-[4-(trifluoromethyl)phenoxy]azetidine in 75 ml of isopropyl ether was stirred under a blanket of nitrogen while 4.2 g (0.05 mole) of 2-propenyl isocyanate was added dropwise. After stirring for 3 days, no crystalline product precipitated. The reaction mixture was concentrated to a dark reddish oil. TLC (20% ethyl acetate/methylene chloride on silica gel) showed at least 6 spots, all well separated. The residue was dissolved in chloroform, chromatographed on a 350 g silica gel column and eluted with chloroform until the reddish forerun was removed. The column was then eluted with an ethyl acetate/chloroform gradient to 4% ethyl acetate. All the fractions were combined and concentrated to give 4.8 of orange oil, which crystallized on standing. Recrystallization from acetone/cyclohexane gave 3.3 g (27.5%) of beige crystals, m.p. 91°-92.5° C.

Analysis: Calculated for $C_{14}H_{15}F_3N_2O_2$: C,56.00; H,5.04; N,9.33. Found: C,55.98; H,5.17; N,9.36.

EXAMPLE 11

N-(Cyclopropylmethyl)-3-[3-(trifluoromethyl)phenoxy]-1-azetidinecarboxamide

A solution of 2.6 g (0.024 mole) of (aminomethyl) cyclopropane hydrochloride in 50 ml of pyridine was stirred under a blanket of nitrogen while 3.9 g (0.024 mole) of 1,1'-carbonyldiimidazole was added. After stirring for 45 minutes, the TLC (5% methanol/methylene chloride on silica gel) showed no reaction; therefore, 2 ml of triethylamine was added. The reaction mixture after 10 minutes became cloudy and the TLC showed a new product. The reaction was treated with 6.2 g (0.02 mole) of 3-(3-(trifluoromethyl)phenoxy]azetidine oxalate. After stirring for 1 hr, a sample was removed, and upon dilution with water, a solid precipitated. The CI mass spectrum indicated it was product. After 2 days, the reaction was diluted with 5 volumes of water and the resulting precipitate collected by filtration to yield 6.5 g of pale yellow crystalline product. Recrystallization from ethanol/water produced white plate-like crystals which were dried at 82° C. for 3 hr in a drying pistol under vacuum; weight of the product was 5.8 g (92%), m.p. 132°-133° C.

Analysis: Calculated for $C_{15}H_{17}F_3N_2O_2$: C,57.32; H,5.45; N,8.91. Found: C,57.22; H,5.44; N,8.86.

EXAMPLE 12

N,N-Diethyl-3-[3-(trifluoromethyl)phenoxy]-1-azetidinecarboxamide

A stirred slurry of 5 g (0.0163 mole) of 3-[3-(trifluoromethyl)phenoxy]azetidine oxalate in 50 ml of tetrahydrofuran was treated with 5 ml of triethylamine and after 1 hr, 2.5 g (0.018 mole) of diethylcarbamoyl chloride was added. After stirring an additional 15 hr, the reaction was treated with 10 ml of water and saturated with calcium chloride. The tetrahydrofuran was decanted from the solid residue and concentrated in vacuo to an oil. The crude oil was chromatographed on a Water's Prep-LC using 50% ethyl acetate/toluene as the eluent. After concentration of the main fractions 3.1 g (60.1%) of pale yellow oil was obtained.

Analysis: Calculated for $C_{15}H_{19}F_3N_2O_2$: C,56.96; H,6.05; N,8.86. Found: C,56.69; H,6.01; N,8.77.

EXAMPLE 13

N,N-Dimethyl-3-[3-(trifluoromethyl)phenoxy]-1-azetidinecarboxamide

A stirred slurry of 5 g (0.0163 mole) of 3-[3-(trifluoromethyl)phenoxy]azetidine oxalate in 50 ml of tetrahydrofuran was treated with 5 ml of triethylamine and after 1 hr, 1.95 g (0.018 mole) of dimethylcarbamoyl chloride was added. After stirring an additional 15 hr, the reaction mixture was treated with 20 ml of water and 10 g of calcium chloride. The tetrahydrofuran layer was decanted and the residue triturated with 20 ml of ethyl acetate, then decanted. The combined tetrahydrofuran and ethyl acetate solution was concentrated in vacuo. The crude residue was chromatographed on a Water's Prep-LC using 50% ethyl acetate/toluene as the eluent. After concentration of the main fractions, 3.6 g (76.6%) of pale yellow oil was obtained.

Analysis: Calculated for $C_{13}H_{15}F_3N_2O_2$: C,54.17; H,5.25; N,9.72. Found: C,53.73; H,5.20; N,9.60.

EXAMPLE 14

N-(2-Propynyl)-3-[3-(trifluoromethyl)phenoxy]-1-azetidinecarboxamide

A mixture of 3.9 g (0.024 mole) of 1,1'-carbonyldiimidazole and 1.32 g (0.024 mole) of 2-propynylamine in 50 ml of tetrahydrofuran was stirred at ambient temperature for 1 hr, then treated with 6.2 g of 3-[3-(trifluoromethyl)phenoxy]azetidine. The reaction mixture was treated with 3 ml of triethylamine and stirred for 18 hr. The reaction mixture was diluted with an equal volume of water and filtered to yield 8 g of wet product. Recrystallization from isopropyl ether gave 3.8 g of gray solid, a mixture of product and the symmetrical urea of starting 2-propynylamine. A second recrystallization from ethanol-water yielded 2.6 g (43.6%) of pure product, m.p. 105°–106° C.

Analysis: Calculated for $C_{14}H_{13}F_3N_2O_2$: C,56.38; H,4.39; N,9.39. Found: C,56.32; H,4.34; N,9.44.

EXAMPLE 15

N-Cyclohexyl-3-[3-(trifluoromethyl)phenoxy]-1-azetidinecarboxamide

A stirred mixture of 5 g (0.0163 mole) of 3-[3-(trifluoromethyl)phenoxy]azetidine oxalate and 2.04 g (0.018 mole) of cyclohexyl isocyanate in 50 ml of tetrahydrofuran was treated with 2 ml of triethylamine then stirred for 18 hr. Dilution of the mixture with water gave a solid precipitate which was collected by filtration to yield 12 g of crude product. Recrystallization from acetone/water gave 5 g of fine white crystals, m.p. 148°–150° C. TLC (ethyl acetate on silica gel) showed a trace of symmetrical cyclohexyl urea as well as the product. A second recrystallization from isopropanol yielded 1.65 g (29.6%) of white powder; dried under 0.5 mm/Hg vacuum, m.p. 153°–154° C.

Analysis: Calculated for $C_{17}H_{21}F_3N_2O_2$: C,59.64; H,6.18; N,8.18. Found: C,59.52; H,6.20; N,8.17.

EXAMPLE 16

N-Cyclopropyl-3-[4-(trifluoromethyl)phenoxy]-1-azetidinecarboxamide

A stirred slurry of 4.4 g (0.027 mole) of 1,1'-carbonyldiimidazole in 50 ml of methylene chloride under nitrogen was treated with 1.54 g (0.027 mole) of cyclopropylamine. After a short (2 min) induction period, the clear solution became suddenly exothermic, bringing the reaction to a gentle reflux. After 1 hr when the reaction mixture had cooled to ambient temperature, 9.6 g (0.025 mole) of 3-[4-(trifluoromethyl)phenoxy]azetidine, 56.66% purity (contains diphenylmethane) was added all at once and stirring continued for 18 hr. The reaction mixture was concentrated on a rotary evaporator to give a partially crystalline residue. The residue was partitioned between 30/60 petroleum ether and water and the resulting waxy solid removed by filtration. Recrystallization from isopropyl ether yielded 5.7 g (75.9%) of silver plate-like crystals, m.p. 145°–147° C. After drying at 80° C. under 0.5 mm/Hg vacuum, the weight was not diminished, m.p. 152°–153° C.

Analysis: Calculated for $C_{14}H_{15}F_3N_2O_2$: C,56.00; H,5.04; N,9.33. Found: C,55.77; H,4.98; N,9.44.

EXAMPLE 17

N-(Cyclopropylmethyl)-3-[4-(trifluoromethyl)phenoxy]-1-azetidinecarboxamide

A stirred mixture of 4.4 g (0.027 mole) of 1,1'-carbonyldiimidazole and 2.9 g (0.027 mole) of (aminoethyl)cyclopropane hydrochloride in 50 ml of methylene chloride was treated with the dropwise addition of 2.73 g (0.027 mole) of triethylamine. The reaction was exothermic. The mixture was cooled while stirring for 1 hr, then 9.6 g (0.025 mole) of 3-[4-(trifluoromethyl)phenoxy]azetidine, 56.66% purity (contains diphenylmethane) was added all at once and stirring continued for 18 hr. The reaction mixture was concentrated on a rotary evaporator to give an amber residue. Trituration of this residue with 30/60 petroleum ether gave only an insoluble oil. The trituration step was repeated with 2×20 ml of 30/60 petroleum ether and the residue treated with water to yield a white solid. The solid was recrystallized from isopropyl ether to yield 4.8 g (61.8%) of white platelike crystals; after during at 80° C. under 0.5 mm Hg vacuum, m.p. 132°–133° C.

Analysis: Calculated for $C_{15}H_{17}F_3N_2O_2$: C,57.32; H,5.45; N,8.91. Found: C,57.26; H,5.46; N,8.93.

EXAMPLE 18

N-[3-(Diethylamino)propyl]-3-[4-(trifluoromethyl)phenoxy]-1-azetidinecarbothioamide A stirred solution of 1.92 g (0.005 mole) of 3-[4-(trifluoromethyl)phenoxy]azetidine, 56.66% (contains diphenylmethane) in 20 ml of isopropyl ether was treated with 0.88 g (0.005 mole) of 3-(diethylamino)propyl isothiocyanate and stirred for 3.5 hr. The reaction mixture was treated with 0.5 g of oxalic acid dissolved in 2 ml of methanol. After stirring for 18 hr, the solid was collected by filtration, yielding 1.9 g of fine tan powder, m.p. 147°–150° C. The solid was dissolved in water and treated with dilute sodium hydroxide. An oil separated which solidified and was collected by filtration. Recrystallization from cyclohexane yielded 1.1 g (56.5%) of fine tan crystals, m.p. 109°–110° C.

Analysis: Calculated for $C_{18}H_{26}F_3N_3OS$: C,55.51; H,6.73; N,10.79. Found: C,55.68; H,6.67; N,10.73.

EXAMPLE 19

N-[3-(Diethylamino)propyl]-3-[4-(trifluoromethyl)-phenoxy]-1-azetidinecarboxamide oxalate [1:2]

A stirred solution of 4.4 g (0.027 mole) of 1,1'-carbonyldiimidazole in 50 ml of methylene chloride under nitrogen was treated with the dropwise addition of 3.52 g (0.027 mole) of 3-(diethylamino)propylamine. The reaction mixture was stirred for 1 hr as the somewhat exothermic reaction cooled to ambient temperature then treated with 9.6 g (0.025 mole) of 3-[4-(trifluoromethyl)phenoxy]azetidine, 56.66% (contains diphenylmethane) all at once. After stirring for 18 hr, the reaction mixture was concentrated on a rotary evaporator and the residue dissolved in toluene. The toluene solution was washed with 3×20 ml of water, then treated with 2.5 g of oxalic acid in 10 ml of isopropanol. The resulting solid was collected by filtration and triturated with boiling acetone. After filtration, 1.8 g of unidentified fine white precipitate formed which was separated by filtration. The acetone solution was concentrated to a solid which was recrystallized from isopropyl alcohol/isopropyl ether to yield 9.2 g of crude product (4 spots on TLC; 10% methanol/methylene chloride on silica gel). Recrystallization from methyl ethyl ketone yielded 6.8 g (49.1%) of fine white powder, m.p. 129°-130° C.

Analysis: Calculated for $C_{18}H_{26}F_3N_3O_2 \cdot 2C_2H_2O_4$: C,47.74; H,5.46; N,7.59. Found: C,47.82; H,5.68; N,7.76.

EXAMPLE 20

N-(2-Propynyl)-3-[4-(trifluoromethyl)phenoxy]-1-azetidinecarboxamide

A solution of 4.4 g (0.027 mole) 1,1'-carbonyldiimidazole in 50 ml of tetrahydrofuran was stirred under nitrogen while 1.49 g (0.027 mole) of 2-propynylamine was added with a syringe and needle through a septum installed in one neck of the reaction flask. After stirring for 2 hr, 9.6 g (0.025 mole) of 3-[4-(trifluoromethyl)phenoxy]azetidine (56.66% purity; contains diphenylmethane) was added all at once and stirring continued for an additional 18 hr. The reaction mixture was diluted with ice-water and extracted with 30/60 petroleum ether to remove the diphenylmethane. The oily aqueous portion was extracted with 4×50 ml of methylene chloride. These extracts were combined, dried over sodium sulfate and concentrated to an amber oil on a rotary evaporator. The oil solidified when triturated with a small amount of isopropyl ether (50 ml). Filtration yielded 6.1 g of rose-tinted solid product. TLC (10% methanol/methylene chloride on silica gel) showed a mixture of 3 products and some starting material. Recrystallization from ethanol/water gave the product in several small fractions. These were combined and recrystallized from isopropyl ether to yield 4.1 g of pale beige powder, m.p. 135°-137° C. TLC still showed some symmetrical 2-propynyl urea. The solid was recrystallized again from ethanol/water to yield 3.5 g (46.9%) of pale yellow crystalline product, m.p. 140°-141° C.

Analysis: Calculated for $C_{14}H_{13}F_3N_2O_2$: C,56.38; H,4.39; N,9.39. Found: C,56.34; H,4.36; N,9.32.

EXAMPLE 21

N-(2-Methyl-2-propenyl)-3-[4-(trifluoromethyl)phenoxy]-1-azetidinecarboxamide

A stirred solution of 3.6 g (0.022 mole) of 1,1'-carbonyldiimidazole in 75 ml of methylene chloride under nitrogen was treated with 1.6 g (0.022 mole) of 2-methyl-2-propenylamine (added via a syringe and needle through a septum placed in one neck of the reaction flask). After stirring for 1 hr, 6.2 g (0.02 mole) of 3-[4-(trifluoromethyl)phenoxy]azetidine oxalate was added all at once followed in 30 min with 5 ml of triethylamine and stirring was continued for 3 hr. The reaction mixture was washed with water (2×25 ml), dried over magnesium sulfate and concentrated in vacuo. The oily residue solidified on standing and was recrystallized from isopropyl ether to yield 3.7 g (58.9%) of fine white crystals, m.p. 101°-102° C.

Analysis: Calculated for $C_{15}H_{17}F_3N_2O_2$: C,57.32; H,5.45; N,8.91. Found: C,57.45; H,5.51; N,9.23.

EXAMPLE 22

N-(2-Methyl-2-propenyl)-3-[3-(trifluoromethyl)phenoxy]-1-azetidinecarboxamide

A solution of 3.6 g (0.022 mole) of 1,1'-carbonyldiimidazole in 75 ml of methylene chloride was stirred under nitrogen while 1.6 g (0.022 mole) of methallylamine was added with a syringe and needle through a septum installed in one neck of the reaction flask. The reaction was slightly exothermic. The reaction mixture was stirred for 1 hr, then treated with 6.2 g (0.02 mole) of 3-[3-(trifluoromethyl)phenoxy]azetidine oxalate followed in 0.5 hr with 5 ml of triethylamine and stirring continued for 16 hr. The reaction mixture was washed with 2×30 ml of water, dried over magnesium sulfate, and concentrated on a rotary evaporator to yield 6.7 g of oily residue which solidified. The residue was recrystallized from isopropyl ether to yield 5.4 g (85.9%) of fine white crystals, m.p. 90°-91° C.

Analysis: Calculated for $C_{15}H_{17}F_3N_2O_2$: C,57.32; H,5.45; N,8.91. Found: C,57.20; H,5.50; N,8.95.

EXAMPLE 23

N-(3-Methyl-2-butenyl)-3-[4-(trifluoromethyl)phenoxy]-1-azetidinecarboxamide

A solution of 3.6 g. (0.022 mole) of 1,1'-carbonyldiimidazole in 100 ml of methylene chloride was cooled in a tap water bath and while stirring under nitrogen, 1.87 g (0.022 mole) of 3-methyl-2-butenylamine was added dropwise. After stirring for 1 hr, 6.2 g (0.02 mole) of 3-[4-(trifluoromethyl)phenoxy]azetidine oxalate was added all at once followed in 0.5 hr with 5 ml of triethylamine and stirring continued for an additional 16 hr. The reaction mixture was washed with 2×50 ml of water, dried over magnesium sulfate and concentrated on a rotary evaporator to yield a semi-solid residue. Trituration with isopropyl ether and filtration yielded 7 g of crude product which was recrystallized from ethanol-water to give 5.5 g (83.8%) of white crystals, m.p. 156.5°-158° C.

Analysis: Calculated for $C_{16}H_{19}F_3N_2O_2$: C,58.53; H,5.83; N,8.53. Found: C,58.81; H,5.89; N,8.58.

EXAMPLE 24

N-(3-Methyl-2-butenyl)-3-[3-(trifluoromethyl)phenoxy]-1-azetidinecarboxamide

A solution of 3.6 g (0.022 mole) of 1,1'-carbonyldiimidazole in 100 ml of tetrahydrofuran was cooled with a tap water bath and stirred under nitrogen while 1.6 g (0.022 mole) of 3-methyl-2-butenylamine was added with a syringe and needle. The reaction mixture was stirred for 1 hr, then treated with 6.2 g (0.02 mole) of 3-[3-(trifluoromethyl)phenoxy]azetidine oxalate followed in 0.5 hr with 5 ml of triethylamine and stirring continued for 72 hr. The reaction mixture was diluted with 500 ml of ice water and extracted with 6×50 ml of methylene chloride. The combined extracts were washed with water, dried over magnesium sulfate and concentrated to a solid residue on a rotary evaporator. Recrystallization from ethanol-water yielded 6 g of white crystals, m.p. 143°-144° C.

Analysis: Calculated for $C_{16}H_{19}F_3N_2O_2$: C,58.53; H,5.83; N,8.53. Found: C,58.46; H,5.86; N,8.69.

EXAMPLE 25

(E)-N-(2-Butenyl)-3-[4-(trifluoromethyl)phenoxy]-1-azetidinecarboxamide

A mixture of 3.6 g (0.022 mole) of 1,1'-carbonyldiimidazole and 1.6 g (0.022 mole) of trans-crotylamine was stirred for 1 hr, then treated with 6.2 g (0.02 mole) of 3-[4-(trifluoromethyl)phenoxy]azetidine oxalate and followed in 0.5 hr with 5 ml of triethylamine with stirring continued for 16 hr. The partially crystalline mixture was washed with 2×50 ml of water, dried over magnesium sulfate and concentrated on a rotary evaporator to a solid residue, 14.2 g. Recrystallization from methanol-water yielded 5.35 g (85.1%) of fine white crystals, m.p. 157°-158° C.

Analysis: Calculated for $C_{15}H_{17}F_3N_2O_2$: C,57.32; H,5.45; N,8.91. Found: C,57.47; H,5.49; N,9.00.

EXAMPLE 26

(E)-N-(2-Butenyl)-3-[3-(trifluoromethyl)phenoxy]-1-azetidinecarboxamide

A solution of 3.6 g (0.022 mole) of 1,1'-carbonyldiimidazole in 60 ml of methylene chloride was cooled in an ice bath while stirring under nitrogen while 1.6 g (0.022 mole) of trans-crotylamine was added dropwise. After warming to ambient temperature, 6.2 g (0.02 mole) of 3-[3-(trifluoromethyl)phenoxy]azetidine oxalate was added all at once followed in 0.25 hr by 5 ml of triethylamine with stirring continued for 72 hr. The reaction solution was washed with 2×50 ml of water, dried over magnesium sulfate and concentrated on a rotary evaporator to a solid residue, 7 g. Recrystallization from methanol-water gave 5.5 g of slightly yellow product. A second recrystallization with charcoal treatment from isopropyl ether yielded 3.75 g (59.7%) of fine white crystals, m.p. 127°-128° C.

Analysis: Calculated for $C_{15}H_{17}F_3N_2O_2$: C,57.32; H,5.45; N,8.91. Found: C,57.35; H,5.47; N,8.94.

EXAMPLE 27

N-Phenyl-3-[3-(trifluoromethyl)phenoxy]-1-azetidinecarboxamide

A stirred slurry of 6.2 g (0.02 mole) of 3-[3-(trifluoromethyl)phenoxy]azetidine oxalate in 60 ml of tetrahydrofuran was treated with 5 ml of triethylamine followed by 2.62 g (0.022 mole) of phenyl isocyanate and stirring continued for 16 hr. The reaction mixture was diluted with water until an oil separated which quickly solidified. The aqueous tetrahydrofuran was decanted and the solid residue recrystallized from ethanol-water to yield 5.3 g (80.1%) of white crystals, m.p. 137°-138° C.

Analysis: Calculated for $C_{17}H_{15}F_3N_2O_2$: C,60.71; H,4.50; N,8.33. Found: C,60.81; H,4.47; N,8.35.

EXAMPLE 28

N-Phenyl-3-[4-(trifluoromethyl)phenoxy]-1-azetidinecarboxamide

A stirred slurry of 6.2 g (0.02 mole) of 3-[4-(trifluoromethyl)phenoxy]azetidine oxalate and 2.62 g (0.022 mole) of phenyl isocyanate in 60 ml of tetrahydrofuran was treated with 5 ml of triethylamine and stirring continued for 16 hr. The reaction mixture was diluted with water until an oil separated. The tetrahydrofuran-water portion was decanted and the residue solidified on standing. Recrystallization from ethanol-water yielded 3.5 g (53.4%) of fine white crystals, m.p. 174.5°-176° C.

Analysis: Calculated for $C_{17}H_{15}F_3N_2O_2$: C,60.71; H,4.50; N,8.33. Found: C,60.91; H,4.53; N,8.35.

EXAMPLE 29 trans-N,2-Dimethyl-3-[3-(trifluoromethyl)phenoxy]-1-azetidinecarboxamide

A stirred solution of 6 g (0.015 mole) of crude trans-2-methyl-3-[3-(trifluoromethyl)phenoxy]azetidine in 50 ml of tetrahydrofuran was treated with 0.94 g (0.0165 mole) of methyl isocyanate added dropwise and stirred for 16 hr under a blanket of nitrogen. Dilution of the reaction mixture with water produced an oil which solidified. After decanting the aqueous tetrahydrofuran phase, the solid residue was recrystallized from ethanol-water to yield 3.95 g (91.4%) of fine white crystals, m.p. 104.5°-106° C.

Analysis: Calculated for $C_{13}H_{15}F_3N_2O_2$: C,54.17; H,5.25; N,9.72. Found: C,54.50; H,5.29; N,9.71.

EXAMPLE 30 trans-2-Methyl-3-[3-(trifluoromethyl)phenoxy]-1-azetidinecarboxamide

A mixture of 6 g (0.015 mole) of crude trans-2-methyl-3-[3-(trifluoromethyl)phenoxy]azetidine (purity 56.6% contains diphenylmethane) and 2.4 g (0.0225 mole) of nitrourea in 40 ml of acetone was treated with 4 ml of water, then heated until a clear homogenous solution was obtained. The reaction mixture was stirred overnight as it cooled to ambient temperature and diluted with water until an oil separated. The oil solidified and was recrystallized from ethanol/water, yielding 4.3 g of white plate-like crystals; m.p. 117°-118° C. The product was recrystallized from benzene, yielding 3.35 g (96.8%) of crystals, m.p. 118°-119° C.

Analysis: Calculated for $C_{12}H_{13}F_3N_2O_2$: C,52.56; H,4.78; N,10.22. Found: C,52.54; H,4.74; N,10.17.

EXAMPLE 31 trans-2-Methyl-N-(2-propenyl)-3-[3-(trifluoromethyl)phenoxy]-1-azetidinecarboxamide A solution of 6 g (0.015 mole) of crude trans-2-methyl-3-[3-(trifluoromethyl)phenoxy]azetidine (56.6%) in 50 ml of tetrahydrofuran was treated with 1.54 g (0.0165 mole) of 2-propenyl isocyanate all at once and stirred under a blanket of nitrogen for 16 hr. The reaction mixture was diluted with water until an oil separated. The oil failed to crystallize and after 7 weeks it was triturated with isopropyl ether (3×25 ml). The combined triturates gave 400 mg of white granular crystals (8.5%), m.p. 55°-57° C.

Analysis: Calculated for $C_{15}H_{17}F_3N_2O_2$: C,57.32; H,5.45; N,8.91. Found: C,57.36; H,5.50; N,8.97.

EXAMPLE 32

3-(3-Chlorophenoxy)-N-methyl-1-azetidinecarboxamide

A solution of 1-chlorocarbonyl-3-(3-chlorophenoxy)azetidine (0.01275 mole) in 20 ml of tetrahydrofuran was treated with 4 ml (0.05 mole) of 40% aqueous methylamine and stirred for 16 hr. The reaction mixture was diluted with water until an oil began to separate, then extracted with 3×50 ml of benzene. The combined extracts were dried over magnesium sulfate and concentrated to a solid which was recrystallized from benzene/ligoin to yield 1.2 g (40.0%) of fine white crystals, m.p. 140°-141° C.

Analysis: Calculated for $C_{11}H_{13}ClN_2O_2$: C,54.89; H,5.44; N,11.64. Found: C,55.05; H,5.58; N,11.52.

EXAMPLE 33

3-(3-Chlorophenoxy)-N-(2-propenyl)-1-azetidinecarboxamide

A solution of 5.4 g (0.017 mole) of 1-chlorocarbonyl-3-(3-chlorophenoxy)azetidine in 20 ml of tetrahydrofuran was treated with 2.3 g (0.04 mole) of 2-propenylamine and stirred for 2 hr. The reaction solution was concentrated in vacuo to a rose beige solid. Trituration of the solid with water gave, after filtering, 4.4 g of crude product. After drying, the solid was recrystallized with charcoal treatment from 2% acetone/isopropyl ether to yield 1.7 g (37.5%) of pale beige crystals, m.p. 87°-89° C.

Analysis: Calculated for $C_{13}H_{15}ClN_2O_2$: C,58.54; H,5.67; N,10.50. Found: C,58.48; H,5.72; N,10.49.

EXAMPLE 34

N-Methyl-3-(2-pyridinyloxy)-1-azetidinecarboxamide

A 2M benzene solution of phosgene (40 ml, 0.08 mole) was added to a suspension of 10 g of finely ground potassium carbonate in 40 ml of methylene chloride. The mixture was stirred for 15 min. at room temperature and 10 g (0.056 mole) of 1-(1-phenylethyl)-3-(2-pyridyloxy)azetidine in 50 ml of methylene chloride was added with mild cooling. The mixture was stirred at room temperature for 1 hr and concentrated on a rotary evaporator (25° C./30 mm). The residue was treated with 100 ml of tetrahydrofuran and cooled with an ice bath. To the cooled, stirred mixture was added 20 ml of 40% aqueous methylamine. The mixture was stirred for 20 min and partitioned between methylene chloride and water. The methylene chloride was dried over sodium sulfate and concentrated. The residue was crystallized from benzene-ethanol and recrystallized from ethyl acetate-isopropyl alcohol. Yield of title compound was 2.3 g (14%), m.p. 165°-168° C.

Analysis: Calculated for $C_{10}H_{13}N_3O_2$: C,57.96; H,6.32; N,20.28. Found: C,57.93; H,6.34; N,20.12.

EXAMPLE 35

N-(2-Propenyl)-3-(2-pyridinyloxy)-1-azetidinecarboxamide

To a stirred suspension of 10 g (0.072 mole) of finely ground potassium carbonate in 90 ml of methylene chloride was added 32 ml (0.062 mole) of 2M phosgene in benzene. The mixture was stirred for 15 min and 8 g (0.031 mole) of 1-(1-phenylethyl)-3-(2-pyridyloxy)azetidine in 50 ml of methylene chloride was added. The mixture was stirred at 25° C. for 2 hr and concentrated on a rotary evaporator at 25° C./30 mm, and the residue was treated with 100 ml of tetrahydrofuran. The stirred mixture was cooled with an ice bath and treated dropwise with 4 g (0.07 mole) of allyl amine. After stirring 30 min at 25° C., the material was partitioned between water and methylene chloride. The methylene chloride was dried and concentrated. The residue was chromatographed on a Waters ® PREP-500 HPLC using a silica column and eluting with 50% ethylacetate-hexane. The product was crystallized twice from isopropyl ether. Yield of title compound was 1.5 g (21%), m.p. 72°-76° C.

Analysis: Calculated for $C_{12}H_{15}N_3O_2$: C,61.79; H,6.48; N,18.01. Found: C,61.53; H,6.50; N,17.96.

EXAMPLE 36

3-(2-Pyridinyloxy)-1-azetidinecarboxamide

A 2M benzene solution of phosgene (32 ml, 0.062 mole) was added to a stirred suspension of 10 g of finely ground potassium carbonate in 80 ml of methylene chloride. The mixture was stirred for 15 min and 8 g (0.031 mole) of 1-(1-phenylethyl)-3-(2-pyridyloxy)azetidine in 50 ml of methylene chloride added. The mixture was stirred for 35 min and concentrated on a rotary evaporator (25° C./30 mm). The residue was treated with 100 ml of tetrahydrofuran, cooled with an ice bath and 20 ml of concentrated ammonium hydroxide added slowly while stirring vigorously. The mixture was stirred 1 hr at room temperature and partitioned between methylene chloride and water. The water layer was extracted 2 times with methylene chloride and the combined organic layers were concentrated. The residue was crystallized from benzene and recrystallized from isopropyl ether. Yield of title compound was 1.4 g, m.p. 133°-137° C.

Analysis: Calculated for $C_9H_{11}N_3O_2$: C,55.95; H,5.74; N,21.75. Found: C,55.73; H,5.71; N,21.10.

EXAMPLE 37

1-Propyl-4-[3-[3-(trifluoromethyl)phenoxy]-1-azetidinylcarbonyl]piperazine fumarate [1:1]

A mixture of 2.8 g (0.01 mole) of 3-[3-(trifluoromethyl)phenoxy]-1-azetidinecarbonyl chloride and 4.2 g (0.03 mole) of potassium carbonate in 25 ml of tetrahydrofuran was stirred for 10 min, then treated with 2.9 g (0.01 mole) of 1-propylpiperazine dihydrobromide in small portions. After 30 min, a few pieces of ice were added. After stirring for 17 hr, the reaction was diluted with 200 ml of water then extracted with methylene chloride (2×50 ml). The combined extracts were dried over magnesium sulfate and concentrated in vacuo, yielding 4.84 g of crude residue. The residue was converted to the fumarate salt in 2-propanoi, concentrated to a solid in vacuo and recrystallized from acetone with a trace of ethanol to yield 2.9 g (59.5%) of fine white crystals; m.p. 117°-123° C.

Analysis: Calculated for $C_{18}H_{24}F_3N_3O_2 \cdot C_4H_4O_4$: C,54.21; H,5.79; H,8.62. Found: C,54.62; H,6.08; N,8.34.

EXAMPLE 38

1-[3-[4-(Trifluoromethyl)phenoxy]-1-azetidinylcarbonyl]-1H-imidazole

A mixture of 1.7 g (0.01 mole) 1,1'-carbonyldiimidazole in 50 ml of tetrahydrofuran and 3 g (0.015 mole) of 3-[4-(trifluoromethyl)phenoxy]azetidine was stirred for 6 hr. The reaction mixture was diluted with water and extracted with 3×50 ml of methylene chloride. The extracts upon concentrating in vacuo gave an amber residue which was dissolved in 20 ml of benzene and washed with dilute hydrochloric acid, then washed with water. The benzene portion was concentrated to give a semi-solid residue which when triturated with isopropyl ether gave 1.4 g of gray material. Recrystallization from acetonitrile gave 1.3 g (41.8%) of fine gray crystals, m.p. 139°-140° C.

Analysis: Calculated for $C_{14}H_{12}F_3N_3O_2$: C,54.02; H,3.89; N,13.50. Found: C,54.33; H,3.96; N,13.89.

EXAMPLE 39

3-(3-Chlorophenoxy)-1-azetidinecarboxamide

A solution of 5.4 g (0.017 mole) of 1-chlorocarbonyl-3-(3-chlorophenoxy)azetidine in 20 ml of tetrahydrofuran was treated with 3 ml of ammonium hydroxide and stirred for 1 hr. The reaction mixture was concentrated in vacuo to a wet solid, 4 g, which was recrystallized after drying from benzene to yield 1.5 g of white crystalline powder, m.p. 163°-164.5° C. Yield calculated from the 1-(2-phenylethyl)azetidine compound was 38.9%.

Analysis: Calculated for $C_{10}H_{11}ClN_2O_2$: C,52.99; H,4.89; N,12.36. Found: C,52.99; H,4.91; N,12.32.

EXAMPLE 40

3-(3-Fluorophenoxy)-N-methyl-1-azetidinecarboxamide

A stirred mixture of 5.4 g (0.02 mole) of 3-(3-fluorophenoxy)-azetidine oxalate and 1.7 g (0.022 mole) of methyl isocyanate in 20 ml of tetrahydrofuran was treated with 5 ml of triethylamine then stirring was continued for 3 hr. The reaction was diluted with water and the fine crystalline precipitate obtained was collected by filtration and dried at 60° C. under vacuum to yield 3 g (66.9%) of product, m.p. 155°-156° C. Yield: 66.9%.

Analysis: Calculated for $C_{11}H_{13}FN_2O_2$: C,58.92; H,5.84; N,12.49. Found: C,58.93; H,5.91; N,12.26.

EXAMPLE 41

3-(3-Fluorophenoxy)-1-azetidinecarboxamide

A stirred slurry of 3 g (0.012 mole) of 3-(3-fluorophenoxy)azetidine oxalate [1:1] in 20 ml of acetone was treated with 3 ml of triethylamine and stirred for 1 hr. The resulting solution was treated with 2.5 g (0.024 mole) of nitrourea and 2 ml of water then stirred for 16 hr. The reaction mixture was diluted with water and the product crystallized. Recrystallization from methanol-water yielded 1.1 g (43.6%) of a white crystalline solid, m.p. 169°-170° C.

Analysis: Calculated for $C_{10}H_{11}FN_2O_2$: C,57.14; H,5.28; N,13.33. Found: C,57.49; H,5.31; N,13.41.

EXAMPLE 42

1-[3-[3-(Trifluoromethyl)phenoxy]-1-azetidinylcarbonyl]homopiperidine

A solution of 5.6 g (0.02 mole) of 1-chlorocarbonyl-3-[3-(trifluoromethyl)phenoxy]azetidine in 50 ml of tetrahydrofuran was treated with 3 g (0.022 mole) of potassium carbonate and while stirring, 2.3 g (0.022 mole) of hexamethyleneimine was added. This mixture was treated with 10 g of ice and stirred for 2 hr. The tetrahydrofuran was decanted and concentrated to an oil residue, 8.1 g. The residue was dissolved in benzene and washed first with diluted acid then with water, dried over magnesium sulfate and concentrated on a rotary evaporator to a pale yellow oil. The oil crystallized when cooled to −70° C. and was recrystallized from hexane to give fine white crystals, 5 g (75%); m.p. 64.5°-66° C.

Analysis: Calculated for $C_{17}H_{21}F_3N_2O_2$: C,59.64; H,6.18; N,8.18. Found: C,59.61; H,6.05; N,8.19.

EXAMPLE 43

1-[3-[3-(Trifluoromethyl)phenoxy]-1-azetidinylcarbonyl]piperidine

A solution of 5.6 g (0.02 mole) of 1-chlorocarbonyl-3-[3-(trifluoromethyl)phenoxy]azetidine in 50 ml of tetrahydrofuran was treated with 3 g (0.022 mole) of potassium carbonate and while stirring, 1.9 g (0.022 mole) of piperidine was added dropwise. The mixture was then treated with 10 g of ice and stirred for 2 hr. The tetrahydrofuran was decanted then concentrated on a rotary evaporator to yield an amber oil, 6.9 g. The oil was dissolved in benzene, washed with dilute acid then water, dried over magnesium sulfate and concentrated in vacuo. This oil crystallized when cooled to −70° C. and was recrystallized from hexane with charcoal treatment at 0° C. yielding pale tan crystals, 4.5 g (68.5%), m.p. 50°-52° C.

Analysis: Calculated for $C_{16}H_{19}F_3N_2O_2$: C,58.53; H,5.83; N,8.53. Found: C,58.44; H,5.70; N,8.51.

EXAMPLE 44

1-(1-Azetidinylcarbonyl)-3-[3-(trifluoromethyl)phenoxy]azetidine

A mixture of 5.6 g (0.02 mole) of 1-chlorocarbonyl-3-[3-(trifluoromethyl)phenoxy]azetidine and 3 g (0.027 mole) of potassium carbonate in 50 ml of tetrahydrofuran was treated with 1.26 g (0.022 mole) of azetidine added dropwise to the stirred mixture. After stirring for 15 min, the reaction was treated with 10 g of ice and stirred for an additional 72 hr. The tetrahydrofuran was decanted from the salt-paste and concentrated on a rotary evaporator to yield an oil, 6.3 g. This oil crystallized when cooled to −70° C. and was recrystallized from hexane yielding 5.1 g (85%) of fine white crystals, m.p. 65°-68° C.

Analysis: Calculated for $C_{14}H_{15}F_3N_2O_2$: C,56.00; H,5.04; N,9.33. Found: C,55.98; H,5.00; N,9.37.

EXAMPLE 45

1-[3-[3-(Trifluoromethyl)phenoxy]-1-azetidinylcarbonyl]pyrrolidine

A mixture of 5.6 g (0.02 mole) of 1-chlorocarbonyl-3-[3-(trifluoromethyl)phenoxy]azetidine and 3 g (0.02 mole) of potassium carbonate in 50 ml of tetrahydrofuran was stirred while 1.57 g (0.022 mole) of pyrrolidine was added all at once. After stirring for 15 min, 10 g of ice was added and stirring continued for an additional 72 hr. The tetrahydrofuran was decanted from the salt paste and concentrated on a rotary evaporator to yield a yellow oil, 7.2 g. The oil solidified when cooled to $-70°$ C. and was recrystallized from hexane to yield 3.95 g (64.5%) of silver-white, platelike crystals, m.p. 107°–108° C.

Analysis: Calculated for $C_{15}H_{17}F_3N_2O_2$: C,57.32; H,5.45; N,8.91. Found: C,57.65; H,5.45; N,8.99.

EXAMPLE 46

N-Methyl-N-(2-propynyl)-3-[3-(trifluoromethyl)-phenoxy]-1-azetidinecarboxamide A mixture of 5.6 g (0.02 mole) of 1-chlorocarbonyl-3-[3-(trifluoromethyl)phenoxy]azetidine and 3 g (0.022 mole) of potassium carbonate in 50 ml of tetrahydrofuran was treated while stirring with 1.52 g of N-methylpropargylamine. After stirring for 15 min, 10 g of ice was added and stirring continued for an additional 72 hr. The tetrahydrofuran was decanted from the salt paste and concentrated on a rotary evaporator to yield an amber oil, 5.9 g. This oil solidified when cooled to $-70°$ C. and was recrystallized from hexane to yield 4.6 g (74.2%) of fine white crystals, m.p. 71°–73° C.

Analysis: Calculated for $C_{15}H_{15}F_3N_2O_2$: C,57.69; H,4.84; N,8.97. Found: C,58.01; H,4.76; N,9.00.

EXAMPLE 47

1-Methyl-4-[3-[3-(trifluoromethyl)phenoxy]-1-azetidinylcarbonyl]piperazine oxalate [1:1.5]

A solution of 5.6 g (0.02 mole) of 1-chlorocarbonyl-3-[3-(trifluoromethyl)phenoxy]azetidine in 50 ml of tetrahydrofuran was cooled to 5° C. and while stirring, treated with 5 g (0.05 mole) of 1-methylpiperazine added all at once. The reaction was allowed to warm to ambient temperature while stirring approximately 18 hr. The reaction mixture was diluted 10 fold with water and extracted with 3×50 ml of methylene chloride. The extracts were combined, dried over magnesium sulfate, filtered and concentrated in vacuo to a yellow oil, 6.8 g. The oil was dissolved in acetone and treated with 2 g of oxalic acid. A clear solution was obtained when heated to boiling and upon cooling, the product precipitated. Filtration yielded a fine white crystalline product, 8.1 g (84.7%), m.p. 144°–145° C.

Analysis: Calculated for $C_{16}H_{20}F_3N_3O_2.1.5C_2H_2O_4$: C,47.70; H,4.85; N,8.78. Found: C,47.71; H,4.85; N,8.74.

EXAMPLE 48

1-Methyl-4-[3-[3-(trifluoromethyl)phenoxy]-1-azetidinylcarbonyl]piperazine fumarate [1:1]

The same procedure as used to prepare 1-methyl-4-[3-[3-(trifluoromethyl)phenoxy]-1-azetidinylcarbonyl]piperazine oxalate [1:1.5] was followed except the free base was converted to the fumarate salt (instead of the oxalate salt) by dissolving the residue obtained from work-up in 5 ml of isopropanol and treating this solution with 1.2 g of fumaric acid dissolved in 25 ml of boiling isopropanol. The cooled mixture yielded 1.3 g of white product. The filtrate was concentrated in vacuo and the resulting solid was combined with the 1.3 g of product previously obtained. Recrystallization from isopropanol/isopropyl ether gave 3.3 (91.8%) of fine white crystals, m.p. 132°–133° C.

Analysis: Calculated for $C_{16}H_{20}F_3N_3O_2.C_4H_4O_4$: C,52.29; H,5.27; N,9.15. Found: C,52.42; H,5.21; N,9.13.

EXAMPLE 49

N-(4-Methylphenyl)-3-[3-(trifluoromethyl)phenoxy]-1-azetidinecarboxamide

To a stirred mixture of 1.88 g (0.0067 mole) of 3-[3-(trifluoromethyl)phenoxy]-1-azetidinecarbonyl chloride and 1 g (0.007 mole) of potassium carbonate was added 20 ml of tetrahydrofuran and 0.75 g (0.007 mole) of 4-toluidine. After stirring for 0.5 hr, ice was added and stirring continued for 18 hr. The reaction mixture was diluted with water and then decanted from an oil residue which separated. Upon standing, this residue solidified and was recrystallized from acetone to yield 1.1 g (47%) of large, white crystals, m.p. 191°–192° C.

Analysis: Calculated for $C_{13}H_{17}F_3N_2O_2$: C,61.71; H,4.85; N,8.00. Found: C,61.64; H,4.78; N,7.99.

EXAMPLE 50

N-(4-Chlorophenyl)-3-[3-(trifluoromethyl)phenoxy]-1-azetidinecarboxamide

A mixture of 5.4 g (0.02 mole) of 3-[3-(trifluoromethyl)phenoxy]azetidine oxalate [1:1] and 3.38 g (0.022 mole) of 4-chlorophenyl isocyanate was stirred in 20 ml of tetrahydrofuran for 15 min then treated with 5 ml of triethylamine. The reaction mixture was exothermic and was stirred for 18 hr as it cooled to ambient temperature. The reaction mixture was diluted with 100 ml of water and the residue which separated solidified. Filtration yielded 8.9 g of crude wet solid. Recrystallization from methyl isobutyl ketone and 30/60 petroleum ether yielded 3.65 g (49.7%) of fine white crystals, m.p. 138°–140° C.

Analysis: Calculated for $C_{17}H_{14}ClFN_2O_2$: C,55.07; H,3.81; N,7.56. Found: C,55.16; H,3.79; N,7.70.

EXAMPLE 51

3-(4-Fluorophenoxy)-N-methyl-1-azetidinecarboxamide

A solution of 4.6 g (0.02 mole) of 3-(4-fluorophenoxy)-1-azetidinecarbonyl chloride in 15 ml of tetrahydrofuran was stirred while 6.2 g (0.08 mole) of 40% aqueous methylamine was added. The reaction mixture was exothermic and was allowed to cool to ambient temperature while stirring for 18 hr. The reaction mixture was diluted with 200 ml of ice water and the oil droplets which separated quickly crystallized. Filtration yielded 6.6 g of crude product. The solid was dissolved in 100 ml of methylene chloride, treated with 15 g of silica gel and stirred for 2 hr. The silica gel was removed by filtration and washed with 200 ml of 50/50 ethyl acetatemethylene chloride. The combined filtrates were concentrated on a rotary evaporator, yielding 5.8 g of solid residue. The solid was recrystallized by dissolving in 22 ml of acetone and adding 88 ml of isopropyl ether. The volume was reduced to 40 ml by boiling under nitrogen atmosphere and upon cooling the product crystallized. Filtration yielded 2.95 (66.7%) of white crystals, m.p. 140°–142° C.

Analysis: Calculated for $C_{11}H_{13}FN_2O_2$: C,58.92; H,5.84; N,12.49. Found: C,59.01; H,5.87; N,12.37.

EXAMPLE 52

3-(4-Fluorophenoxy)-1-azetidinecarboxamide

A solution of 5.52 g (0.022 mole) of crude 3-(4-fluorophenoxy)-1-azetidine carbonyl chloride in 20 ml of tetrahydrofuran was treated with 10 ml of concentrated ammonium hydroxide while stirring. The exothermic reaction mixture was stirred for 18 hr as it cooled to ambient temperature. The reaction mixture was diluted with 400 ml of ice water to produce a phase separation. Upon standing, the oily phase solidified and was collected by filtration yielding 12.5 g of crude wet product. Recrystallization from aqueous ethanol after charcoal treatment produced an oil which slowly crystallized. The sample was recrystallized from methylene chloride, yield 1.6 g (35%) of amorphous-like powder, m.p. 185°–188° C.

Analysis: Calculated for $C_{10}H_{11}FN_2O_2$: C,57.14; H,5.28; N,13.33. Found: C,57.33; H,5.31; N,12.93.

EXAMPLE 53

3-(4-Fluorophenoxy)-N-(2-propenyl)-1-azetidinecarboxamide

A stirred and cooled (32° C.) mixture of 5.52 g (0.022 mole) of crude 3-(4-fluorophenoxy)-1-azetidine carbonyl chloride and 3 g (0.02 mole) of potassium carbonate in 30 ml of tetrahydrofuran was treated with 1.5 g (0.02 mole) of 3-aminopropylene. The reaction mixture was still exothermic and was stirred for 5 hr as it cooled to ambient temperature. The reaction mixture was diluted with 200 ml of water to produce an oil phase separation. The oil portion was dissolved by extracting with 2×50 ml of benzene. The extracts were combined, dried over magnesium sulfate and concentrated in vacuo to yield 8.14 g of orange-red oil. The oil partially crystallized from benzene-ligroin with charcoal treatment, yielding first a reddish oil followed by a crystalline product. The total material was concentrated in vacuo to yield 7.45 g of amber-red oil. This oil solidified and was repeatedly triturated with isopropyl ether until only a red oil residue remained. The isopropyl ether portions were repeatedly cooled to the crystallization of residue, decanted from residue and heated to reduce volume until only a straw colored isopropyl ether solution remained. Upon cooling of this solution the title product crystallized and yielded 2.3 g (42.3%) of white crystalline product, m.p. 92°–94° C.

Analysis: Calculated for $C_{13}H_{15}FN_2O_2$: C,62.39; H,6.04; N,11.19. Found: C,62.35; H,6.04; N,11.20.

EXAMPLE 54

3-(4-Fluorophenoxy)-N-(2-propynyl)-1-azetidinecarboxamide

A mixture of 5.52 g (0.022 mole) of crude 3-(4-fluorophenoxy)-1-azetidine carbonyl chloride and 3 g (0.02 mole) of potassium carbonate in 30 ml of tetrahydrofuran was cooled in an ice bath and while stirring treated with 1.1 g (0.02 mole) of propargylamine added dropwise. After stirring for 5 hr, the reaction mixture was diluted with 250 ml of water and the resulting solid collected by filtration to yield 8.67 g of wet product. Recrystallization from acetone after filtration to remove some amorphous material, gave a tacky solid. A second recrystallization from benzene after treating with charcoal yielded 2.7 g (50%) of beige crystals, m.p. 106°–108° C.

Analysis: Calculated for $C_{13}H_{13}FN_2O_2$: C,62.90; H,5.28; N,11.28. Found: C,62.81; H,5.28; N,11.21.

EXAMPLE 55

3-(3,4-Dichlorophenoxy)-N-methyl-1-azetidinecarboxamide

A solution of 5.6 g (0.02 mole) of 3-(3,4-dichlorophenoxy)-1-azetidinecarbonyl chloride in 20 ml of tetrahydrofuran was stirred while 5 ml (0.06 mole) of 40% aqueous methylamine was added slowly, stirring was continued for 18 hr. The reaction mixture was diluted with 200 ml of ice water, and the solid which formed was collected by filtration, 6.9 g. The crude wet solid was recrystallized from ethanol/water to yield 3.65 g (66.3%) of greenish-gray plate-like crystals, m.p. 158°–159° C.

Analysis: Calculated for $C_{11}H_{12}Cl_2N_2O_2$: C,48.02; H,4.40; N,10.18. Found: C,48.18; H,4.39; N,10.00.

EXAMPLE 56

3-(3,4-Dichlorophenoxy)-N-(2-propenyl)-1-azetidinecarboxamide

A stirred solution of 5.6 g (0.02 mole) of 3-(3,4-dichlorophenoxy)-1-azetidinecarbonyl chloride in 20 ml of tetrahydrofuran was treated with 3.0 g (0.04 mole) of propenylamine, and stirring was continued for 18 hr. The reaction mixture was diluted with 200 ml of ice water, and the solid which formed was collected by filtration, yielding 7.1 g of crude wet product. Recrystallization from benzene/ligroin yielded 3.95 g (65.6%) of white crystals, m.p. 98°–99° C.

Analysis: Calculated for $C_{13}H_{14}Cl_2N_2O_2$: C,51.85; H,4.69; N,9.30. Found: C,51.94; H,4.67; N,9.27.

EXAMPLE 57

3-(3,4-Dichlorophenoxy)-N-(2-propynyl)-1-azetidinecarboxamide

A stirred mixture of 5.6 g (0.02 mole) of 3-(3,4-dichlorophenoxy)-1-azetidinecarbonyl chloride and 3 g (0.02 mole) of potassium carbonate in 20 ml of tetrahydrofuran was treated with 1.1 g (0.02 mole) of 2-propynylamine added dropwise from a needle syringe then stirred for an additional 18 hr. The reaction mixture was diluted with 200 ml of water and the resulting solid collected by filtration to yield 7.1 g of crude product. Recrystallization from isopropyl ether yielded 4.98 g (83.2%) of pale beige crystals, m.p. 119°–121° C.

Analysis: Calculated for $C_{13}H_{12}Cl_2N_2O_2$: C,52.20; H,4.04; N,9.36. Found: C,52.20; H,3.96; N,9.19.

EXAMPLE 58

3-(4-Chlorophenoxy)-N-(2-propynyl)-1-azetidinecarboxamide

A stirred mixture of 7.4 g (0.03 mole) of 3-(4-chlorophenoxy)-1-azetidinecarbonyl chloride and 4.5 g (0.03 mole) of potassium carbonate in 20 ml of tetrahydrofuran was treated with 1.7 g (0.03 mole) of 2-propynylamine added dropwise from a needle and syringe. After stirring for 16 hr, the reaction mixture was diluted with 400 ml of water and the resulting tan solid was collected by filtration, yielding 7.7 g of crude product. Repeated triturations of the crude product with hot benzene gave upon combining and cooling 1.2 g (15.2%) of tan powder, m.p. 120°–122° C.

Analysis: Calculated for $C_{13}H_{13}ClN_2O_2$: C,58.99; H,4.95; N,10.58. C,59.12; H,4.83; N,10.52.

EXAMPLE 59

3-(3-Bromophenoxy)-1-azetidinecarboxamide

A solution of 5.8 g (0.02 mole) of 3-(3-bromophenoxy)-1-azetidinecarbonyl chloride in 20 ml of tetrahydrofuran was stirred at ambient temperature while 4 ml (0.06 mole) of 57% ammonium hydroxide was slowly added. After stirring for 48 hr, the reaction mixture was diluted with 100 ml of water and the resulting solid collected by filtration (5 g). Recrystallization from isopropanol yielded 3.7 g (59%) of fine beige crystals, m.p. 188°–189° C.

Analysis: Calculated for $C_{10}H_{11}BrN_2O_2$: C,44.30; H,4.09; N,10.33. Found: C,44.06; H,4.00; N,10.25.

EXAMPLE 60

3-(3-Bromophenoxy)-N-methyl-1-azetidinecarboxamide

A stirred solution of 5.8 g (0.02 mole) of 3-(3-bromophenoxy)-1-azetidinecarbonyl chloride in 20 ml of tetrahydrofuran was treated with 4.7 g (0.06 mole) of 40% aqueous monomethylamine. After stirring for 48 hr, the reaction mixture was diluted with 100 ml of water and the solid which formed was collected by filtration (6.0 g). Recrystallization from benzene yielded 2.0 g (35.1%) of tan crystals, m.p. 134°–135° C.

Analysis: Calculated for $C_{11}H_{13}BrN_2O_2$: C,46.34; H,4.60; N,9.82. Found: C,46.09; H,4.51; N,9.86.

EXAMPLE 61

3-(3-Bromophenoxy)-N-(2-propenyl)-1-azetidinecarboxamide

A stirred solution of 5.8 g (0.02 mole) of 3-(3-bromophenoxy)-1-azetidinecarbonyl chloride in 20 ml of tetrahydrofuran was treated with 2.85 g (0.05 mole) of 2-propenylamine. After stirring for 48 hr, the reaction mixture was diluted with 100 ml of water and the reddish oil which separated solidified upon standing. The solids were collected by filtration, 5.9 g. Upon repeated trituration with boiling isopropyl ether, the combined triturates upon cooling yielded 4 g (64.4%) of fine white crystals, m.p. 90°–92° C.

Analysis: Calculated for $C_{13}H_{15}BrN_2O_2$: C,50.18; H,4.86; N,9.00. Found: C,50.19; H,4.90; N,9.09.

EXAMPLE 62

3-(3,4-Dichlorophenoxy)-1-azetidinecarboxamide

A solution of 5.6 g (0.02 mole) of 3-(3,4-dichlorophenoxy)-1-azetidinecarbonyl chloride in 20 ml of tetrahydrofuran was treated while stirring with 3 ml (0.04 mole) of 57% ammonium hydroxide. After stirring for 18 hr, the reaction mixture was diluted with 200 ml of water and the solid which separated was collected by filtration, 6.6 g. Recrystallization from ethanol-water yielded 3.0 g of white granular crystals, m.p. 179°–184° C. A second recrystallization from isopropanol yielded 2.7 g (51.7%) of fine white crystals, m.p. 185°–187° C.

Analysis: Calculated for $C_{10}H_{10}Cl_2N_2O$: C,46.00; H,3.86; N,10.73. Found: C,46.31; H,3.89; N,10.67.

EXAMPLE 63

3-(4-Chlorophenoxy)-1-azetidinecarboxamide

A solution of 5 g (0.02 mole) of 3-(4-chlorophenoxy)-1-azetidinecarbonyl chloride in 20 ml of tetrahydrofuran was stirred while 4 ml (0.06 mole) of 57% ammonium hydroxide was added all at once. After stirring for 18 hr, the reaction mixture was diluted with 200 ml of water and the solid which separated was collected by filtration, 10.5 g. Recrystallization from isopropanol yielded 2.4 g (52.9%) of gray crystalline powder, m.p. 187°–188° C.

Analysis: Calculated for $C_{10}H_{11}ClN_2O_2$: C,52.99; H,4.89; N,12.36. Found: C,52.90; H,4.85; N,12.30.

EXAMPLE 64

3-(4-Chlorophenoxy)-N-methyl-1-azetidinecarboxamide

A stirred solution of 5 g (0.02 mole) of 3-(4-chlorophenoxy)-1-azetidinecarbonyl chloride in 20 ml of tetrahydrofuran was treated with 4.7 g (0.06 mole) of 40% aqueous monomethylamine. After stirring for 18 hr, the reaction mixture was diluted with 200 ml of water and the solid which separated was collected by filtration, 5.7 g. Recrystallization from benzene-ligroin was accomplished by adding magnesium sulfate to absorb the water which separated from the wet product. After filtering and cooling the hot filtrate, the precipitated solid was collected by filtration to yield 4.1 g (85.2%) of white crystals, m.p. 144°–145° C.

Analysis: Calculated for $C_{11}H_{13}ClN_2O_2$: C,54.89; H,5.44; N,11.64. Found: C,54.89; H,5.43; N,11.65.

EXAMPLE 65

3-(4-Chlorophenoxy)-N-(2-propenyl)-1-azetidinecarboxamide

A stirred solution of 5 g (0.02 mole) of 3-(4-chlorophenoxy)-1-azetidinecarbonyl chloride in 20 ml of tetrahydrofuran with 4.5 g (0.06 mole) of 2-propenylamine. After stirring for 18 hr, the reaction mixture was diluted with 200 ml of water and the solid precipitate which formed after stirring for 5 hr was collected by filtration, 7.7 g. This product was dissolved by successive trituration with boiling isopropyl ether. The combined triturates were decanted from a thin film of oil which formed as it cooled. The cooled isopropyl ether triturates yielded 2.9 g (54.4%) of white crystalline product, m.p. 98°–99° C.

Analysis: Calculated for $C_{13}H_{15}ClN_2O_2$: C,58.54; H,5.67; N,10.50. Found: C,58.57; H,5.66; N,10.49.

EXAMPLE 66

3-(3-Bromophenoxy)-N-(2-propynyl)-1-azetidinecarboxamide

A stirred mixture of 5.8 g (0.02 mole) of 3-(3-bromophenoxy)-1-azetidinecarbonyl chloride and 2.8 g (0.02 mole) of potassium carbonate in 20 ml of tetrahydrofuran was treated with 1.1 g (0.02 mole) of 2-propynylamine added dropwise from a needle and syringe. A piece of ice was added and stirring was continued for 42 hr. The solid residue which remained was stirred with 100 ml of water then filtered, yielding 5.3 g of crude product. Recrystallization from ethanol yielded 4.0 g of fine beige crystals, m.p. 145°–147° C. After drying at 100° C. in vacuo, m.p. was 146°–147° C. (64.7%).

Analysis: Calculated for $C_{13}H_{13}BrN_2O_2$: C,50.51; H,4.24; N,9.06. Found: C,50.31; H,4.27; N,9.00.

EXAMPLE 67

3-(4-Bromophenoxy)-N-(2-propenyl)-1-azetidinecarboxamide

A stirred solution of 5.8 g (0.02 mole) of 3-(4-bromophenoxy)-1-azetidinecarbonyl chloride in 20 ml of tetrahydrofuran was treated with 4.5 g (0.06 mole) of 2-propenylamine and stirring continued for 18 hr. The reaction mixture was diluted with 200 ml of water and the oil which separated slowly solidified. After collecting the solid by filtration, it was triturated 4 times with boiling isopropyl ether. The combined triturates upon cooling yielded 3.7 g (59.5%) of white crystals, m.p. 100°–101° C.

Analysis: Calculated for $C_{13}H_{15}BrN_2O_2$: C,50.18; H,4.86; N,9.00. Found: C,50.20; H,4.90; N,9.02.

EXAMPLE 68

3-(4-Bromophenoxy)-1-azetidinecarboxamide

A stirred solution of 5.8 g (0.02 mole) of 3-(4-bromophenoxy)-1-azetidinecarbonyl chloride in 20 ml of tetrahydrofuran was treated with 3.8 g (4 ml) (0.06 mole) of 57% ammonium hydroxide. After stirring for 18 hr, the reaction mixture was diluted with 200 ml of water and the solid which separated was collected by filtration, 5.3 g. Recrystallization from ethanol-water yielded 4.75 g (87.6%) of fine white crystals, m.p. 193°–194° C.

Analysis: Calculated for $C_{10}H_{11}BrN_2O_2$: C,44.30; H,4.09; N,10.33. Found: C,44.46; H,4.10; N,10.39.

EXAMPLE 69

3-(4-Bromophenoxy)-N-methyl-1-azetidinecarboxamide

A stirred solution of 5.8 g (0.02 mole) of 3-(4-bromophenoxy)-1-azetidinecarbonyl chloride in 20 ml of tetrahydrofuran was treated with 4.7 g (0.06 mole) of 40% aqueous monomethylamine and stirring continued for 18 hr. The reaction mixture was diluted with 200 ml of water and the solid which separated was collected by filtration, 5.7 g. Recrystallization from ethanol-water yielded 4.9 g (85.9%) of fine white crystals, m.p. 135°–137° C.

Analysis: Calculated for $C_{11}H_{13}BrN_2O_2$: C,46.34; H,4.60; N,9.82. Found: C,46.49; H,4.62; N,9.92.

EXAMPLE 70

3-(4-Bromophenoxy)-N-(2-propynyl)-1-azetidinecarboxamide

A stirred mixture of 5.8 g (0.02 mole) of 3-(4-bromophenoxy)-1-azetidinecarbonyl chloride and 2.8 g (0.02 mole) of potassium carbonate in 20 ml of tetrahydrofuran was treated with 1.1 g (0.02 mole) of 2-propynylamine added dropwise from a needle and syringe. After stirring for 30 min, approximately 1 g of ice was added and stirring continued for 18 hr. The reaction mixture was diluted with 200 ml of water and the solid which separated was collected by filtration, 6.1 g. After drying, recrystallization from benzene-ligroin yielded 4.2 g (67.9%) of fine white crystals, m.p. 120°–122° C.

Analysis: Calculated for $C_{13}H_{13}BrN_2O_2$: C,50.51; H,4.24; N,9.06. Found: C,50.67; H,4.26; N,9.10.

EXAMPLE 71

3-(3-Methylphenoxy)-1-azetidinecarboxamide

A stirred solution of 3.92 g (0.01 mole) of crude (57.59%) 3-(3-methylphenoxy)-1-azetidinecarbonyl chloride in 15 ml of tetrahydrofuran was treated with 1.9 g (2 ml) (0.03 mole) of 57% ammonium hydroxide. After stirring for 18 hr, the reaction mixture was diluted with 200 ml of water. The oil which separated solidified on standing, (3.2 g), and was recrystallized from isopropanol, yielding 1 g (50%) of fine white crystals, m.p. 167°–168° C.

Analysis: Calculated for $C_{11}H_{14}N_2O_2$: C,64.06; H,6.84; N,13.58. Found: C,64.15; H,6.88; N,13.24.

EXAMPLE 72

3-(3-Methylphenoxy)-N-(2-propenyl)-1-azetidinecarboxamide

A stirred solution of 3.92 g (0.01 mole) of crude (57.59%) 3-(3-methylphenoxy)-1-azetidinecarbonyl chloride in 15 ml of tetrahydrofuran was treated with 2.25 g (0.03 mole) of 2-propenylamine. After stirring for 18 hr, the reaction mixture was diluted with 200 ml of water and a reddish oil separated. A sample of this oil crystallized at −70° C. and was used to seed the oil residue. The resulting solid was collected by filtration to yield 3.6 g which was recrystallized from benzene-ligroin yielding, after charcoal treatment, 1.53 g (62.2%) of pale beige crystals, m.p. 95°–96° C.

Analysis: Calculated for $C_{14}H_{18}N_2O_2$: C,68.27; H,7.37; N,11.37. Found: C,68.10; H,7.34; N,10.93.

EXAMPLE 73

3-(3-Methylphenoxy)-N-(2-propynyl)-1-azetidinecarboxamide

A stirred mixture of 3.92 g (0.01 mole) of crude (57.59%) 3-(3-methylphenoxy)-1-azetidinecarbonyl chloride and 1.4 g (0.01 mole) of potassium carbonate in 15 ml of tetrahydrofuran was treated with 0.55 g (0.01 mole) of 2-propynylamine added dropwise from a needle and syringe. After 10 min, approximately 1 g of ice was added and stirring continued for 18 hr. The reaction mixture was diluted with 200 ml of water and the oil which separated slowly solidified. The precipitated solid was collected by filtration to yield 4.7 g of crude wet product. After air drying, the solid was recrystallized from benzene-ligroin to yield 1.78 g (72.9%) of fine white crystals, m.p. 140°–142° C.

Analysis: Calculated for $C_{14}H_{16}N_2O_2$: C,68.83; H,6.60; N,11.47. Found: C,68.58; H,6.60; N,11.22.

EXAMPLE 74

3-(3-Methoxyphenoxy)-N-(2-propenyl)-1-azetidinecarboxamide

A solution of 4.85 g (0.02 mole) of 3-(3-methoxyphenoxy)-1-azetidinecarbonyl chloride in 20 ml of tetrahydrofuran was treated with 4.5 g (0.06 mole) of 2-propenylamine and stirred for 17 hr, diluted with 200 ml of water and extracted with 3×50 ml of methylene chloride. The combined extracts were dried then concentrated in vacuo to yield 4.03 g of oil residue. The residue was chromatographed on a spinning TLC plate (chromatotron) in 3 portions (3 runs) using a ethyl acetate/methylene chloride gradient. The 4th fraction of each run was combined and concentrated in vacuo to yield a white solid (1.2 g), which was recrystallized from benzene-ligroin yielding 0.94 g (18%) of fine white crystals, m.p. 121°–123° C.

Analysis: Calculated for $C_{14}H_{18}N_2O_3$: C,64.11; H,6.92; N,10.68. Found: C,64.39; H,6.78; N,10.45.

EXAMPLE 75

3-(3-Methoxyphenoxy)-N-(2-propynyl)-1-azetidinecarboxamide

A mixture of 4.85 g (0.02 mole) of 3-(3-methoxyphenoxy)-1-azetidinecarbonyl chloride and 2.8 g (0.02 mole) of anhydrous potassium carbonate in 20 ml of tetrahydrofuran was stirred while 1.1 g (0.02 mole) of 2-propynylamine was added dropwise from a needle and syringe. After stirring for 30 min, a small piece of ice was added and stirring continued for 17 hr. The reaction mixture was diluted with 200 ml of water then extracted with 3×50 ml of methylene chloride. The combined extracts were dried by passing through Whatman phase separating paper then concentrated in vacuo to an oily residue (3.73 g). This residue was dissolved in 30 ml of methylene chloride and chromatographed in three portions (3 runs) on a spinning TLC plate (chromatotron) with an ethyl acetate-methylene chloride gradient from 10%-100% ethyl acetate. A white solid (1.8 g) was obtained on concentration of the product fractions. Recrystallization from isopropyl ether yielded 0.93 g (17.9%) of white crystalline product, m.p. 121°-123° C.

Analysis: Calculated for $C_{14}H_{16}N_2O_3$: C,64.60; H,6.20; N,10.76. Found: C,64.51; H,6.30; N,10.48.

EXAMPLE 76

N-Methyl-3-(3-methylphenoxy)-1-azetidinecarboxamide

A stirred solution of 3.92 g (0.01 mole) of 3-(3-methylphenoxy)-1-azetidinecarbonyl chloride in 15 ml of tetrahydrofuran was treated with 2.4 g (0.03 mole) of 40% aqueous monomethylamine and stirring continued for 17 hr. The reaction mixture was diluted with 200 ml of water. The reddish oil residue was cooled to −78° C. whereupon it crystallized (4.28 g). Recrystallization from benzene-ligroin gave 400 mg of fine white crystals, m.p. 143°-144° C. Addition of more ligroin yielded an additional 800 mg of "cream" colored crystalline product, m.p. 138°-142° C. The two fractions were combined and recrystallized from ethanol-isopropyl ether, yielding 600 mg (27.3%) of fine white crystals, m.p. 143°-144° C.

Analysis: Calculated for $C_{12}H_{16}N_2O_2$: C,65.43; H,7.32; N,12.72. Found: C,65.40; H,7.37; N,12.72.

EXAMPLE 77

3-Phenoxy-1-azetidinecarboxamide

A stirred slurry of 7 g (0.03 mole) of 3-phenoxyazetidine oxalate [1:1] in 100 ml of acetone was treated with 5.3 g (0.05 mole) of nitrourea then after 30 min, treated with 5 ml of water and 5 ml of triethylamine. After stirring for 8 hr, the reaction mixture was diluted with 125 ml of water and stirred until a fine white crystalline solid precipitated. Filtration yielded 3.85 g, m.p. 179°-186° C. The solid was recrystallized from tetrahydrofuran to yield 1.3 g (22.5%) of fine white crystals, m.p. 195°-196° C.

Analysis: Calculated for $C_{10}H_{12}N_2O_2$: C,62.49; H,6.29; N,14.57. Found: C,62.50; H,6.29; N,14.59.

EXAMPLE 78

1-[3-(4-Bromophenoxy)-1-azetidinylcarbonyl]-4-phenylpiperazine

A solution of 2.9 g (0.01 mole) of 3-(4-bromophenoxy)-1-azetidinecarbonyl chloride in 15 ml of tetrahydrofuran was treated while stirring with 1.6 g (0.01 mole) of 1-phenylpiperazine added all at once, a solid formed instantaneously and after stirring for 2 hr, the reaction mixture was diluted with 200 ml of water, the solid did not dissolve. The solid was removed by filtration and when triturated with chloroform, all but about 1 g of solid dissolved. The chloroform solution was dried over magnesium sulfate then concentrated in vacuo. The oily residue crystallized when triturated with ligroin. Recrystallization from benzene/ligroin yielded 2.0 g (48.1%) of fine white crystals, m.p. 160°-161° C.

Analysis: Calculated for $C_{20}H_{22}BrN_3O_2$: C,57.70; H,5.33; N,10.09. Found: C,57.72; H,5.31; N,10.01.

EXAMPLE 79

1-[3-(4-Bromophenoxy)-1-azetidinylcarbonyl]-4-(phenylmethyl)piperazine

A solution of 2.9 g (0.01 mole) of 3-(4-bromophenoxy)-1-azetidinecarbonyl chloride in 15 ml of tetrahydrofuran was treated while stirring with the dropwise addition of 1.8 g (0.01 mole) of 1-benzylpiperazine. After stirring for 2 hr, the reaction mixture was diluted with water (200 ml) and 1.4 g of potassium carbonate was added. The solid precipitate was collected by filtration (5.2 g). Recrystallization from benzene/ligroin yielded 3.4 g (79.1%) of white crystals, m.p. 133°-135° C.

Analysis: Calculated for $C_{21}H_{24}BrN_3O_2$: C,58.61; H,5.62; N,9.76. Found: C,58.77; H,5.62; N,9.65.

EXAMPLE 80

1-[3-(4-Bromophenoxy)-1-azetidinylcarbonyl]-4-methylpiperazine fumarate [1:1]

A solution of 2.9 g (0.01 mole) of 3-(4-bromophenoxy)-1-azetidinecarbonyl chloride in 15 ml of tetrahydrofuran was treated while stirring with 1 g (0.01 mole) of 1-methylpiperazine and stirred for 2 hr. The paste-like slurry was diluted with water and the solid was collected by filtration (4 g, wet). Recrystallization from benzene/ligroin yielded 3.0 g of white crystalline product, m.p. 91°-95° C. The solid and 1.16 g of fumaric were dissolved in isopropanol by boiling until a clear solution was obtained. Upon cooling, the precipitated salt was collected by filtration to yield 3 g (63.8%) of fine white crystals, m.p. 197°-198° C.

Analysis: Calculated for $C_{15}H_{20}BrN_3O_2 \cdot C_4H_4O_4$: C,48.52; H,5.14; N,8.93. Found: C,48.49; H,5.14; N,8.93.

EXAMPLE 81

1-[3-(3-Bromophenoxy)-1-azetidinylcarbonyl]-4-methylpiperazine fumarate [1:1]

A stirred solution of 2.9 g (0.01 mole) of 3-(3-bromophenoxy)-1-azetidinecarbonyl chloride in 20 ml of methylene chloride was treated with 2 g (0.02 mole) of 1-methylpiperazine. After stirring for 18 hr, the reaction mixture was diluted with 200 ml of water and stirred an additional 1 hr. The methylene chloride portion was separated, dried, and concentrated in vacuo to yield 4.84 g of amber oil. A solution of the residue in 50 ml of ethyl ether was added to a hot solution of 1.16 g of fumaric acid in 25 ml of isopropanol. Upon cooling, the precipitated solid was collected by filtration to yield 2.4 g (51%) of granular crystals, m.p. 159°-161° C.

Analysis: Calculated for $C_{15}H_{20}BrN_3O_2 \cdot C_4H_4O_4$: C,48.52; H,5.14; N,8.93. Found: C,48.42; H,5.17; N,8.81.

EXAMPLE 82

1-[3-(4-Fluorophenoxy)-1-azetidinylcarbonyl]-4-methylpiperazine fumarate [1:1]

A stirred solution of 2.3 g (0.01 mole) of 3-(4-fluorophenoxy)-1-azetidinecarbonyl chloride in 20 ml of methylene chloride was treated with 2 g (0.02 mole) of 1-methylpiperazine. After stirring for 18 hr, the reaction mixture was diluted with 200 ml of water and stirred an additional 1 hr. The methylene chloride portion was separated and the aqueous portion extracted with 50 ml of methylene chloride. The methylene chloride portions were combined, dried and concentrated in vacuo to yield 2.53 g of oil residue. The oil residue in 10 ml of acetone was added to 1.16 g of fumaric acid dissolved in 50 ml of boiling isopropanol. Upon cooling, the precipitated solid was collected by filtration to yield 2.8 g (68.4%) of white granular crystals, m.p. 173°–174° C.

Analysis: Calculated for $C_{15}H_{20}FN_3O_2 \cdot C_4H_4O_4$: C,55.74; H,5.91; N,10.26. Found: C,55.67; H,5.91; N,10.09.

EXAMPLE 83

1-[3-(4-Fluorophenoxy)-1-azetidinylcarbonyl]-4-phenylpiperazine

A stirred solution of 2.3 g (0.01 mole) of 3-(4-fluorophenoxy)-1-azetidinecarbonyl chloride in 20 ml of methylene chloride was treated with 2.6 g (0.02 mole) of 1-phenylpiperazine. After stirring for 18 hr, the reaction mixture was diluted with 200 ml of water and stirred an additional 1 hr. The methylene chloride portion was separated and the aqueous portion extracted with 25 ml of methylene chloride. The combined methylene chloride portions were dried, and concentrated in vacuo to yield an oil residue (3.9 g). The oil residue solidified from isopropanol and was recrystallized by adding methanol to redissolve then ethyl ether to effect crystallization. Upon cooling, the large precipitated crystals were collected by filtration to yield 2 g (63.3%), m.p. 124°–125° C. An additional 2.5 g of crude tan product was obtained by concentrating the filtrate.

Analysis: Calculated for $C_{20}H_{22}FN_3O_2$: C,67.59; H,6.24; N,11.82. Found: C,67.62; H,6.28; N,11.75.

EXAMPLE 84

1-[3-(4-Fluorophenoxy)-1-azetidinylcarbonyl]-4-(phenylmethyl)piperazine

A stirred solution of 6.9 g (0.03 mole) of 3-(4-fluorophenoxy)-1-azetidinecarbonyl chloride in 60 ml of methylene chloride was treated with 10.8 g (0.06 mole) of 1-benzylpiperazine, added dropwise. After stirring for 18 hr, the reaction mixture was diluted with 200 ml of water and stirred for an additional 1 hr. The methylene chloride portion was separated and the aqueous portion was extracted with 2×25 ml of methylene chloride. The methylene chloride portions were combined, dried and concentrated in vacuo, yielding 12 g of oil residue. This oil solidified when triturated with ligroin and was recrystallized from benzene/ligroin to yield 10.1 g (91%) of tan crystals. A 500 mg portion was recrystallized from benzene/ligroin to yield 250 mg of fine white crystals, m.p. 109°–111° C.

Analysis: Calculated for $C_{21}H_{24}FN_3O_2$: C,68.27; H,6.55; N,11.37. Found: C,68.29; H,6.68; N,11.27.

EXAMPLE 85

1-[3-(4-Fluorophenoxy)-1-azetidinylcarbonyl]-4-(phenylmethyl)piperazine fumarate [1:1]

A 2.5 g portion of 1-[3-(4-fluorophenoxy)-1-azetidinylcarbonyl]-4-(phenylmethyl)piperazine was dissolved in isopropanol and treated with 0.8 g of fumaric acid dissolved in 2.5 ml of hot isopropanol. Upon cooling, the precipitate was collected by filtration, yielding 3 g (91.3%) of fine white crystals, m.p. 183°–184° C.

Analysis: Calculated for $C_{21}H_{24}FN_3O_2 \cdot C_4H_4O_4$: C,61.85; H,5.81; N,8.66. Found: D,61.66; H,5.93; N,8.59.

EXAMPLE 86

1-[3-(3,4-Dichlorophenoxy)-1-azetidinylcarbonyl]-4-methylpiperazine fumarate [1:1]

A stirred solution of 2.8 g (0.01 mole) of crude 3-(3,4-dichlorophenoxy)-1-azetidinecarbonyl chloride in 25 ml of tetrahydrofuran was treated with 1 g (0.01 mole) of 1-methylpiperazine then with 1.42 g (0.01 mole) of potassium carbonate. After stirring for 30 min, approximately 2 g of ice was added and stirring continued for 18 hr. The reaction mixture was diluted with 200 ml of water and an oil separated. Upon standing, this oil solidified and was collected by filtration, yielding 3.3 g of crude product. The solid was dissolved in 20 ml of isopropanol and treated with 1.16 g of fumaric acid dissolved in 25 ml of boiling isopropanol. The volume was reduced to 30 ml by heating under a stream of nitrogen and upon cooling, the precipitated salt was collected by filtration, yielding 1.35 g (95.9%) of white crystals, m.p. 187°–188° C.

Analysis: Calculated for $C_{15}H_{19}Cl_2N_3O_2 \cdot C_4H_4O_4$: C,49.58; H,5.06; N,9.13. Found: C,49.57; H,5.21; N,8.96.

EXAMPLE 87

1-[3-(3,4-Dichlorophenoxy)-1-azetidinylcarbonyl]-4-(phenylmethyl)piperazine fumarate [1:1]

A stirred solution of 2.8 g (0.01 mole) of crude 3-(3,4-dichlorophenoxy)-1-azetidinecarbonyl chloride in 25 ml of tetrahydrofuran was treated with 1.8 g (0.01 mole) of 1-benzylpiperazine then with 1.4 g (0.01 mole) of potassium carbonate. After stirring for 30 min, approximately 2 g of ice was added and stirring continued for 18 hr. The reaction mixture was diluted with 200 ml of water. After stirring for 24 hr, the oil which separated had solidified and was collected by filtration (4.8 g). The solid, dissolved in 20 ml of isopropanol, was treated with 1.16 g of fumaric acid dissolved in 25 ml of boiling isopropanol. Upon cooling, the precipitate was collected to yield 2.4 g (55%) of fine white crystalline product, m.p. 193°–195° C.

Analysis: Calculated for $C_{21}H_{23}Cl_2N_3O_2 \cdot C_4H_4O_4$: C,55.98; H,5.07; N,7.83. Found: C,55.96; H,5.10; N,7.79.

EXAMPLE 88

1-Phenyl-4-[3-[3-(trifluoromethyl)phenoxy]-1-azetidinylcarbonyl]piperazine

A mixture of 2.8 g (0.01 mole) of 3-[3-(trifluoromethyl)phenoxy]-1-azetidinecarbonyl chloride and 1.4 g (0.01 mole) of potassium carbonate in 25 ml of tetrahydrofuran was stirred for 10 min then 1.6 g (0.01 mole) of 1-phenylpiperazine was added. After stirring for 30 min, approximately 2 g of ice was added and stirring continued for 18 hr. The reaction mixture was diluted with 200 ml of water and the oil which separated was extracted into methylene chloride (2×50 ml), dried and concentrated in vacuo to yield 5.1 g of crude dark yellow oil, which solidified when cooled to −78° C. Recrystallization from isopropyl ether yielded 2.2 g (54.3%) of pale yellow crystals, m.p. 93°–94° C.

Analysis: Calculated for $C_{21}H_{22}F_3N_3O_2$: C,62.22; H,5.47; N,10.37. Found: C,62.30; H,5.54; N,10.37.

EXAMPLE 89

1-(2-Pyridinyl)-4-[3-[3-(trifluoromethyl)phenoxy]-1-azetidinylcarbonyl]piperazine A mixture of 2.8 g (0.01 mole) of 3-[3-(trifluoromethyl)phenoxy]-1-azetidinecarbonyl chloride and 1.43 g (0.01 mole) of potassium carbonate in 25 ml of tetrahydrofuran was treated, while stirring, with 1.6 g (0.01 mole) of 1-(2-pyridyl)piperazine. After 30 min, approximately 2 g of ice was added and stirring continued for 18 hr. The reaction mixture was diluted with 200 ml of water and upon stirring, transparent crystals formed. After 24 hr the precipitate was collected by filtration (4 g) and recrystallized from isopropyl ether with a trace of acetone to yield 2.6 g (64%) of silver plate-like crystals, m.p. 111°–112° C.

Analysis: Calculated for $C_{20}H_{21}F_3N_4O_2$: C,59.11; H,5.21; N,13.79. Found: C,59.20; H,5.29; N,13.76.

EXAMPLE 90

4-Phenyl-1-[3-[3-(trifluoromethyl)phenoxy]-1-azetidinylcarbonyl]piperidine

A mixture of 2.8 g (0.01 mole) of 3-[3-(trifluoromethyl)phenoxy]-1-azetidinecarbonyl chloride and 1.4 g (0.01 mole) of potassium carbonate in 25 ml of tetrahydrofuran was stirred for 10 min then treated with 1.6 g (0.01 mole) of 4-phenylpiperidine. After stirring for 30 min, approximately 2 g of ice was added and stirring continued for 18 hr. The reaction mixture was diluted with 200 ml of water and the oil which separated was extracted into methylene chloride (2×50 ml). The extracts were combined, dried and concentrated in vacuo to yield 4.95 g of crude oil which solidified when cooled to −78° C. Recrystallization from isopropyl ether yielded 1.5 g (37%) of coarse white crystals, m.p. 72°–74° C.

Analysis: Calculated for $C_{22}H_{23}F_3N_2O_2$: C,65.34; H,5.73; N,6.93. Found: C,65.41; H,5.80; N,6.94.

EXAMPLE 91

1,2,3,6-Tetrahydro-4-phenyl-1-[3-[3-(trifluoromethyl)phenoxy]-1-azetidinylcarbonyl]pyridine A mixture of 2.8 g (0.01 mole) of 3-[3-(trifluoromethyl)phenoxy]-1-azetidinecarbonyl chloride and 2.8 g (0.02 mole) of potassium carbonate in 25 ml of tetrahydrofuran was stirred for 10 min and treated with 2 g (0.01 mole) 4-phenyl-1,2,3,6-tetrahydropyridine hydrochloride. After stirring for 30 min, approximately 2 g of ice was added and stirring continued for 18 hr. The reaction mixture was diluted with 200 ml of water and the oil which separated was extracted into methylene chloride (2×50 ml). The extracts were combined, dried and concentrated in vacuo to yield 4.5 g of orange-yellow oil which solidified when cooled to −78° C. Recrystallization from isopropyl ether after charcoaling yielded 2.6 g (65%) of fine white crystals, m.p. 100°–102° C.

Analysis: Calculated for $C_{22}H_{21}F_3N_2O_2$: C,65.66; H,5.26; N,6.96. Found: C,65.71; H,5.30; N,6.96.

EXAMPLE 92

1-[3-(3,4-Dichlorophenoxy)-1-azetidinylcarbonyl]-4-(2-pyridinyl)piperazine

A stirred solution of 2.8 g (0.01 mole) of 3-(3,4-dichlorophenoxy)-1-azetidinecarbonyl chloride in 25 ml of tetrahydrofuran was treated in turn with 1.6 g (0.01 mole) of 1-(2-pyridyl)piperazine and 1.4 g (0.01 mole) of potassium carbonate. After 30 min, a solid had precipitated which dissolved when approximately 2 g of ice was added. After stirring for 18 hr, the reaction mixture was diluted with 200 ml of water and a paste-like solid separated which was filtered to yield 3.3 g of crude product. After several attempts to recrystallization from methyl isobutyl ketone, it was recrystallized from acetonitrile to yield 1.25 g (30.7%) of fine white crystals, m.p. 153.5°–154.5° C.

Analysis: Calculated for $C_{13}H_{20}Cl_2N_4O_2$: C,56.03; H,4.95; N,13.76. Found: C,55.96; H,4.96; N,13.77.

EXAMPLE 93

1-[3-(3-Bromophenoxy)-1-azetidinylcarbonyl]-4-(phenylmethyl)piperazine fumarate [1:1]

A stirred solution of 2.9 g (0.01 mole) of 3-(3-bromophenoxy)-1-azetidinecarbonyl chloride in 20 ml of methylene chloride was treated with 3.6 g (0.02 mole) of 1-benzylpiperazine added dropwise. After stirring for 16 hr, the reaction mixture was diluted with 200 ml of water and the methylene chloride layer separated, dried over magnesium sulfate, and concentrated in vacuo to yield a pale amber oil (8.2 g). This residue was dissolved in diethyl ether and treated with 1.2 g of fumaric acid dissolved in 75 ml of boiling isopropyl alcohol. Upon cooling and filtering, the precipitated solid yielded 3.65 g of fine white crystals, m.p. 195°–196° C. Mass spectra data indicate the solid was mainly the fumarate salt of 1-benzylpiperazine. The filtrate was converted to the free base by addition of ammonium hydroxide and extraction with methylene chloride. The extracts were dried and concentrated in vacuo. The residue obtained was chromatographed on a 120 g silica gel column by first eluting with methylene chloride to wash the column then with a methanol/methylene chloride gradient from 0.5% to 2% methanol. The fractions (2–200 ml) which contained the desired product by TLC were combined and concentrated in vacuo to yield 3.5 g of yellow oil. The oil in 25 ml of isopropanol was treated with 1.2 g of fumaric acid and heated until a clear solution was obtained. The volume was reduced to 10 ml under nitrogen and 25 ml of isopropyl ether was added. Upon cooling, filtration yielded 3.3 g (45.1%) of fine white crystals, m.p. 164°–165° C.

Analysis: Calculated for $C_{21}H_{24}BrN_3O_2 \cdot C_4H_4O_4$: C,54.95; H,5.17; N,7.69. Found C,54.94; H,5.16; N,7.70.

EXAMPLE 94

4-(4-Chlorophenyl)-1-[3-[3-(trifluoromethyl)phenoxy]-1-azetidinylcarbonyl]-4-piperidinol A stirred mixture of 2.8 g (0.01 mole) of 3-[3-(trifluoromethyl)phenoxy]-1-azetidinecarbonyl chloride and 1.4 g (0.01 mole) of potassium carbonate in 25 ml of tetrahydrofuran was treated with 2 g (0.01 mole) of 4-(4-chlorophenyl)-4-hydroxypiperidine added in small portions. After stirring for 30 min, a few pieces of ice were added and stirring continued for 16 hr. The reaction mixture was diluted with 200 ml of water and the oil which separated was extracted into methylene chloride (2×50 ml). The combined extracts were dried over magnesium sulfate and concentrated in vacuo to give a water-like oil (5.16 g). A crystalline solid was obtained by cooling to −78° C. and recrystallization was accomplished by dissolving the residue in 5 ml of acetone and 75 ml of isopropyl ether and reducing the volume under nitrogen to 40 ml. Upon cooling, filtration yielded 3.6 g (79.1%) of fine white crystals, m.p. 127°–128.5° C.

Analysis: Calculated for $C_{22}H_{22}F_3ClN_2O_3$: C,58.09; H,4.88 N,6.16. Found: C,57.88; H,4.90; N,6.08.

EXAMPLE 95

When in the procedure of Example 37 and utilizing Method B, substituting the following for 1-propylpiperazine:
(a) 1-(2-methoxyphenyl)piperazine hydrochloride,
(b) 1-(α,α,α-trifluoro-m-tolyl)piperazine,
(c) 2,6-dimethylmorpholine,
(d) 3,5-dimethylmorpholine, and
(e) morpholine
there are obtained:
(a) 1-(2-methoxyphenyl)-4-[3-[3-(trifluoromethyl)-phenoxy]-1-azetidinylcarbonyl]piperazine fumarate,
(b) 1-[3-[3-(trifluoromethyl)phenoxy]-1-azetidinylcarbonyl]-4-[3-(trifluoromethyl)phenyl]piperazine fumarate,
(c) 2,6-dimethyl-4-[3-[3-(trifluoromethyl)phenoxy]-1-azetidinylcarbonyl]morpholine fumarate,
(d) 3,5-dimethyl-4-[3-[3-(trifluoromethyl)phenoxy]-1-azetidinylcarbonyl]morpholine fumarate, and
(e) 4-[3-[3-(trifluoromethyl)phenoxy]-1-azetidinylcarbonyl]morpholine fumarate.

EXAMPLE 96

2-[4-[3-[3-(Trifluoromethyl)phenoxy]-1-azetidinylcarbonyl]-1-piperazinyl]pyrimidine A stirred mixture of 2.8 g (0.01 mole) of 3-[3-(trifluoromethyl)phenoxy]-1-azetidinecarbonyl chloride and 1.4 g (0.01 mole) of potassium carbonate in 25 ml of tetrahydrofuran was treated with 1.6 g (0.01 mole) of 1-(2-pyrimidyl)piperazine added dropwise. After stirring for 30 min, a few pieces of ice were added and stirring continued for 16 hr. The reaction mixture was diluted with 200 ml of water and the oil which separated slowly crystallized. Recrystallization from isopropyl ether yielded 2.7 g (66.3%) of fine white crystals, m.p. 127°–128° C.

Analysis: Calculated for $C_{19}H_{20}F_3N_5O_2$: C,56.20; H,4.95; N,17.19. Found: C,56.01; H,4.94; N,17.15.

EXAMPLE 97

1-(Phenylmethyl)-4-[3-[3-(trifluoromethyl)phenoxy]-1-azetidinylcarbonyl]piperazine fumarate [1:1]

A stirred mixture of 2.8 g (0.01 mole) of 3-[3-(trifluoromethyl)phenoxy]-1-azetidinecarbonyl chloride and 1.4 g (0.01 mole) of potassium carbonate in 25 ml of tetrahydrofuran was treated with 1.8 g (0.01 mole) of 1-benzylpiperazine. After stirring for 30 min, approximately 1 g of ice was added and stirring continued for 16 hr. The reaction mixture was diluted with 200 ml of water and the oil which separated was extracted into methylene chloride (2×50 ml). The combined extracts were dried and concentrated in vacuo to yield 4.7 g of residue. This residue was dissolved in 10 ml of isopropanol and treated with 1.2 g of fumaric acid dissolved in 25 ml of boiling isopropanol. The mixture was concentrated to a pastle-like residue which yielded a solid when triturated with ethyl acetate. Recrystallization from methyl ethyl ketone yielded 5.2 g (97%) of fine white crystals, m.p. 125°–127° C.

Analysis: Calculated for $C_{22}H_{24}F_3N_3O_2 \cdot C_4H_4O_4$: C,58.32; H,5.27; N,7.85. Found: C,58.03; H,5.19; H,7.79.

EXAMPLE 98

3-[(4-Chlorophenyl)thio]-1-azetidinecarboxamide

A stirred solution of 2.6 g (0.01 mole) of 3-[(4-chlorophenyl)thio]-1-azetidinecarbonyl chloride in 20 ml of tetrahydrofuran was treated with 2 ml (0.02 mole) of 57% ammonium hydroxide. The slightly exothermic reaction mixture was stirred for 3 hr as it cooled to ambient temperature then diluted with 200 ml of water. The precipitated product was collected by filtration (2.4 g) and recrystallized from absolute ethanol to yield 2 g (83.3%) of fine white crystals, m.p. 210°–212° C.

Analysis: Calculated for $C_{10}H_{11}ClN_2OS$: C,49.48; H,4.57; N,11.54. Found: C,49.40; H,4.54; N,11.54.

EXAMPLE 99

3-[(4-Chlorophenyl)thio]-N,N-dimethyl-1-azetidinecarboxamide

A solution of 2.6 g (0.01 mole) of 3-[(4-chlorophenyl)thio]-1-azetidinecarbonyl chloride in 20 ml of tetrahydrofuran was stirred while cooling in a water bath and treated with 2.5 ml (0.02 mole) of 40% dimethylamine in water. After stirring for 3 hr, the reaction mixture was diluted with 200 ml of water and the resulting product collected ny filtration (2.6 g). Recrystallization from acetone/isopropyl ether yielded 2 g (74.1%) of fine white crystals, m.p. 96°–97° C.

Analysis: Calculated for $C_{12}H_{15}ClN_2OS$: C,53.23; H,5.58; N,10.35. Found: C,53.25; H,5.65; N,10.35.

EXAMPLE 100

3-[(4-Chlorophenyl)thio]-N-methyl-1-azetidinecarboxamide

A stirred solution of 2.6 g (0.01 mole) of 3-[(4-chlorophenyl)thio]-1-azetidinecarbonyl chloride in 20 ml of tetrahydrofuran was cooled in a water bath and treated with 2 ml (0.02 mole) of 40% methylamine in water. After 3 hr, the reaction mixture was diluted with 200 ml of water and the precipitated product collected by filtration (2.6 g). Recrystallization from benzene/methanol yielded 2.4 g (93.8%) of fine white crystals, m.p. 161°–162° C.

Analysis: Calculated for $C_{11}H_{13}ClN_2OS$: C,51.46; H,5.10; N,10.91. Found: C,51.51; H,5.14; N,10.91.

EXAMPLE 101

3-[(4-Chlorophenyl)thio]-N-(2-propenyl)-1-azetidinecarboxamide

A stirred solution of 2.6 g (0.01 mole) of 3-[(4-chlorophenyl)thio]-1-azetidinecarbonyl chloride in 20 ml of tetrahydrofuran was cooled in a water bath and treated with 2.2 g (0.02 mole) of 2-propenylamine. After stirring for 3 hr, the reaction mixture was diluted with 200 ml of water and the product separated as a yellow oil. The oil slowly solidified to yield a dull orange-red waxy material. After decanting the water and allowing the residue to air dry, the residue was triturated 5 times with boiling isopropyl ether and the decanted solutions upon cooling yielded 5 solid fractions, from white to pale beige color. The fractions were all consistent with the expected product by mass spectral analysis and TLC showed only a single product. All five fractions were combined to give 1.7 g (60.3%), m.p. 88°–89° C.

Analysis: Calculated for $C_{13}H_{15}ClN_2OS$: C,55.22; H,5.35; N,9.91. Found: C,55.26; H,5.38; N,9.92.

EXAMPLE 102

1-[3-[(4-Chlorophenyl)thio]-1-azetidinylcarbonyl]-4-methylpiperazine fumarate [1:1]

A stirred solution of 2.6 g (0.01 mole) of 3-[(4-chlorophenyl)thio]-1-azetidinecarbonyl chloride in 20 ml of tetrahydrofuran was treated with 2 g (0.02 mole) of 1-methylpiperazine. After stirring for 16 hr, the reaction mixture was diluted with 200 ml of water and the milky solution was extracted with methylene chloride (2×50 ml). The combined extracts were treated with 1.2 g of fumaric acid in 25 ml of methanol. The resulting precipitate was collected by filtration (3.1 g) and recrystallized from isopropanol, yielding 2.2 g (49.9%) of fine white crystals, m.p. 173°–174° C.

Analysis: Calculated for $C_{15}H_{20}ClN_3OS \cdot C_4H_4O_4$: C,51.64; H,5.47; N,9.51. Found: C,51.62; H,5.51; N,9.45.

EXAMPLE 103

Octahydro-2-[3-[3-(trifluoromethyl)phenoxy]-1-azetidinylcarbonyl]pyrrolo[1,2-a]pyrazine fumarate [1:1]

A solution of 2.8 g (0.01 mole) of 3-[3-(trifluoromethyl)phenoxy]-1-azetidinecarbonyl chloride in 20 ml of tetrahydrofuran was stirred with 1.4 g (0.01 mole) of potassium carbonate then treated with the dropwise addition of 1.3 g (0.01 mole) of 1,4-diazabicyclo(4.3.0-)nonane. After stirring for 30 minutes, approximately 2 g of ice was added and stirring continued for 64 hr. The reaction mixture was diluted with 200 ml of water and the oil which separated was extracted into methylene chloride (2×50 ml), dried over magnesium sulfate and concentrated in vacuo to a pale yellow oil (3.9 g). This oil was placed in 20 ml of isopropanol and treated with 1.2 g of fumaric acid and heated to give a clear solution. The solvent was removed in vacuo and the residue crystallized on standing. The residue was recrystallized from ethyl acetate with 5% isopropyl ether and from methyl isobutyl ketone to yield 2.5 g (51.5%) of beige colored crystals, m.p. 102°–110° C.

Analysis: Calculated for $C_{18}H_{22}F_3N_3O_2 \cdot C_4H_4O_4$: C,54.43; H,5.40; N,8.66. Found: C,54.40; H,5.37; N,8.62.

EXAMPLE 104

1-[3-[(4-Fluorophenoxy)-1-azetidinylcarbonyl]piperazine fumarate [1:1]

A solution of 7.3 g (0.02 mole) of 4-[3-(4-fluorophenoxy)-1-azetidinylcarbonyl]-1-(phenylmethyl)piperazine in 150 ml of ethanol was treated with 1 ml of triethylamine and 0.7 g of 5% palladium on carbon catalyst and hydrogenated on a Parr apparatus for 5 hr at 70° C. After cooling, the catalyst was removed by filtration and the filtrate concentrated in vacuo to a pale yellow oil (7 g). The oil solidified and a sample was recrystallized from isopropyl ether, m.p. 95°–97° C. A portion of the free base was converted to the fumarate salt and recrystallized from methyl isobutyl ketone yielding 4.7 g of gray solid. A second recrystallization with charcoal treatment from isopropanol yielded 3.8 g of white crystals, m.p. 161°–162° C.

Analysis: Calculated for $C_{14}H_{18}FN_3O_2 \cdot C_4H_4O_4$: C,54.68; H,5.61; N,10.63. Found: C,54.50; H,5.61; N,10.60.

EXAMPLE 105

Hexahydro-1-methyl-4-[3-[3-(trifluoromethyl)phenoxy]-1-azetidinylcarbonyl]-1H-1,4-diazepine fumarate [1:1]

A stirred mixture of 2.8 g (0.01 mole) of 3-[3-(trifluoromethyl)phenoxy]-1-azetidinecarbonyl chloride and 1.4 g (0.01 mole) of potassium carbonate in 20 ml of tetrahydrofuran was treated with 1.15 g (0.01 mole) of 1-methylhomopiperazine, and after stirring for 15 minutes a small piece of ice was added. After stirring for 16 hr the reaction mixture was diluted with 200 ml of water and the oil which separated was extracted into methylene chloride (2×50 ml). The combined extracts were dried over magnesium sulfate and concentrated in vacuo. The residue (3.8 g) was treated with 1.2 g of fumaric acid and dissolved in 20 ml of isopropanol by heating. Upon cooling, the precipitated solid was collected by filtration to yield 4.1 g (86.6%) of white crystals, m.p. 131°–133° C.

Analysis: Calculated for $C_{17}H_{22}F_3N_3O_2 \cdot C_4H_4O_4$: C,53.28; H,5.54; N,8.88. Found: C,53.18; H,5.56; N,8.83.

EXAMPLE 106

Cis-N,2-Dimethyl-3-[3-(trifluoromethyl)phenoxy]-1-azetidinecarboxamide

A solution of 4.02 g (0.01 mole) of crude (73%) 2-methyl-3-[3-(trifluoromethyl)phenoxy]-1-azetidinecarbonyl chloride cis isomer in 20 ml of tetrahydrofuran was treated while stirring with 1.6 g (0.02 mole) of 40% aqueous monomethylamine. After stirring for 6 hr, the reaction mixture was diluted with 100 ml of water and the oil which separated was extracted into methylene chloride (2×50 ml). The combined extracts were dried over magnesium sulfate and concentrated in vacuo (4.2 g). The oil solidified on standing and was recrystallized from isooctane with a trace of benzene to give 2.6 g (90.3%) of white crystalline product, m.p. 89°–91° C.

Analysis: Calculated for $C_{13}H_{15}F_3N_2O_2$: C,54.17; H,5.25; N,9.72. Found: C,54.54; H,5.28; N,9.58.

EXAMPLE 107

Cis-2-Methyl-N-(2-propenyl)-3-[3-(trifluoromethyl)phenoxy]-1-azetidinecarboxamide A stirred mixture of 4.02 g (0.01 mole) of crude (73%) 2-methyl-3-[3-(trifluoromethyl)phenoxy]-1-azetidinecarbonyl chloride cis isomer and 1.4 g (0.01 mole) of potassium carbonate in 20 ml of tetrahydrofuran was treated with 0.57 g (0.01 mole) of 2-propenylamine. After stirring for 15 minutes, a small piece of ice was added and stirring continued for 3 hr. The reaction mixture was diluted with water and the oil which separated was extracted with methylene chloride (2×50 ml). The combined extracts were dried over magnesium sulfate and concentrated in vacuo (5.2 g). The crude product was chromatographed on a 125 g silica gel column. Elution with chloroform washed impurities from the column and the product was removed by eluting with an ethyl acetate/chloroform gradient (1–20%). The combined product fractions gave a pale yellow oil which solidified on standing and was recrystallized from isopropyl ether/hexane to give an oil which slowly crystallized, yielding 2.1 g (67.8%) of white product, m.p. 74°–77° C.

Analysis: Calculated for $C_{15}H_{17}F_3N_2O_2$: C,57.32; H,5.45; N,8.91. Found: C,57.30; H,5.40; N,8.91.

EXAMPLE 108

Cis-2-Methyl-3-[3-(trifluoromethyl)phenoxy]-1-azetidinecarboxamide

A solution of 4.02 g (0.01 mole) of crude (73%) 2-methyl-3-[3-(trifluoromethyl)phenoxy]-1-azetidinecarbonyl chloride cis isomer in 20 ml of tetrahydrofuran was treated while stirring with 2 ml (0.02 mole) of 57% aqueous ammonium hydroxide. After stirring for 6 hr, the reaction mixture was diluted with 100 ml of water and the oil which separated was extracted into methylene chloride (2×50 ml). The combined extracts were dried over magnesium sulfate and concentrated in vacuo to give 4.2 g. A sample of the oil crystallized at −78° C. and was used to seed the bulk of the material. The resulting solid was recrystallized from benzene/isooctane to yield 2.35 g (87%) of white crystalline product, m.p. 107°-108° C.

Analysis: Calculated for $C_{12}H_{13}F_3N_2O_2$: C,52.56; H,4.78; N,10.22. Found: C,52.61; H,4.60; N,10.11.

EXAMPLE 109

N-Methyl-N-(2-propenyl)-3-[3-(trifluoromethyl)phenoxy]-1-azetidinecarboxamide hydrate [1:0.5]

A stirred mixture of 2.8 g (0.01 mole) of 3-[3-(trifluoromethyl)phenoxy]-1-azetidinecarbonyl chloride and 1.4 g (0.01 mole) of potassium carbonate in 20 ml of tetrahydrofuran was treated with 0.72 g (0.01 mole) of N-methylallylamine. After stirring for 15 minutes, a piece of ice was added and stirring continued for 15 hr. The reaction mixture was diluted with water and the oil which separated was extracted into methylene chloride (2×50 ml). The combined extracts were dried over magnesium sulfate and concentrated in vacuo (3.7 g). The crude oil was chromatographed on a 75 g silica gel column by eluting with chloroform. After the first crude material was washed from the column the three product fractions were combined and concentrated in vacuo, to yield 3 g (97%) of water-like oil.

Analysis: Calculated for $C_{15}H_{17}F_3N_2O_2 \cdot \frac{1}{2}H_2O$: C,55.73; H,5.62; N,8.66. Found: C,55.75; H,5.28; N,8.65.

EXAMPLE 110

3-(3-Methoxyphenoxy)-N-methyl-1-azetidinecarboxamide

A solution of 4.8 g (0.02 mole) of 3-(3-methoxyphenoxy)-1-azetidinecarbonyl chloride in 20 ml of tetrahydrofuran was treated with 4.7 g (0.06 mole) of 40% aqueous monomethylamine and stirred for 16 hrs. The reaction mixture was diluted with 200 ml of water and the oil which separated was extracted into methylene chloride (2×50 ml). The extracts were dried by passing through Whatman phase separating paper and concentrated in vacuo (3.85 g). The residue was purified by chromatography on two 4 mm (silica gel) chromatotron plate by eluting with an ethyl acetate/methylene chloride gradient to give 0.98 g (21%) of tan solid. Recrystallization from benzene with a trace of ligroin yielded 600 mg of tan crystalline powder, m.p. 109°-111° C.

Analysis: Calculated for $C_{12}H_{16}N_2O_3$: C,61.00; H,6.83; N,11.86. Found: C,61.85; H,6.87; N,11.46.

EXAMPLE 111

4-[3-(4-Fluorophenoxy)-1-azetidinylcarbonyl]-1-piperazinecarboxylic acid ethyl ester A stirred mixture of 2.8 g (0.01 mole) of 1-[3-(4-fluorophenoxy)-1-azetidinylcarbonyl]piperazine and 1.4 g (0.01 mole) of potassium carbonate in 20 ml of tetrahydrofuran was treated with 1.1 g (0.01 mole) of ethyl chloroformate. After stirring for 15 minutes, a small piece of ice was added and stirring continued for 72 hr. The reaction mixture was diluted with water and the oil which separated solidified on standing. The solid residue was purified by column chromatography (silica gel; washed with chloroform and eluted with ethyl acetate) to give the product 2.5 g (71%) which was recrystallized from benzene/ligroin to yield 2.35 g (66.7%) of white crystalline product, m.p. 89°-90° C.

Analysis: Calculated for $C_{17}H_{22}FN_3O_4$: C,58.11; H,6.31; N,11.96. Found: C,58.29; H,6.49; N,11.87.

TABLE 1

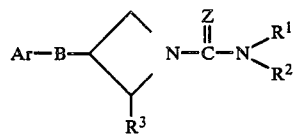

| Ex. No. | Ar | B | $R^3$ | Z | $-NR^1R^2$ | Salt | Geometric Isomer |
|---|---|---|---|---|---|---|---|
| 1 | 3-$CF_3$—$C_6H_4$— | O | H | S | —$NHCH_3$ | — | — |
| 2 | 3-$CF_3$—$C_6H_4$— | O | H | S | —$NH[2,6-(CH_3)_2$—$C_6H_3$—] | — | — |
| 3 | 3-$CF_3$—$C_6H_4$— | O | H | O | —$NH[$—$CH_2$—$C_6H_5]$ | — | — |
| 4 | 3-$CF_3$—$C_6H_4$— | O | H | S | —$NH[2,6-(Cl)_2\ C_6H_3$—] | — | — |
| 5 | 3-$CF_3$—$C_6H_4$— | O | H | S | —$NH[$—$(CH_2)_3$—$N($—$C_2H_5)_2]$ | oxalate [1:1] | — |
| 6 | 3-$CF_3$—$C_6H_4$— | O | H | S | —$NH[$—$(CH_2)_3$—$N(CH_3)_2]$ | — | — |
| 7 | 3-$CF_3$—$C_6H_4$— | O | H | O | —$NH[$—$CH_2$—$CH$=$CH_2]$ | — | — |
| 8 | 3-$CF_3$—$C_6H_4$— | O | H | O | cyclopropylamino | — | — |
| 9 | 3-$CF_3$—$C_6H_4$— | O | H | O | —$NH[$—$(CH_2)_3$—$N(C_2H_5)_2]$ | oxalate [1:1.5] | — |
| 10 | 4-$CF_3$—$C_6H_4$— | O | H | O | —$NH[$—$CH_2$—$CH$=$CH_2]$ | — | — |
| 11 | 3-$CF_3$—$C_6H_4$— | O | H | O | (cyclopropylmethyl)amino | — | — |
| 12 | 3-$CF_3$—$C_6H_4$— | O | H | O | —$N(C_2H_5)_2$ | — | — |
| 13 | 3-$CF_3$—$C_6H_4$— | O | H | O | —$N(CH_3)_2$ | — | — |
| 14 | 3-$CF_3$—$C_6H_4$— | O | H | O | —$NH($—$CH_2$—$C$≡$CH)$ | — | — |
| 15 | 3-$CF_3$—$C_6H_4$— | O | H | O | cyclohexylamino | — | — |
| 16 | 4-$CF_3$—$C_6H_4$— | O | H | O | cyclopropylamino | — | — |
| 17 | 4-$CF_3$—$C_6H_4$— | O | H | O | (cyclopropylmethyl)amino | — | — |
| 18 | 4-$CF_3$—$C_6H_4$— | O | H | S | —$NH[$—$(CH_2)_3$—$N($—$C_2H_5)_2]$ | — | — |
| 19 | 4-$CF_3$—$C_6H_4$— | O | H | O | —$NH[$—$(CH_2)_3$—$N($—$C_2H_5)_2]$ | oxalate [1:2] | — |
| 20 | 4-$CF_3$—$C_6H_4$— | O | H | O | —$NH($—$CH_2$—$C$≡$CH)$ | — | — |

TABLE 1-continued $$\text{Ar}-\text{B}-\overset{\overset{\displaystyle Z}{\parallel}}{\underset{\underset{\displaystyle R^3}{|}}{\text{N}-\text{C}-\text{N}}}\overset{R^1}{\underset{R^2}{}}$$

| Ex. No. | Ar | B | R³ | Z | —NR¹R² | Salt | Geometric Isomer |
|---|---|---|---|---|---|---|---|
| 21 | 4-CF₃—C₆H₄— | O | H | O | —NH[—CH₂—C(—CH₃)(=CH₂)] | — | — |
| 22 | 3-CF₃—C₆H₄— | O | H | O | —NH[—CH₂—C(—CH₃)(=CH₂)] | — | — |
| 23 | 4-CF₃—C₆H₄— | O | H | O | —NH[—CH₂—CH=C(CH₃)₂] | — | — |
| 24 | 3-CF₃—C₆H₄— | O | H | O | —NH[—CH₂—CH=C(CH₃)₂] | — | — |
| 25 | 4-CF₃—C₆H₄— | O | H | O | —NH(—CH₂—CH=CH—CH₃) | — | E |
| 26 | 3-CF₃—C₆H₄— | O | H | O | —NH(—CH₂—CH=CH—CH₃) | — | E |
| 27 | 3-CF₃—C₆H₄— | O | H | O | —NH(—C₆H₅) | — | — |
| 28 | 4-CF₃—C₆H₄— | O | H | O | —NH(—C₆H₅) | — | — |
| 29 | 3-CF₃—C₆H₄— | O | —CH₃ | O | —NH(—CH₃) | — | Trans |
| 30 | 3-CF₃—C₆H₄— | O | —CH₃ | O | —NH₂ | — | Trans |
| 31 | 3-CF₃—C₆H₄— | O | —CH₃ | O | —NH(—CH₂—CH=CH₂) | — | Trans |
| 32 | 3-Cl—C₆H₄— | O | H | O | —NH(—CH₃) | — | — |
| 33 | 3-Cl—C₆H₄— | O | H | O | —NH(—CH₂—CH=CH₂) | — | — |
| 34 | pyridin-2-yl | O | H | O | —NH(—CH₃) | — | — |
| 35 | pyridin-2-yl | O | H | O | —NH(—CH₂—CH=CH₂) | — | — |
| 36 | pyridin-2-yl | O | H | O | —NH₂ | — | — |
| 37 | 3-CF₃—C₆H₄— | O | H | O | 4-(1-propyl)-1-piperazinyl | fumarate [1:1] | — |
| 38 | 4-CF₃—C₆H₄— | O | H | O | 1H-imidazole | — | — |
| 39 | 3-Cl—C₆H₄— | O | H | O | —NH₂ | — | — |
| 40 | 3-F—C₆H₄— | O | H | O | —NH(—CH₃) | — | — |
| 41 | 3-F—C₆H₄— | O | H | O | —NH₂ | — | — |
| 42 | 3-CF₃—C₆H₄— | O | H | O | 1-homopiperidinyl | — | — |
| 43 | 3-CF₃—C₆H₄— | O | H | O | 1-piperidinyl | — | — |
| 44 | 3-CF₃—C₆H₄— | O | H | O | 1-azetidine | — | — |
| 45 | 3-CF₃—C₆H₄— | O | H | O | 1-pyrrolidine | — | — |
| 46 | 3-CF₃—C₆H₄— | O | H | O | —N(—CH₃)(—CH₂—CH≡CH) | — | — |
| 47 | 3-CF₃—C₆H₄— | O | H | O | 4-methyl-1-piperazinyl | oxalate [1:1.5] | — |
| 48 | 3-CF₃—C₆H₄— | O | H | O | 4-methyl-1-piperazinyl | fumarate [1:1] | — |
| 49 | 3-CF₃—C₆H₄— | O | H | O | —NH(4-CH₃—C₆H₄—) | — | — |
| 50 | 3-CF₃—C₆H₄— | O | H | O | —NH(4-Cl—C₆H₄—) | — | — |
| 51 | 4-F—C₆H₄— | O | H | O | —NH(—CH₃) | — | — |
| 52 | 4-F—C₆H₄— | O | H | O | —NH₂ | — | — |
| 53 | 4-F—C₆H₄— | O | H | O | —NH(—CH₂—CH=CH₂) | — | — |
| 54 | 4-F—C₆H₄— | O | H | O | —NH(—CH₂—C≡CH) | — | — |
| 55 | 3,4-(Cl)₂—C₆H₃— | O | H | O | —NH(—CH₃) | — | — |
| 56 | 3,4-(Cl)₂—C₆H₃— | O | H | O | —NH(—CH₂—CH=CH₂) | — | — |
| 57 | 3,4-(Cl)₂—C₆H₃— | O | H | O | —NH(—CH₂—C≡CH) | — | — |
| 58 | 4-Cl—C₆H₄— | O | H | O | —NH(—CH₂—C≡CH) | — | — |
| 59 | 3-Br—C₆H₄— | O | H | O | —NH₂ | — | — |
| 60 | 3-Br—C₆H₄— | O | H | O | —NH(—CH₃) | — | — |
| 61 | 3-Br—C₆H₄— | O | H | O | —NH(—CH₂—CH=CH₂) | — | — |
| 62 | 3,4-(Cl)₂—C₆H₃— | O | H | O | —NH₂ | — | — |
| 63 | 4-Cl—C₆H₄— | O | H | O | —NH₂ | — | — |
| 64 | 4-Cl—C₆H₄— | O | H | O | —NH(—CH₃) | — | — |
| 65 | 4-Cl—C₆H₄— | O | H | O | —NH(—CH₂—CH=CH₂) | — | — |
| 66 | 3-Br—C₆H₄— | O | H | O | —NH(—CH₂—C≡CH) | — | — |
| 67 | 4-Br—C₆H₄— | O | H | O | —NH(—CH₂—CH=CH₂) | — | — |
| 68 | 4-Br—C₆H₄— | O | H | O | —NH₂ | — | — |
| 69 | 4-Br—C₆H₄— | O | H | O | —NH(—CH₃) | — | — |
| 70 | 4-Br—C₆H₄— | O | H | O | —NH(—CH₂—C≡CH) | — | — |
| 71 | 3-CH₃—C₆H₄— | O | H | O | —NH₂ | — | — |
| 72 | 3-CH₃—C₆H₄— | O | H | O | —NH(—CH₂—CH=CH₂) | — | — |
| 73 | 3-CH₃—C₆H₄— | O | H | O | —NH(—CH₂—C≡CH) | — | — |
| 74 | 3-(OCH₃)—C₆H₄— | O | H | O | —NH(—CH₂—CH=CH₂) | — | — |
| 75 | 3-(OCH₃)—C₆H₄— | O | H | O | —NH(—CH₂—C≡CH) | — | — |
| 76 | 3-CH₃—C₆H₄— | O | H | O | —NH(—CH₃) | — | — |
| 77 | C₆H₅— | O | H | O | —NH₂ | — | — |
| 78 | 4-Br—C₆H₄— | O | H | O | 4-phenyl-1-piperazinyl | — | — |
| 79 | 4-Br—C₆H₄— | O | H | O | 4-(phenylmethyl)-1-piperazinyl | — | — |
| 80 | 4-Br—C₆H₄— | O | H | O | 4-methyl-1-piperazinyl | fumarate [1:1] | — |
| 81 | 3-Br—C₆H₄— | O | H | O | 4-methyl-1-piperazinyl | fumarate [1:1] | — |
| 82 | 4-F—C₆H₄— | O | H | O | 4-methyl-1-piperazinyl | fumarate [1:1] | — |
| 83 | 4-F—C₆H₄— | O | H | O | 4-phenyl-1-piperazinyl | — | — |
| 84 | 4-F—C₆H₄— | O | H | O | 4-(phenylmethyl)-1-piperazinyl | — | — |
| 85 | 4-F—C₆H₄— | O | H | O | 4-(phenylmethyl)-1-piperazinyl | fumarate [1:1] | — |
| 86 | 3,4-(Cl)₂—C₆H₃— | O | H | O | 4-methyl-1-piperazinyl | fumarate [1:1] | — |
| 87 | 3,4-(Cl)₂—C₆H₃— | O | H | O | 4-(phenylmethyl)-1-piperazinyl | fumarate [1:1] | — |
| 88 | 3-CF₃—C₆H₄— | O | H | O | 4-phenyl-1-piperazinyl | — | — |
| 89 | 3-CF₃—C₆H₄— | O | H | O | 4-(2-pyridinyl)-1-piperazinyl | — | — |
| 90 | 3-CF₃—C₆H₄— | O | H | O | 4-phenyl-1-piperidinyl | — | — |
| 91 | 3-CF₃—C₆H₄— | O | H | O | 1,2,3,6-tetrahydro-4-phenyl-1-pyridinyl | — | — |
| 92 | 3,4-(Cl)₂—C₆H₃— | O | H | O | 4-(2-pyridinyl)-1-piperazinyl | — | — |

TABLE 1-continued

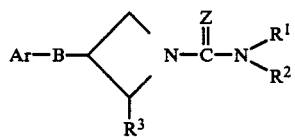

| Ex. No. | Ar | B | R³ | Z | —NR¹R² | Salt | Geometric Isomer |
|---|---|---|---|---|---|---|---|
| 93 | 3-Br—C₆H₄— | O | H | O | 4-(phenylmethyl)-1-piperazinyl | fumarate [1:1] | — |
| 94 | 3-CF₃—C₆H₄— | O | H | O | 4-(4-Cl—C₆H₄—)-4-(OH)-1-piperidinyl | — | — |
| 95a | 3-CF₃—C₆H₄— | O | H | O | 4-[2-(OCH₃)C₆H₄—]-1-piperazinyl | fumarate | — |
| 95b | 3-CF₃—C₆H₄— | O | H | O | 4-[3-(CF₃)—C₆H₄—]-1-piperazinyl | fumarate | — |
| 95c | 3-CF₃—C₆H₄— | O | H | O | 2,6-(CH₃)₂-4-morpholinyl | — | — |
| 95d | 3-CF₃—C₆H₄— | O | H | O | 3,5-(CH₃)₂-4-morpholinyl | — | — |
| 95e | 3-CF₃—C₆H₄— | O | H | O | 4-morpholinyl | — | — |
| 96 | 3-CF₃—C₆H₄— | O | H | O | 4-(2-pyrimidine)-1-piperazinyl | — | — |
| 97 | 3-CF₃—C₆H₄— | O | H | O | 4-(phenylmethyl)-1-piperazinyl | fumarate [1:1] | — |
| 98 | 4-Cl—C₆H₄— | S | H | O | —NH₂ | — | — |
| 99 | 4-Cl—C₆H₄— | S | H | O | —N(—CH₃)₂ | — | — |
| 100 | 4-Cl—C₆H₄— | S | H | O | —NH(—CH₃) | — | — |
| 101 | 4-Cl—C₆H₄— | S | H | O | —NH(—CH₂—CH=CH₂) | — | 13 |
| 102 | 4-Cl—C₆H₄— | S | H | O | 4-methyl-1-piperazinyl | fumarate [1:1] | — |
| 103 | 3-CF₃—C₆H₄— | O | H | O | (octahydropyrrolo structure) | fumarate [1:1] | — |
| 104 | 4-F—C₆H₄— | O | H | O | 1-piperazinyl | fumarate [1:1] | — |
| 105 | 3-CF₃—C₆H₄— | O | H | O | 4-methyl-1-homopiperazinyl | fumarate [1:1] | — |
| 106 | 3-CF₃—C₆H₄— | O | —CH₃ | O | —NH(—CH₃) | — | cis |
| 107 | 3-CF₃—C₆H₄— | O | —CH₃ | O | —NH(—CH₂—CH=CH₂) | — | cis |
| 108 | 3-CF₃—C₆H₄— | O | —CH₃ | O | —NH₂ | — | cis |
| 109 | 3-CF₃—C₆H₄— | O | H | O | —N(—CH₃)(—CH₂—CH=CH₂) | hydrate [1:0.5] | — |
| 110 | 3-(O—CH₃)—C₆H₄ | O | H | O | —NH(—CH₃) | — | — |
| 111 | 4-F—C₆H₄— | O | H | O | 4-(—C(O)OC₂H₅)-1-piperazinyl | — | — |

PHARMACOLOGY

Anticonvulsant activity was determined for compounds of Formula I as evidenced by using chemical or electrical challenge as follows.

Metrazole Chemical Challenge (Swinyard Method)

Groups of 8 adult female mice were randomly assigned to dosage groups according to the method of Steel, R. G. D., and Torrie, J. H. (1960) in "Principles and Procedures of Statistics", McGraw-Hill Book Company, Inc., pp 99–100, pp 428–31. Each mouse was identified with a color code on its tail. The test compounds were administered as solutions or suspensions in 10 ml/kg mouse body weight of 0.5% aqueous methyl cellulose within 15 minutes of preparation of the suspension. Metrazole ®(pentylenetetrazol) was prepared as a solution in physiological saline. The mice were not fasted prior to the test. Eight mice were tested at each dosage level.

Each mouse received one dose of the test drug (usually 100 mg/kg for screening) in the 0.5% aqueous methylcellulose or the control article (0.5% aqueous methylcellulose alone) intraperitoneally. Metrazole (80 mg/kg S.C.) was then given in a loose fold of skin on the back of the neck; i.e., ½ hr after the test compound or control article was given. Injections were given with a 1 ml glass tuberculin syringe with appropriate size hypodermic needle (27 gauge for solutions; 23 gauge for suspensions). All injections were given in a volume of 10 ml/kg mouse body weight. Each mouse was observed for 30 minutes following Metrazol injection. Failure of the animals to exhibit a threshold seizure (a single episode of clonic spasms at least 5 seconds in duration) was defined as protection. Anticonvulsant data were tabulated as the percent protection, i.e., $$\frac{\text{No. Mice Protected}}{\text{No. Mice Tested}} \times 100.$$

The ED₅₀, 95% confidence limits and potency ratio may be ascertained by the computer-based probit analysis ascribed to Finney, D. J. (1964) *Statistical Method in Biological Assay*, 2nd Ed., New York. Hefner Publishing Co.

ELECTRICAL CHALLENGE

Adult female mice in groups of eight were administered the test drug intraperitoneally (usually 100 mg/kg initially for screening) in liquid carrier, usually physiological saline or water. Animals were challenged electrically by placing brass electrodes on the corneas and applying an electrical stimulus (60 Hz, 5 m sec. pulse width, 34 m A intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The ED₅₀, 95% confidence limits and potency ratio may be ascertained by the method of J. T. Litchfield and F. Wilcoxon (1949) J. PHARMACOL. EXP. THER. 96, 99–113.

Some of the more active compounds such as in Examples 7, 8, 10, 14, 16 and 20 exhibit $ED_{50}$'s in the metrazole test of 5 to 30 mg/kg and $ED_{50}$'s in the electrical challenge test of about 10 to 30 mg/kg.

FORMULATION AND ADMINISTRATION

The pharmacologically active 3-aryloxy and 3-arylthio-1-azetidinecarboxamides of this invention are effective in the treatment of both petit mal epilepsy and grand mal epilepsy. Effective quantities of these compounds may be administered to a living animal body orally as in capsules, tablets or elixirs. It is only necessary that the active ingredient constitute an effective amount, i.e., such that a suitable effective dosage will be obtained consistent with the dosage form employed. The exact individual dosage as well as daily dosages will, of course, be determined according to standard medical principles under the direction of a physician or veterinarian.

Based upon a comparison with known anticonvulsant compounds, daily dosages appear to preferably range from about 0.5 to 1.5 milligrams per kilogram of body weight in the treatment of petit mal epilepsy and about 25 to 35 milligrams per kilogram of body weight in the treatment of grand mal epilepsy. Very small quantities of the active materials of the present invention, even as low as 0.1 milligram, are effective when minor therapy is involved. Unit dosages are usually 5 milligrams or above and preferably 25, 50 or 100 milligrams per unit dose. The active ingredients of the invention may be combined with other pharmacologically active agents as previously indicated, or with buffers, antacids or the like, for administration and the proportion of the active agent in the composition may be varied widely.

CAPSULES

Capsules of 5 mg., 25 mg., and 50 mg. of active ingredient per capsule are prepared; with higher amounts of ingredient reduction may be made in the amount of lactose.

| Typical blend for encapsulation | Per Capsule, mg. |
| --- | --- |
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

Additional capsule formulations preferably contain a higher dose of active ingredient and are as follows:

| Ingredients | 100 mg. per Capsule | 250 mg. per Capsule | 500 mg. per Capsule |
| --- | --- | --- | --- |
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total, mg. | 435.0 | 435.0 | 550.0 |

TABLETS

A typical formulation for a tablet containing 5.0 mg. of active ingredient per tablet follows. The formulation may be used for other strengths of active ingredient by adjustment of weight of dicalcium phosphate.

| Ingredients | Per Tablet, mg. |
| --- | --- |
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows.

| 50 mg. Tablet | |
| --- | --- |
| Ingredients | Per Tablet, mg. |
| Active ingredient | 50.0 |
| Lactose | 90.0 |
| Corn starch | 58.0 |
| Calcium stearate | 2.0 |
| Total | 200.0 |

Uniformly blend the active ingredient, lactose, and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

What is claimed is:

1. A method of treatment for anticonvulsant effect which comprises administering to a mammal in need thereof an effective amount of a 3-aryloxyazetidinecarboxamide or 3-arylthioazetidinecarboxamide compound selected from the group having the formula:

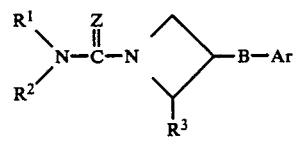

wherein:
Ar is selected from pyridyl in any of its positions optionally substituted by halo, from phenyl or phenyl substituted by 1 or 2 groups selected from chloro, bromo, iodo, fluoro, loweralkyl, loweralkoxy, nitro, aminocarbonyl, or trifluoromethyl;
B is oxygen or sulfur;
Z is oxygen or sulfur;
$R^1$ and $R^2$ may be the same or different and are selected from hydrogen, loweralkyl, aryl, allyl, substituted allyl, propargyl, cycloalkyl (3-9C), lower alkylcycloalkyl, cycloalkylloweralkyl, arylloweralkyl, and diloweralkylaminoloweralkyl, and $R^1$ and $R^2$ when taken together with the adjacent nitrogen atom may form a heterocyclic amino group selected from azetidinyl, pyrrolidinyl, piperidinyl, homopiperidinyl, imidazolyl, piperazinyl, (halophenyl)piperidinyl, phenyl-1,2,3,6-tetrahydropyridin-1-yl, phenylpiperidin-1-yl, hydroxypiperidin-1-yl, 4-morpholino, 4-(3,5-diloweralkyl)morpholino, 1,2,3,6-tetrahydropyridin-1-yl, (halophenyl)(hydroxy)piperidin-1-yl, 4-(2,6-diloweralkyl)morpholino, pyrrolo[1,2-a]pyrazin-2-yl, homopiperazinyl, 4-substituted piperazinyl, and 4-substituted homopiperazinyl;

$R^3$ is selected from hydrogen, loweralkyl, aryl or arylloweralkyl; the geometrical isomers thereof, and the pharmaceutically acceptable acid addition salts thereof when $R^1$ and/or $R^2$ have one or more salt-forming basic amino components or when Ar is pyridyl, and the hydrates thereof, with the proviso that when $R^3$ is hydrogen, Z is oxygen, B is oxygen, and Ar is phenyl or phenyl substituted by trifluoromethyl, aminocarbonyl, dichloro, chloro, fluoro, bromo, or methyl, then $R^1$ and $R^2$ cannot be a combination of hydrogen and loweralkyl, or cannot both be hydrogen, methyl, or ethyl.

2. The method of claim 1 wherein the compound is N-(2,6-dimethylphenyl)-3-[3-(trifluoromethyl)phenoxy]-1-azetidinecarbothioamide.

3. The method of claim 1 wherein the compound is N-(phenylmethyl)-3-[3-(trifluoromethyl)phenoxy]-1-azetidinecarboxamide.

4. The method of claim 1 wherein the compound is N-(2,6-dichlorophenyl)-3-[3-(trifluoromethyl)phenoxy]-1-azetidinecarbothioamide.

5. The method of claim 1 wherein the compound is N-[3-(diethylamino)propyl]-3-[3-(trifluoromethyl)phenoxy]-1-azetidinecarbothioamide or a pharmaceutically acceptable acid addition salt thereof.

6. The method of claim 1 wherein the compound is N-[3-(dimethylamino)propyl]-3-[3-(trifluoromethyl)phenoxy]-1-azetidinecarbothioamide or a pharmaceutically acceptable acid addition salt thereof.

7. The method of claim 1 wherein the compound is N-(2-propenyl)-3-[3-(trifluoromethyl)phenoxy]-1-azetidinecarboxamide.

8. The method of claim 1 wherein the compound is N-cyclopropyl-3-[3-(trifluoromethyl)phenoxy]-1-azetidinecarboxamide.

9. The method of claim 1 wherein the compound is N-[3-(diethylamino)propyl]-3-[3-(trifluoromethyl)phenoxy]-1-azetidinecarboxamide or a pharmaceutically acceptable acid addition salt thereof.

10. The method of claim 1 wherein the compound is N-(2-propenyl)-3-[4-(trifluoromethyl)phenoxy]-1-azetidinecarboxamide.

11. The method of claim 1 wherein the compound is N-(cyclopropylmethyl)-3-[3-(trifluoromethyl)phenoxy]-1-azetidinecarboxamide.

12. The method of claim 1 wherein the compound is N-(2-propynyl)-3-[3-(trifluoromethyl)phenoxy]-1-azetidinecarboxamide.

13. The method of claim 1 wherein the compound is N-cyclohexyl-3-[3-(trifluoromethyl)phenoxy]-1-azetidinecarboxamide.

14. The method of claim 1 wherein the compound is N-cyclopropyl-3-[4-(trifluoromethyl)phenoxy]-1-azetidinecarboxamide.

15. The method of claim 1 wherein the compound is N-(cyclopropylmethyl)-3-[4-(trifluoromethyl)phenoxy]-1-azetidinecarboxamide.

16. The method of claim 1 wherein the compound is N-[3-(diethylamino)propyl]-3-[4-(trifluoromethyl)phenoxy]-1-azetidinecarbothioamide or a pharmaceutically acceptable acid addition salt thereof.

17. The method of claim 1 wherein the compound is N-[3-(diethylamino)propyl]-3-[4-(trifluoromethyl)phenoxy]-1-azetidinecarboxamide or a pharmaceutically acceptable acid addition salt thereof.

18. The method of claim 1 wherein the compound is N-(2-propynyl)-3-[4-(trifluoromethyl)phenoxy]-1-azetidinecarboxamide.

19. The method of claim 1 wherein the compound is N-(2-methyl-2-propenyl)-3-[4-(trifluoromethyl)phenoxy]-1-azetidinecarboxamide.

20. The method of claim 1 wherein the compound is N-(2-methyl-2-propenyl)-3-[3-(trifluoromethyl)phenoxy-1-azetidinecarboxamide.

21. The method of claim 1 wherein the compound is N-(3-methyl-2-butenyl)-3-[4-(trifluoromethyl)phenoxy]-1-azetidinecarboxamide.

22. The method of claim 1 wherein the compound is N-(3-methyl-2-butenyl)-3-[3-(trifluoromethyl)phenoxy]-1-azetidinecarboxamide.

23. The method of claim 1 wherein the compound is (E)-N-(2-butenyl)-3-[4-(trifluoromethyl)phenoxy]-1-azetidinecarboxamide.

24. The method of claim 1 wherein the compound is (E)-N-(2-butenyl)-3-[3-(trifluoromethyl)phenoxy]-1-azetidinecarboxamide.

25. The method of claim 1 wherein the compound is N-phenyl-3-[3-(trifluoromethyl)phenoxy]-1-azetidinecarboxamide.

26. The method of claim 1 wherein the compound is N-phenyl-3-[4-(trifluoromethyl)phenoxy]-1-azetidinecarboxamide.

27. The method of claim 1 wherein the compound is trans-2-methyl-N-(2-propenyl)-3-[3-(trifluoromethyl)phenoxy]-1-azetidinecarboxamide.

28. The method of claim 1 wherein the compound is 3-(3-chlorophenoxy)-N-(2-propenyl)-1-azetidinecarboxamide.

29. The method of claim 1 wherein the compound is N-methyl-3-(2-pyridinyloxy)-1-azetidinecarboxamide or a pharmaceutically acceptable acid addition salt thereof.

30. The method of claim 1 wherein the compound is N-(2-propenyl)-3-(2-pyridinyloxy)-1-azetidinecarboxamide or a pharmaceutically acceptable acid addition salt thereof.

31. The method of claim 1 wherein the compound is 3-(2-pyridinyloxy)-1-azetidinecarboxamide or a pharmaceutically acceptable acid addition salt thereof.

32. The method of claim 1 wherein the compound is 1-propyl-4-[3-[3-(trifluoromethyl)phenoxy]-1-azetidinylcarbonyl]piperazine or a pharmaceutically acceptable acid addition salt thereof.

33. The method of claim 1 wherein the compound is 1-[3-[4-(trifluoromethyl)phenoxy]-1-azetidinylcarbonyl]-1H-imidazole or a pharmaceutically acceptable acid addition salt thereof.

34. The method of claim 1 wherein the compound is 1-[3-[3-(trifluoromethyl)phenoxy]-1-azetidinylcarbonyl]homopiperidine.

35. The method of claim 1 wherein the compound is 1-[3-[3-(trifluoromethyl)phenoxy]-1-azetidinylcarbonyl]piperidine.

36. The method of claim 1 wherein the compound is 1-(1-azetidinylcarbonyl)-3-[3-(trifluoromethyl)phenoxy]azetidine.

37. The method of claim 1 wherein the compound is 1-[3-[3-(trifluoromethyl)phenoxy]-1-azetidinylcarbonyl]pyrrolidine.

38. The method of claim 1 wherein the compound is N-methyl-N-(2-propynyl)-3-[3-(trifluoromethyl)phenoxy]-1-azetidinecarboxamide.

39. The method of claim 1 wherein the compound is 1-methyl-4-[3-[3-(trifluoromethyl)phenoxy]-1-azetidinylcarbonyl]piperazine oxalate [1:1.5].

40. The method of claim 1 wherein the compound is 1-methyl-4-[3-[3-(trifluoromethyl)phenoxy]-1-azetidinylcarbonyl]piperazine or a pharmaceutically acceptable acid addition salt thereof.

41. The method of claim 1 wherein the compound is 1-methyl-4-[3-[3-(trifluoromethyl)phenoxy]-1-azetidinylcarbonyl]piperazine fumarate [1:1].

42. The method of claim 1 wherein the compound is N-(4-methylphenyl)-3-[3-(trifluoromethyl)phenoxy]-1-azetidinecarboxamide.

43. The method of claim 1 wherein the compound is N-(4-chlorophenyl)-3-[3-(trifluoromethyl)phenoxy]-1-azetidinecarboxamide.

44. The method of claim 1 wherein the compound is 3-(4-fluorophenoxy)-N-(2-propenyl)-1-azetidinecarboxamide.

45. The method of claim 1 wherein the compound is 3-(4-fluorophenoxy)-N-(2-propynyl)-1-azetidinecarboxamide.

46. The method of claim 1 wherein the compound is 3-(3,4-dichlorophenoxy)-N-(2-propenyl)-1-azetidine carboxamide.

47. The method of claim 1 wherein the compound is 3-(3,4-dichlorophenoxy)-N-(2-propynyl)-1-azetidinecarboxamide.

48. The method of claim 1 wherein the compound is 3-(4-chlorophenoxy)-N-(2-propynyl)-1-azetidinecarboxamide.

49. The method of claim 1 wherein the compound is 3-(3-bromophenoxy)-N-(2-propenyl)-1-azetidinecarboxamide.

50. The method of claim 1 wherein the compound is 3-(4-chlorophenoxy)-N-(2-propenyl)-1-azetidinecarboxamide.

51. The method of claim 1 wherein the compound is 3-(3-bromophenoxy)-N-(2-propynyl)-1-azetidinecarboxamide.

52. The method of claim 1 wherein the compound is 3-(4-bromophenoxy)-N-(2-propenyl)-1-azetidinecarboxamide.

53. The method of claim 1 wherein the compound is 3-(4-bromophenoxy)-N-(2-propynyl)-1-azetidinecarboxamide.

54. The method of claim 1 wherein the compound is 3-(3-methylphenoxy)-N-(2-propenyl)-1-azetidinecarboxamide.

55. The method of claim 1 wherein the compound is 3-(3-methylphenoxy)-N-(2-propynyl)-1-azetidinecarboxamide.

56. The method of claim 1 wherein the compound is 3-(3-methoxyphenoxy)-N-(2-propenyl)-1-azetidinecarboxamide.

57. The method of claim 1 wherein the compound is 3-(3-methoxyphenoxy)-N-(2-propynyl)-1-azetidinecarboxamide.

58. The method of claim 1 wherein the compound is 1-[3-(4-bromophenoxy)-1-azetidinylcarbonyl]-4-phenylpiperazine or a pharmaceutically acceptable acid addition salt thereof.

59. The method of claim 1 wherein the compound is 1-[3-(4-bromophenoxy)-1-azetidinylcarbonyl]-4-(phenylmethyl)piperazine or a pharmaceutically acceptable acid addition salt thereof.

60. The method of claim 1 wherein the compound is 1-[3-(4-bromophenoxy)-1-azetidinylcarbonyl]-4-methylpiperazine fumarate [1:1].

61. The method of claim 1 wherein the compound is 1-[3-(4-bromophenoxy)-1-azetidinylcarbonyl]-4-methylpiperazine or a pharmaceutically acceptable acid addition salt thereof.

62. The method of claim 1 wherein the compound is 1-[3-(3-bromophenoxy)-1-azetidinylcarbonyl]-4-methylpiperazine fumarate [1:1].

63. The method of claim 1 wherein the compound is 1-[3-(3-bromophenoxy)-1-azetidinylcarbonyl]-4-methylpiperazine or a pharmaceutically acceptable acid addition salt thereof.

64. The method of claim 1 wherein the compound is 1-[3-(4-fluorophenoxy)-1-azetidinylcarbonyl]-4-methylpiperazine fumarate [1:1].

65. The method of claim 1 wherein the compound is 1-[3-(4-fluorophenoxy)-1-azetidinylcarbonyl]-4-methylpiperazine or a pharmaceutically acceptable acid addition salt thereof.

66. The method of claim 1 wherein the compound is 1-[3-(4-fluorophenoxy)-1-azetidinylcarbonyl]-4-phenylpiperazine or a pharmaceutically acceptable acid addition salt thereof.

67. The method of claim 1 wherein the compound is 1-[3-(4-fluorophenoxy)-1-azetidinylcarbonyl]-4-(phenylmethyl)piperazine or a pharmaceutically acceptable acid addition salt thereof.

68. The method of claim 1 wherein the compound is 1-[3-(4-fluorophenoxy)-1-azetidinylcarbonyl]-4-(phenylmethyl)piperazine fumarate [1:1].

69. The method of claim 1 wherein the compound is 1-[3-(3,4-dichlorophenoxy)-1-azetidinylcarbonyl]-4-methylpiperazine fumarate [1:1].

70. The method of claim 1 wherein the compound is 1-[3-(3,4-dichlorophenoxy)-1-azetidinylcarbonyl]-4-methylpiperazine or a pharmaceutically acceptable acid addition salt thereof.

71. The method of claim 1 wherein the compound is 1-[3-(3,4-dichlorophenoxy)-1-azetidinylcarbonyl]-4-(phenylmethyl)piperazine fumarate [1:1].

72. The method of claim 1 wherein the compound is 1-[3-(3,4-dichlorophenoxy)-1-azetidinylcarbonyl]-4-(phenylmethyl)piperazine or a pharmaceutically acceptable acid addition salt thereof.

73. The method of claim 1 wherein the compound is 1-phenyl-4-[3-[3-(trifluoromethyl)phenoxy]-1-azetidinylcarbonyl]piperazine or a pharmaceutically acceptable acid addition salt thereof.

74. The method of claim 1 wherein the compound is 1-(2-pyridinyl)-4-[3-[3-(trifluoromethyl)phenoxy]-1-azetidinylcarbonyl]piperazine or a pharmaceutically acceptable acid addition salt thereof.

75. The method of claim 1 wherein the compound is 4-phenyl-1-[3-[3-(trifluoromethyl)phenoxy]-1-azetidinylcarbonyl]piperidine.

76. The method of claim 1 wherein the compound is 1,2,3,6-tetrahydro-4-phenyl-1-[3-[3-(trifluoromethyl)phenoxy]-1-azetidinylcarbonyl]pyridine.

77. The method of claim 1 wherein the compound is 1-[3-(3,4-dichlorophenoxy)-1-azetidinylcarbonyl]-4-(2-pyridinyl)piperazine or a pharmaceutically acceptable acid addition salt thereof.

78. The method of claim 1 wherein the compound is 1-[3-(3-bromophenoxy)-1-azetidinylcarbonyl]-4-(phenylmethyl)piperazine fumarate [1:1].

79. The method of claim 1 wherein the compound is 1-[3-(3-bromophenoxy)-1-azetidinylcarbonyl]-4-(phenylmethyl)piperazine or a pharmaceutically acceptable acid addition salt thereof.

80. The method of claim 1 wherein the compound is 4-(4-chlorophenyl)-1-[3-[3-(trifluoromethyl)phenoxy]-1-azetidinylcarbonyl]-4-piperidinol.

81. The method of claim 1 wherein the compound is 2-[4-[3-[3-(trifluoromethyl)phenoxy]-1-azetidinylcarbonyl]-1-piperazinyl]pyrimidine or a pharmaceutically acceptable acid addition salt thereof.

82. The method of claim 1 wherein the compound is 1-(phenylmethyl)-4-[3-[3-(trifluoromethyl)phenoxy]-1-azetidinylcarbonyl]piperazine fumarate [1:1].

83. The method of claim 1 wherein the compound is 1-(phenylmethyl)-4-[3-[3-(trifluoromethyl)phenoxy]-1-azetidinylcarbonyl]piperazine or a pharmaceutically acceptable acid addition salt thereof.

84. The method of claim 1 wherein the compound is 3-[(4-chlorophenyl)thio]-N-(2-propenyl)-1-azetidinecarboxamide.

85. The method of claim 1 wherein the compound is 1-[3-[(4-chlorophenyl)thio]-1-azetidinylcarbonyl]-4-methylpiperazine fumarate [1:1].

86. The method of claim 1 wherein the compound is 1-[3-[(4-chlorophenyl)thio]-1-azetidinylcarbonyl]-4-methylpiperazine or a pharmaceutically acceptable acid addition salt thereof.

87. The method of claim 1 wherein the compound is octahydro-2-[3-[3-(trifluoromethyl)phenoxy]-1-azetidinylcarbonyl]pyrrolo[1,2-a]pyrazine or a pharmaceutically acceptable salt thereof.

88. The method of claim 1 wherein the compound is 1-[3-(4-fluorophenoxy)-1-azetidinylcarbonyl]piperazine or a pharmaceutically acceptable acid addition salt thereof.

89. The method of claim 1 wherein the compound is hexahydro-1-methyl-4-[3-[3-(trifluoromethyl)phenoxy]-1-azetidinylcarbonyl]-1H-1,4-diazepine or a pharmaceutically acceptable acid addition salt thereof.

90. The method of claim 1 wherein the compound is cis-2-methyl-N-(2-propenyl)-3-[3-(trifluoromethyl)phenoxy]-1-azetidine carboxamide.

91. The method of claim 1 wherein the compound is cis-2-methyl-3-[3-(trifluoromethyl)phenoxy]-1-azetidinecarboxamide.

92. The method of claim 1 wherein the compound is N-methyl-N-(2-propenyl)-3-[3-(trifluoromethyl)phenoxy]-1-azetidinecarboxamide or a hydrate thereof.

93. The method of claim 1 wherein the compound is 3-(3-methoxyphenoxy)-N-methyl-1-azetidinecarboxamide.

94. The method of claim 1 wherein the compound is 4-[3-(4-fluorophenoxy)-1-azetidinylcarbonyl]-1-piperazinecarboxylic acid ethyl ester.

* * * * *